(12) United States Patent
Lee et al.

(10) Patent No.: US 10,319,922 B2
(45) Date of Patent: Jun. 11, 2019

(54) COMPOUND FOR ORGANIC ELECTRONIC ELEMENT, ORGANIC ELECTRONIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Bumsung Lee, Cheonan-si (KR); Sun-hee Lee, Cheonan-si (KR); Daesung Kim, Yongin-si (KR); Yun Suk Lee, Seoul (KR); Gyumin Lee, Cheonan-si (KR)

(73) Assignee: Duk San Neolux Co., Ltd., Cheonan-si, Chungcheongnam-do (KR)

( * ) Notice: Subject to any disclaimer, the term of this patent is extended or adjusted under 35 U.S.C. 154(b) by 0 days.

(21) Appl. No.: 15/977,327

(22) Filed: May 11, 2018

(65) Prior Publication Data

US 2018/0277770 A1   Sep. 27, 2018

Related U.S. Application Data

(63) Continuation of application No. 15/517,391, filed as application No. PCT/KR2015/009451 on Sep. 8, 2015.

(30) Foreign Application Priority Data

Oct. 6, 2014 (KR) .................. 10-2014-0133993

(51) Int. Cl.
| | | |
|---|---|---|
| *C07D 409/14* | (2006.01) | |
| *H01L 51/00* | (2006.01) | |
| *C07D 209/82* | (2006.01) | |
| *H01L 51/50* | (2006.01) | |

(52) U.S. Cl.
CPC ........ *H01L 51/0072* (2013.01); *C07D 209/82* (2013.01); *C07D 409/14* (2013.01); *H01L 51/006* (2013.01); *H01L 51/5092* (2013.01); *H01L 51/0067* (2013.01); *H01L 51/0074* (2013.01); *H01L 51/0096* (2013.01); *H01L 51/5012* (2013.01); *H01L 51/5056* (2013.01); *Y02E 10/549* (2013.01)

(58) Field of Classification Search
CPC .................................................... C07D 409/14
See application file for complete search history.

(56) References Cited

U.S. PATENT DOCUMENTS

2012/0205636 A1*  8/2012  Kim ..................... C09K 11/06
                                                          257/40

FOREIGN PATENT DOCUMENTS

WO      2014/021572 A1     2/2014

OTHER PUBLICATIONS

Office Action dated Jan. 24, 2019 for corresponding CN 201580055069.7, 6 pages.

* cited by examiner

*Primary Examiner* — Shawquia Jackson
(74) *Attorney, Agent, or Firm* — Vorys, Sater, Seymour and Pease LLP; Mih Suhn Koh

(57) ABSTRACT

Provided are a compound of Formula 1 and an organic electric element comprising a first electrode, a second electrode, and an organic material layer formed between the first electrode and the second electrode, and electronic device comprising the organic electric element, wherein the luminous efficiency and life span can be improved and the driving voltage of the organic electronic device can be lowered by comprising the compound represented by Formula 1 in the organic material layer.

9 Claims, 1 Drawing Sheet

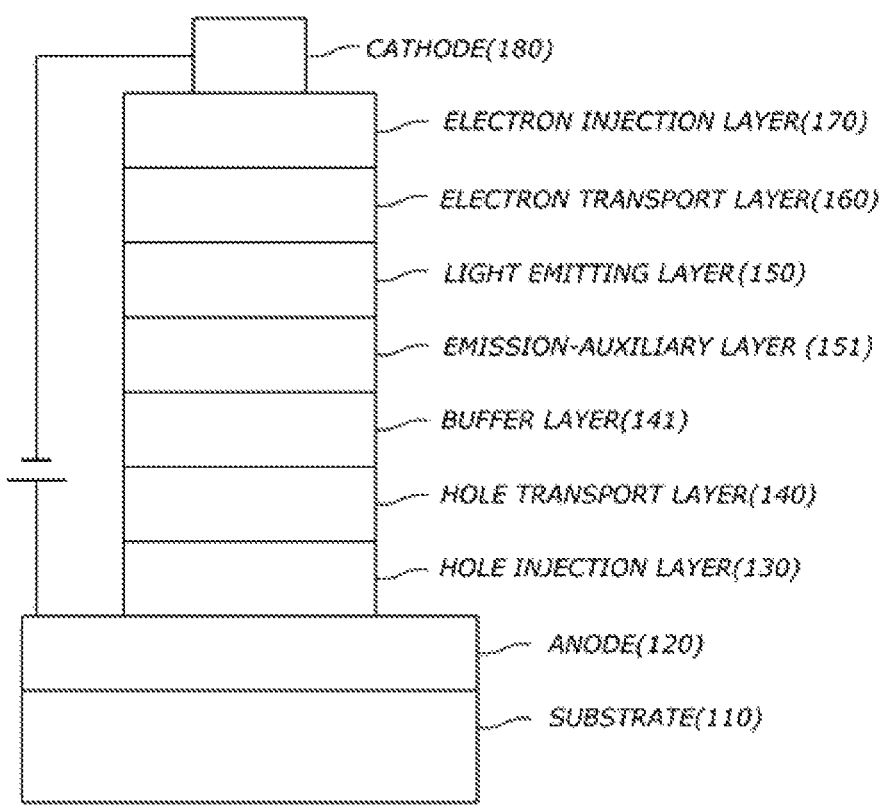

COMPOUND FOR ORGANIC ELECTRONIC ELEMENT, ORGANIC ELECTRONIC ELEMENT COMPRISING THE SAME AND ELECTRONIC DEVICE THEREOF

CROSS-REFERENCE TO RELATED APPLICATION

This patent application claims benefit under 119(a) (35 U.S.C. § 119(a)) to Korean Patent Application No. 10-2014-0133993, filed on Oct. 6, 2014, the contents of which are hereby incorporated by reference for all purposes as if fully set forth herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is an important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Recently, in order to solve the problem of light emission in the hole transporting layer of an organic electric element, it is preferable that an emission-auxiliary layer exists between the hole transport layer and the light emitting layer.

It is necessary to develop different emission-auxiliary layer materials depending on the respective light emitting layers (R, G, B).

In general, electrons are transferred from the electron transport layer to the light emitting layer and holes are transferred from the hole transport layer to the light emitting layer to generate excitons by recombination.

However, since the material used for the hole transport layer has a low HOMO value, it has a low T1 value, which causes the exciton generated in the light emitting layer to be transferred to the hole transport layer. As a result, a charge unbalance occurs in the light emitting layer, and light emission occurs in the hole transport layer or at the interface of the hole transport layer, resulting in showing poor color purity, reduced efficiency, and low life span.

In addition, when a material having a high hole mobility is used to make a low driving voltage, the efficiency tends to decrease. This is because the hole mobility is faster than the electron mobility in a general organic electronic element, resulting in a charge unbalance in the light emitting layer. As a result, efficiency and life span are decreased.

Therefore, in order to solve the problems of the hole transport layer above, an emission-auxiliary layer material should have a hole mobility (hole mobility: within driving voltage range of the full device blue device) and a high $T_1$ value (electron block) and a wide band gap. However, this cannot be achieved simply by the structural properties of the core of an emission-auxiliary layer material, but is possible when the combination of the core and sub-substituent properties of the material is combined. Accordingly, in order to improve the efficiency and life span of the organic electronic device, it is strongly required to develop an emission-auxiliary layer material having a high $T_1$ value and a wide band gap.

That is, in order to sufficiently exhibit the excellent characteristics of the organic electronic device, a material forming the organic material layer, for example, a hole injection material, a hole transport material, a light emitting material, an electron transport material, an electron injection material, an emission-auxiliary layer material or the like, must be supported by a stable and efficient material. However, such a stable and efficient organic material layer material for an organic electric element has not yet been fully developed. Accordingly, there is a continuous need to develop new materials for an organic material layer, specifically, there are strong needs to develop materials for an emission-auxiliary layer.

SUMMARY

In order to solve one or more of the above-mentioned problems occurring in the prior art, an aspect of the present invention is to provide a compound capable of lowering the driving voltage of an organic electronic element and improving the luminous efficiency, color purity and life span of the device, an organic electric element employing such a compound, and an electronic device thereof.

In accordance with an aspect of the present invention, the compound represented by the following Formula 1 is provided.

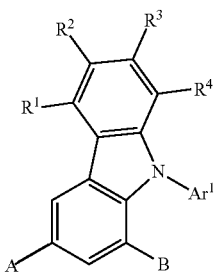

[Formula 1]

In another aspect of the present invention, organic electric elements containing the compound represented by the formula above and electronic devices including the organic electric element are provided.

According to embodiment of the present invention, the driving voltage of an organic electronic element can be lowered, and the luminous efficiency, color purity and life span of an organic electronic element can be improved.

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), iodine (I) and so on.

Unless otherwise stated, the term "alkyl" or "alkyl group" as used herein has a single bond of 1 to 60 carbon atoms, and means aliphatic functional radicals including a linear alkyl group, a branched chain alkyl group, a cyclo alkyl group (alicyclic), or an alkyl group substituted with a cyclo alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cyclo alkyl" as used herein means, but not limited to, alkyl forming a ring having 3 to 60 carbon atoms.

The term "alkoxy group" or "alkyloxy group" as used herein means an oxygen radical attached to an alkyl group, but not limited to, and has 1 to 60 carbon atoms.

The term "aryloxy group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbon to which they are attached to form spiro compound.

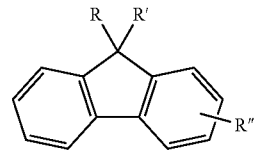

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

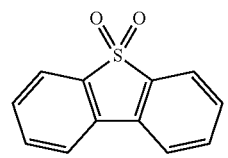 [SMILES: O=S1(=O)c2ccccc2-c2ccccc21]

In the present description, a monovalent or divalent functional group may be named as a functional group name or a parent compound name with valence number in front of the parent compound name. For example, "divalent benzothiophene" means a divalent functional group of benzothiophene which is a parent compound, similarly, "divalent dibenzothiophene" means a divalent functional group of dibenzothiophene which is a parent compound, "divalent furan" means a divalent functional group of furan which is a parent compound, "divalent dibenzofuran" means a divalent functional group of dibenzofuran which is a parent compound, and "divalent pyridine" means a divalent functional group of a pyridine which is a parent compound. Likewise, a trivalent functional group can be represented by a trivalent sign in front of the parent compound, for example, "trivalent aryl" represents a trivalent functional group of aryl which is aromatic, "trivalent fluorene" represents a trivalent functional group of fluorene.

Unless otherwise stated, the term "ring" as used herein comprises monocyclic and polycyclic rings, a heterocycle containing at least one heteroatom as well as hydrocarbon ring, and both aromatic and non-aromatic rings.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

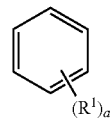

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different each other, and are linked to the benzene ring as follows. when a is an integer of 4 to 6, the substituents $R^1$s are linked to carbon atom of the benzene ring in a similar manner to that. Meanwhile, hydrogen atoms linked to carbon constituting the benzene ring may not be represented as usual.

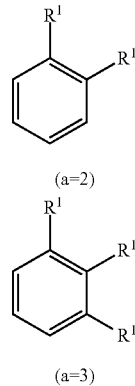

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer therebetween which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, at least one of the layers may not be formed. The organic material layer may further include a hole blocking layer, an electron blocking layer, an emission-auxiliary layer 151, a buffer layer 141 and so on, and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an electron transport layer 160, an electron injection layer 170, as a host material or a dopant material of a light emitting layer 150, or as a material a capping layer material. For example, the inventive compound may be used as material of the light emitting layer 150, the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent bonded to the core. Specially, long life span and high efficiency can be simultaneously achieved when the optimal combination of energy levels and $T_1$ values, inherent material properties (mobility, interfacial properties, etc.), and the like among the respective layers of an organic material layer is achieved.

As already described above, in order to solve the emission problem with a hole transport layer in a conventional organic electric element, it is preferable that an emission-auxiliary layer is formed between the hole transport layer and a light emitting layer, and it is time to develop different emission-auxiliary layers according to respective light emitting layers (R, G, B). Meanwhile, even when a similar core is used, it is very difficult to infer the characteristics of an emission-auxiliary layer if a used organic material layer varies, because the correlation between the emission-auxiliary layer and a hole transport layer and between the emission-auxiliary layer and a light emitting layer (host) must be figured out.

Accordingly, in the present invention, energy levels, $T_1$ values and inherent material properties (mobility, interfacial properties, etc.) among the respective organic material layers are optimized by forming a hole transport layer or/and an emission-auxiliary layer employing compound represented by Formula 1, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emission-auxiliary layer 151 may be further formed between a hole transport layer 140 and a light emitting layer 150.

Further, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer process. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G(Green), B(Blue) light-emitting units, a vertical stack arrangement method of RGB light-emitting units, and a CCM (color conversion material) method in which electroluminescence from a blue (B) organic light emitting layer, and the present invention may be applied to such WOLED.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

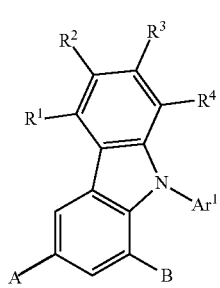

[Formula 1]

In the above formula, each symbol is defined as follows.

In formula 1, "A" and "B" may be each independently selected from the group consisting of formula 1-1, formula 1-2 and formula 1-3 below, wherein it is preferable that the case where "A" and "B" are simultaneously the formula 1-3 is excluded. Also, it is preferable that the case where $Ar^1$ to $Ar^3$ are all phenyl and $L^1$ is meta-phenylene when "A" is formula 1-1 is excluded.

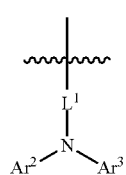

<Formula 1-1>

-continued

<Formula 1-2>

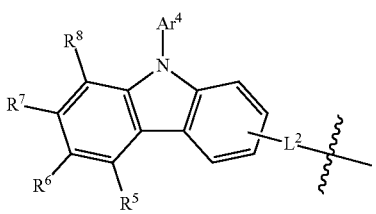

<Formula 1-3>

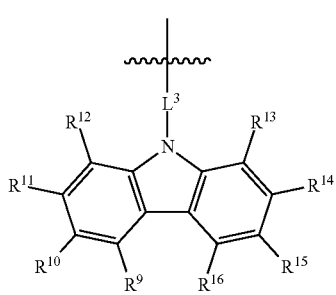

In the above Formulas 1, 1-1 and 1-2, $Ar^1$ to $Ar^4$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; -L'-N($R^a$)($R^b$); and the combination thereof, wherein $Ar^2$ and $Ar^3$ may be linked to each other to form a ring together with nitrogen to which $Ar^2$ and $Ar^3$ are bonded.

Preferably, $Ar^1$ to $Ar^4$ may be each independently a $C_6$-$C_{25}$ aryl group, a fluorenyl group, or a $C_3$-$C_{16}$ heterocyclic group, also preferably, a $C_6$, $C_{10}$, $C_{12}$, or $C_{14}$ aryl group, or a $C_5$, or $C_{12}$ heterocyclic group, specifically, a phenyl group, a naphthyl group, a biphenylyl group, a phenanthryl group, a fluorenyl group substituted or unsubstituted with methyl or phenyl, a spirobifluorenyl group, a pyridyl group or a dibenzothienyl group.

Preferably, $Ar^1$ to $Ar^4$ may be further substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

In the above Formulas 1-1, 1-2 and 1-3, $L^1$ to $L^3$ may be each independently selected from the group consisting of a single bond; a $C_6$-$C_{60}$ arylene group; a fluorenylene group; a fused ring formed by a $C_6$-$C_{60}$ aromatic ring and a $C_3$-$C_{60}$ aliphatic ring; a $C_2$-$C_{60}$ heterocyclic group containing at least one heteroatom selected from the group consisting of O, N, S, Si, and P; and the combination thereof.

Preferably, the above $L^1$ to $L^3$ may be each independently a single bond, a $C_6$-$C_{18}$ arylene group, a fluorenylene group, or a $C_3$-$C_{12}$ heterocyclic group and so on, also preferably, a $C_6$ arylene group, or a $C_5$ or $C_{12}$ heterocyclic group, specifically, a single bond, a phenylene group, a fluorenylene group substituted or unsubstituted with methyl or phenyl, a spirobifluorenylene group, a pyridylene group, a dibenzothienylene group, or a combination thereof.

Preferably, the above $L^1$ to $L^3$ may be further substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

The above Formulas 1, 1-1, 1-2 and 1-3, $R^1$ to $R^{16}$ may be each independently selected from the group consisting of hydrogen; deuterium; halogen; a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-N($R^a$)($R^b$); and the combination thereof, wherein neighboring $R^1$s to $R^{16}$s groups may be linked to each other to form a ring together with a benzene ring to which they are bonded.

Preferably, neighboring $R^1$s to $R^{16}$s groups may be linked to each other to form a ring together with a benzene ring to which they are bonded. For example, $R^1$ and $R^2$, $R^2$ and $R^3$, $R^3$ and $R^4$, $R^5$ and $R^6$, $R^6$ and $R^7$, $R^7$ and $R^8$, $R^9$ and $R^{10}$, $R^{10}$ and $R^{11}$, $R^{11}$, and $R^{12}$, $R^{13}$ and $R^{14}$, $R^{14}$ and $R^{15}$, and/or $R^{15}$ and $R^{16}$ may be linked to each other to form a ring together with a benzene ring to which they are bonded. That is, at least a couple of neighboring groups may be linked to each other to form a ring. For example, $R^1$ and $R^2$ may be linked to each other to form a ring such as naphthalene together with the benzene ring to which they are bonded, and $R^3$ to $R^{16}$ may be also linked to each other to form a ring.

Preferably, $R^1$ to $R^{16}$ not forming a ring may be each independently hydrogen or a $C_6$-$C_{18}$ aryl group, and also preferably also be a $C_6$ aryl group, specifically hydrogen or a phenyl group.

Preferably, $R^1$ to $R^{16}$ may be further substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

The above L' may be selected from the group consisting of a single bond; a $C_6$-$C_{60}$ arylene group; a fluorenylene group; a fused ring formed by a $C_6$-$C_{60}$ aromatic ring and a $C_3$-$C_{60}$ aliphatic ring; and a $C_2$-$C_{60}$ heterocyclic group containing at least one heteroatom selected from the group consisting of O, N, S, Si, and P, and $R^a$ and $R^b$ may be each independently selected from the group consisting of a $C_6$-$C_{60}$ aryl group; a fluorenyl group; a fused ring formed by a $C_6$-$C_{60}$ aromatic ring and a $C_3$-$C_{60}$ aliphatic ring; and a $C_2$-$C_{60}$ heterocyclic group containing at least one heteroatom selected from the group consisting of O, N, S, Si and P.

Specifically, the following Formulas 2 to 9 show the case where Formulas 1-1, 1-2 and 1-3 are independently bonded to A and B of Formula 1.
<Formula 2>
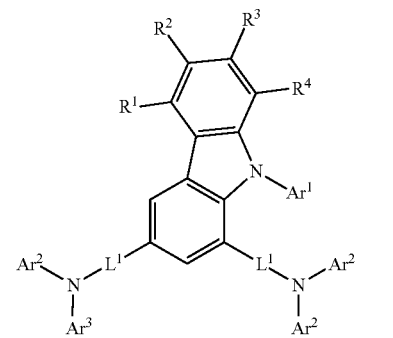
<Formula 3>
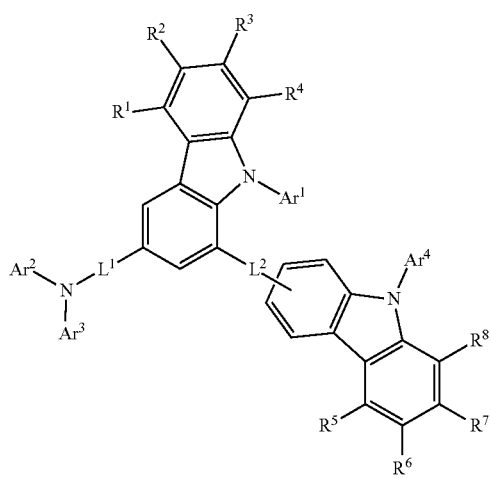
<Formula 4>
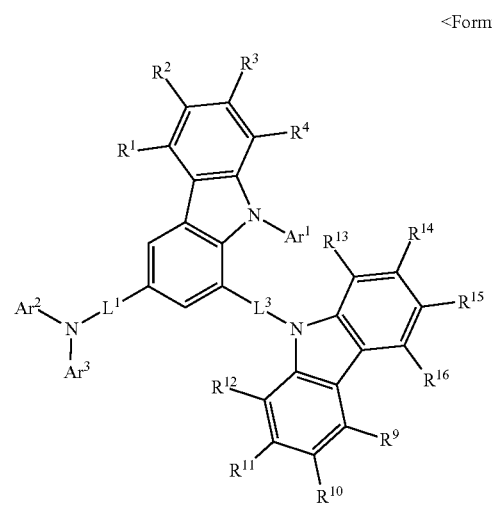
<Formula 5>
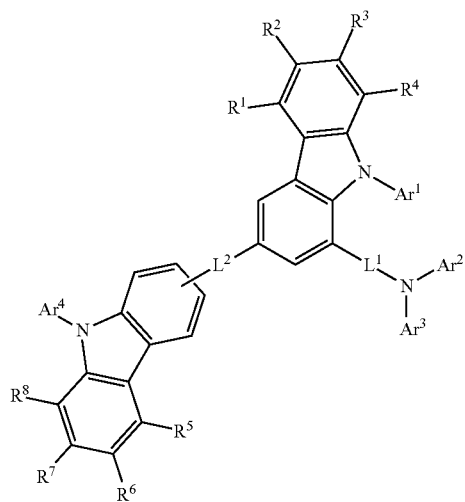
<Formula 6>
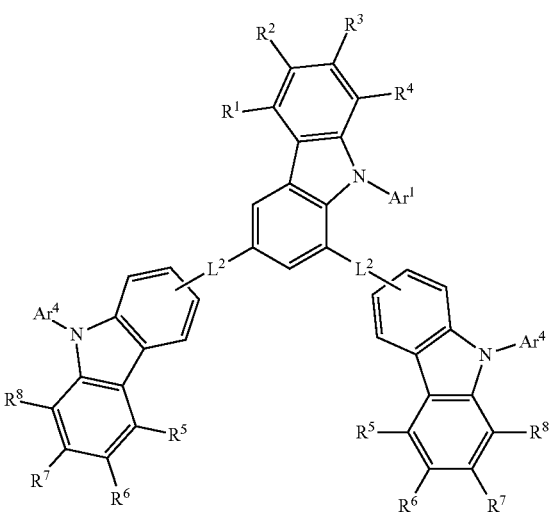
<Formula 7>
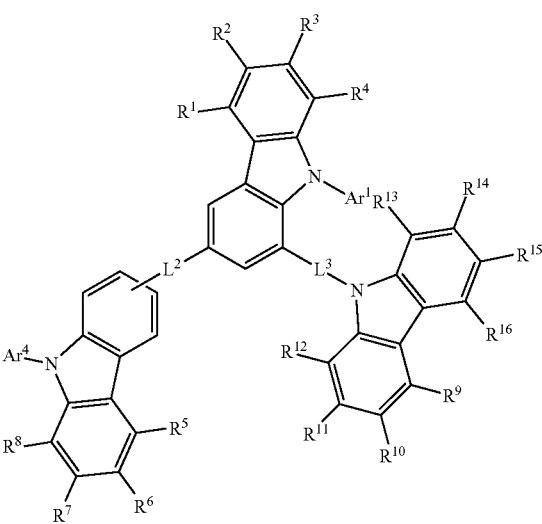

<Formula 8>
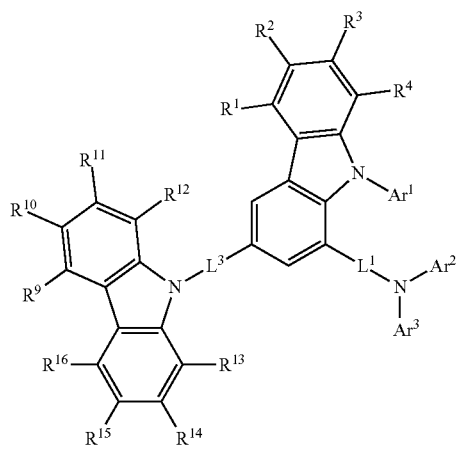
<Formula 9>
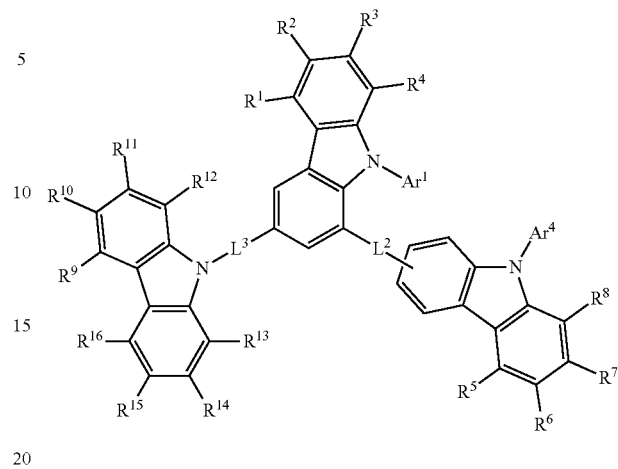
In formulas 2 to 9, $Ar^1$ to $Ar^4$, $L^1$ to $L^3$, $R^1$ to $R^{16}$, and the like are the same as defined in Formulas 1, 1-1, 1-2 and 1-3 above.
More specifically, the compound represented by Formula 1 may be any one of the following compounds.
1-1
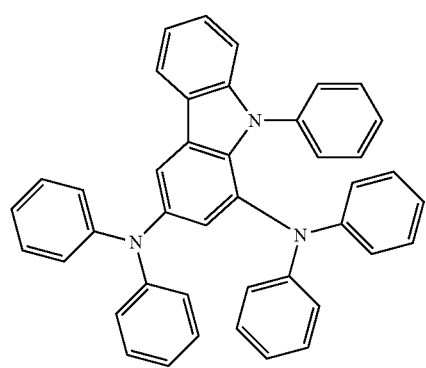
1-2
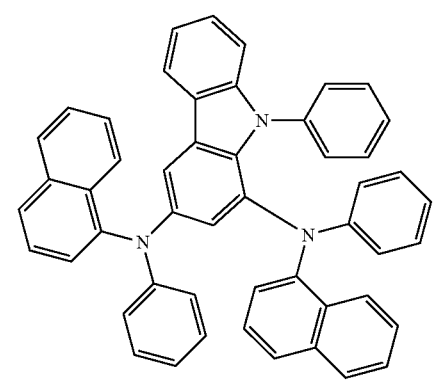
1-3
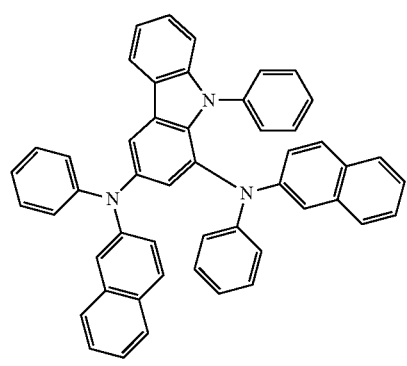
1-4
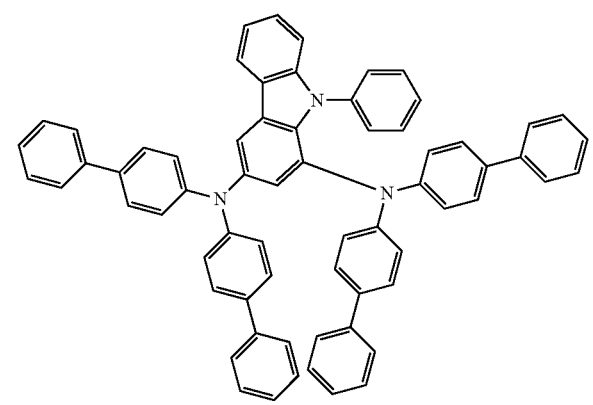

1-5
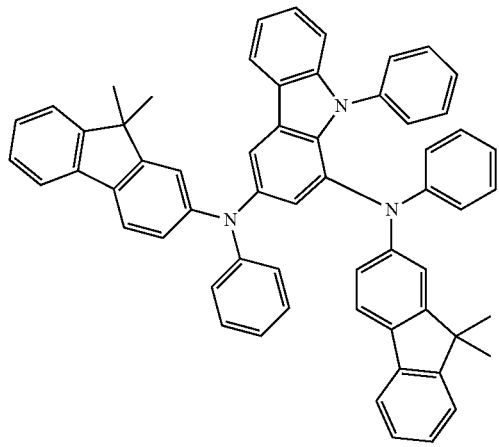
1-6
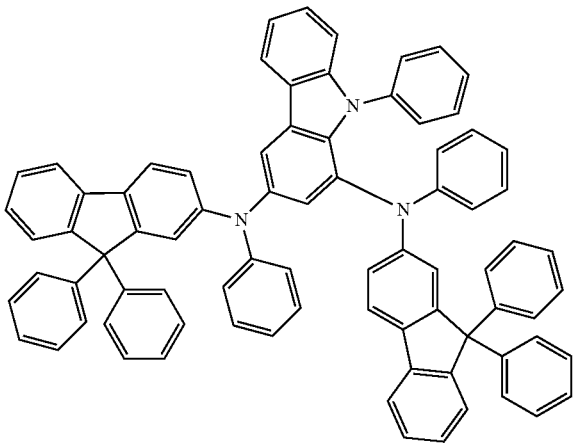
1-7
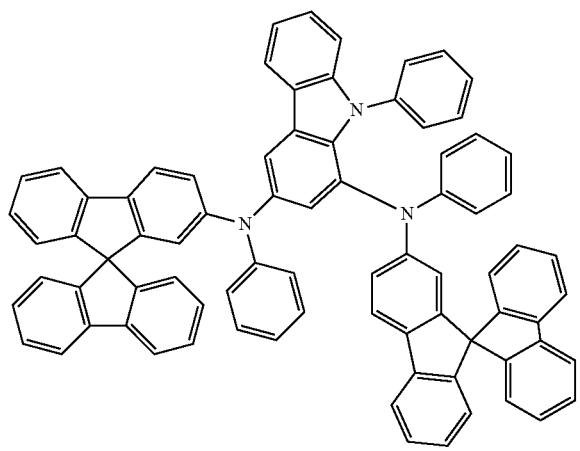
1-8
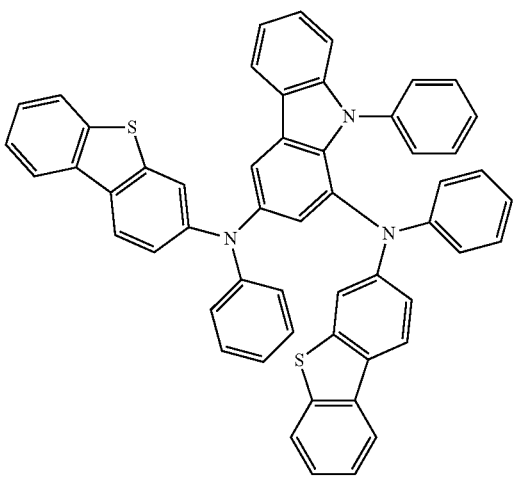
1-9
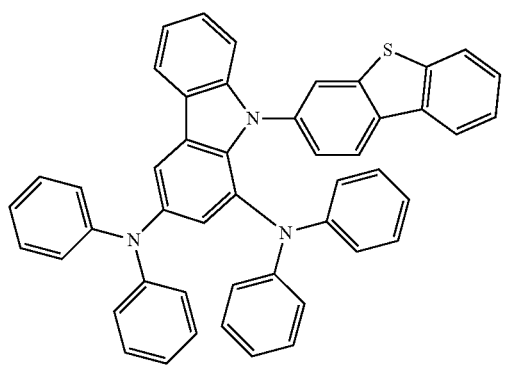
1-10
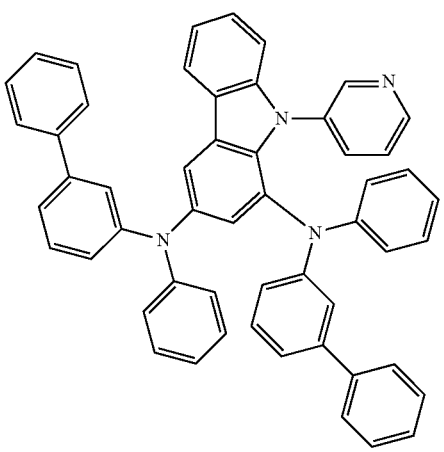

1-11
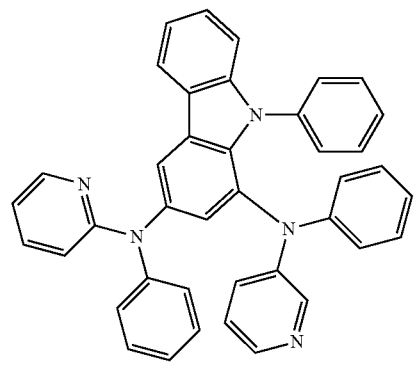
1-12
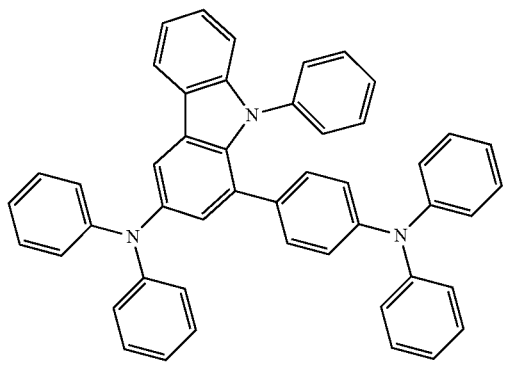
1-13
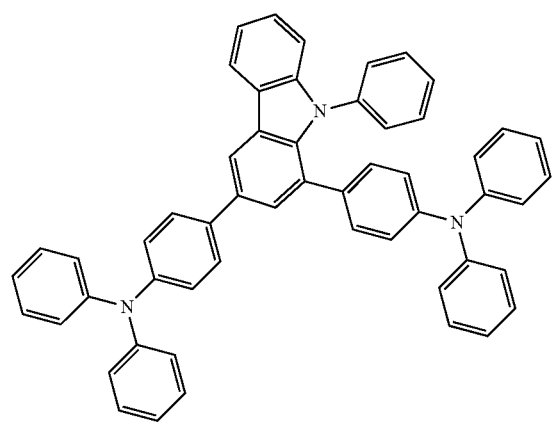
1-14
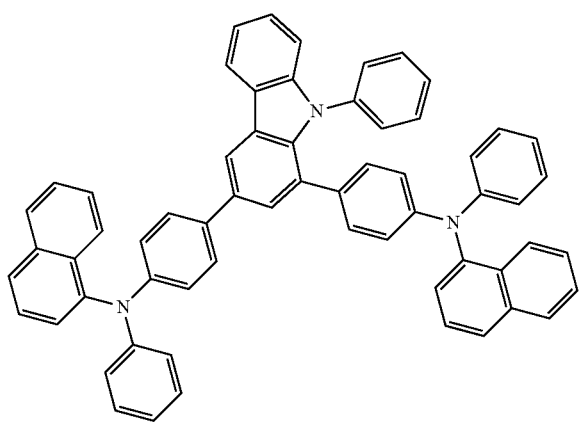
1-15
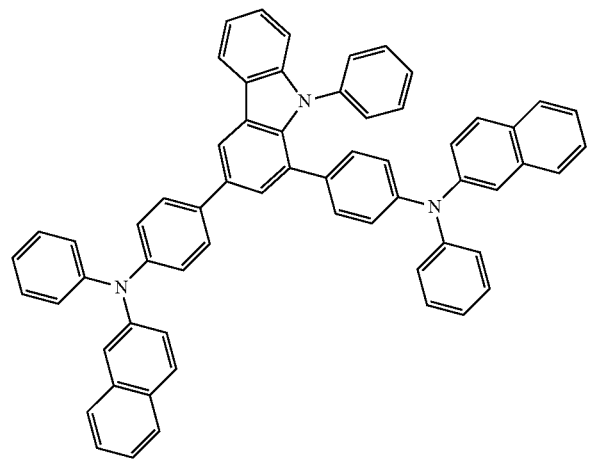

1-16
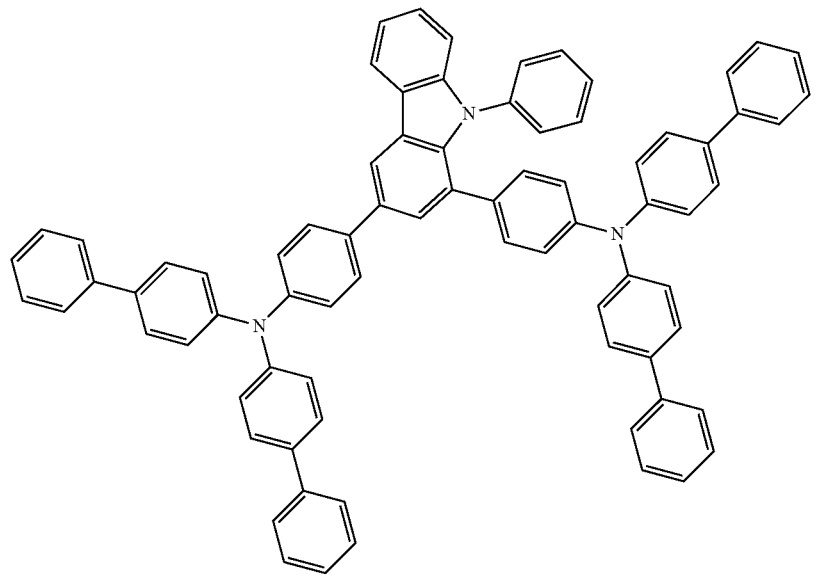
1-17
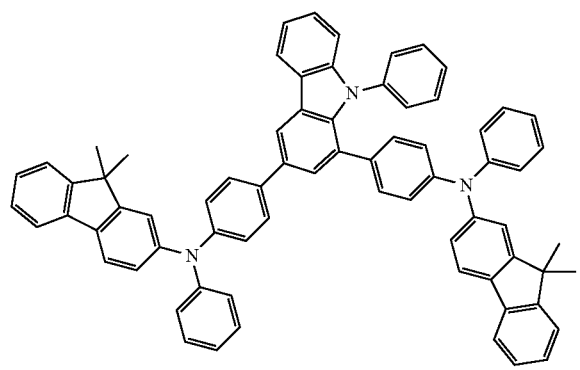
1-18
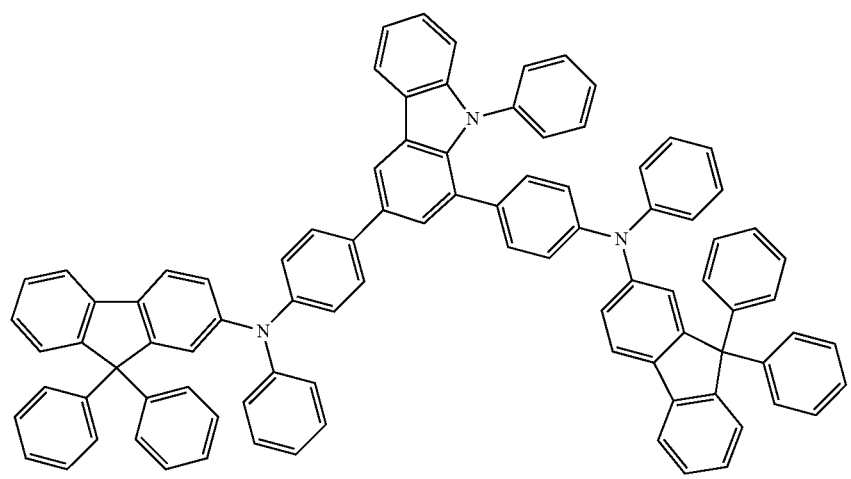

-continued
1-19
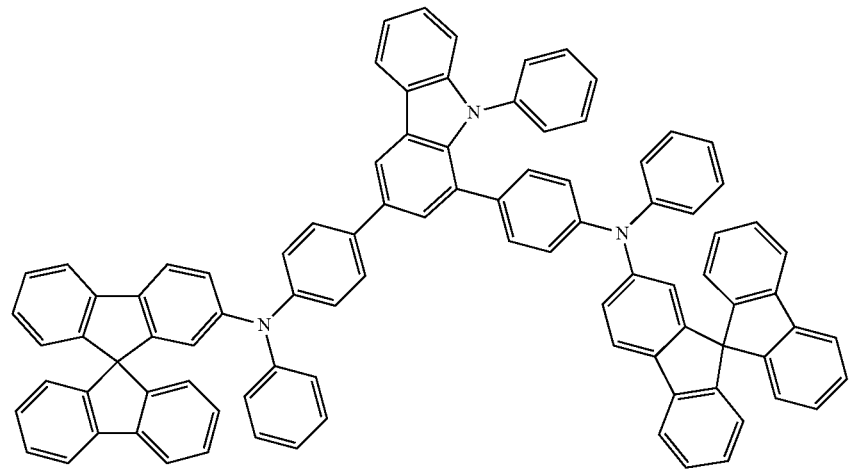
1-20
1-21
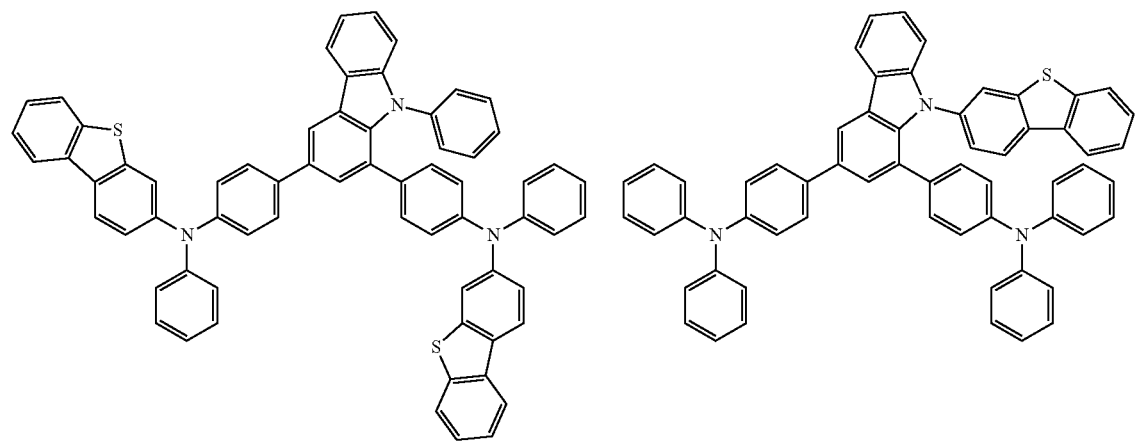
1-22
1-23
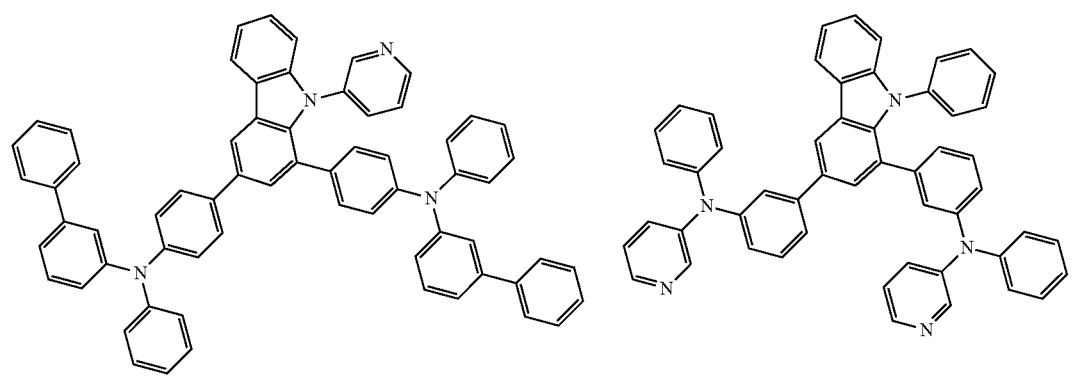

-continued
1-24
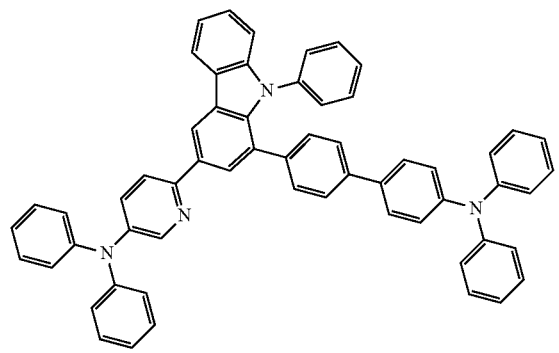
1-25
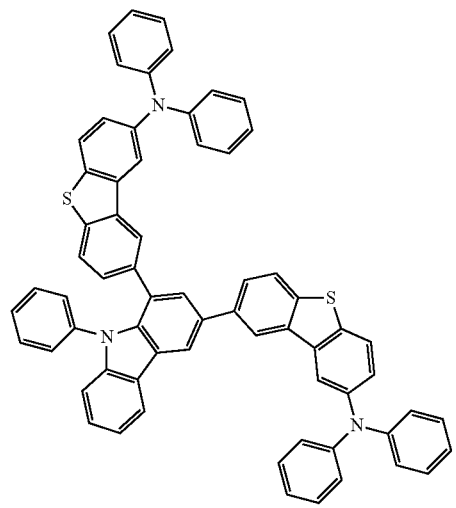
1-26
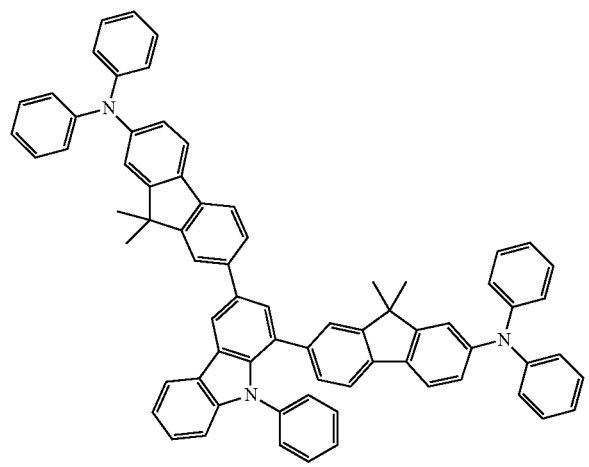
1-27
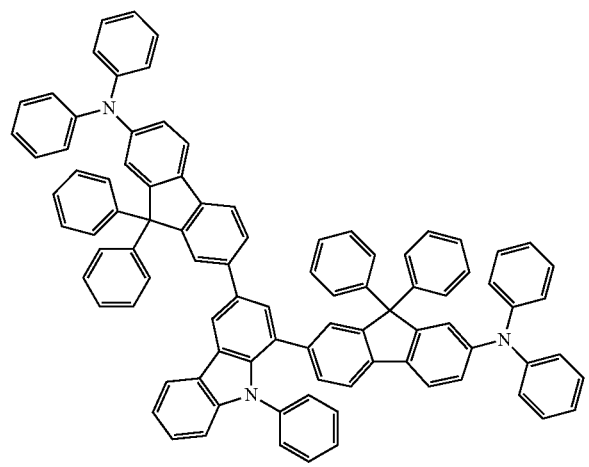
1-28
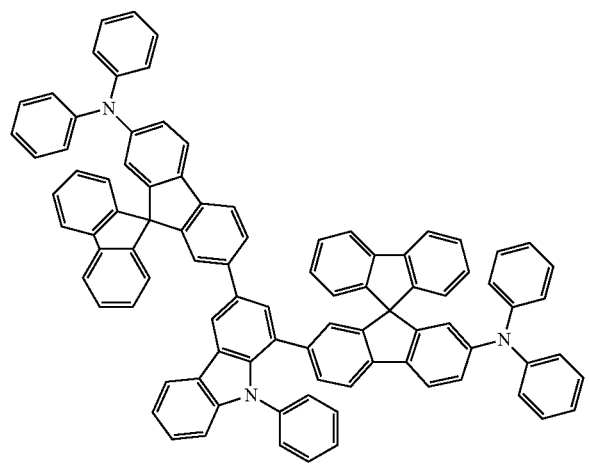
2-1
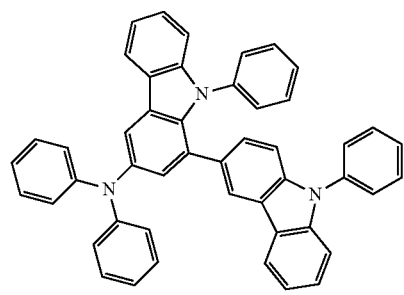

-continued
2-2
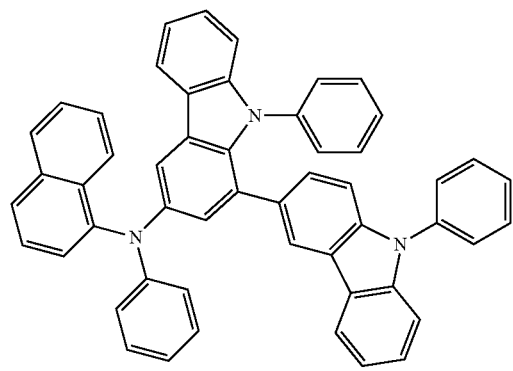
2-3
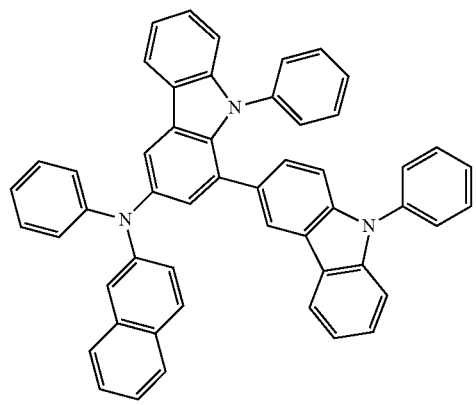
2-4
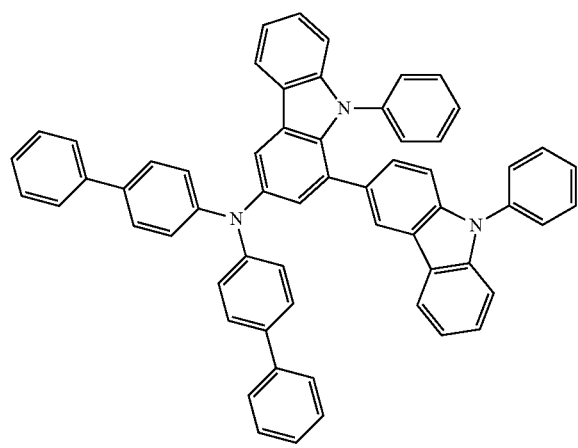
2-5
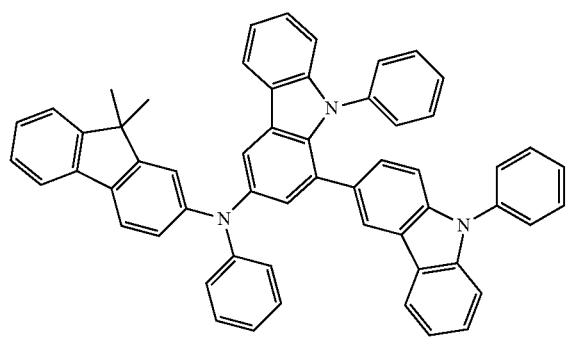
2-6
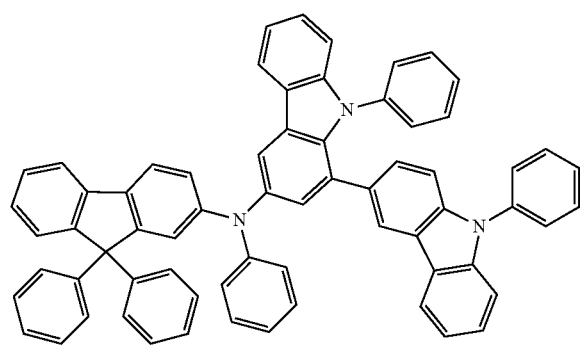
2-7
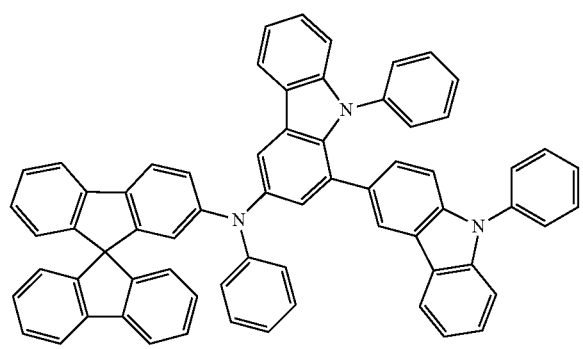
2-8
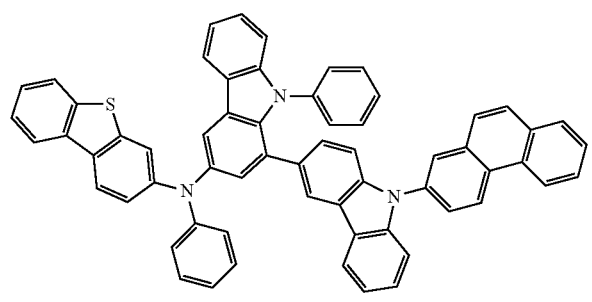
2-9
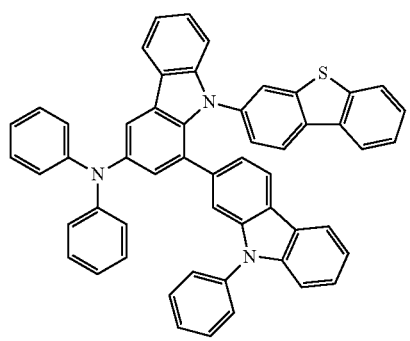

-continued
2-10
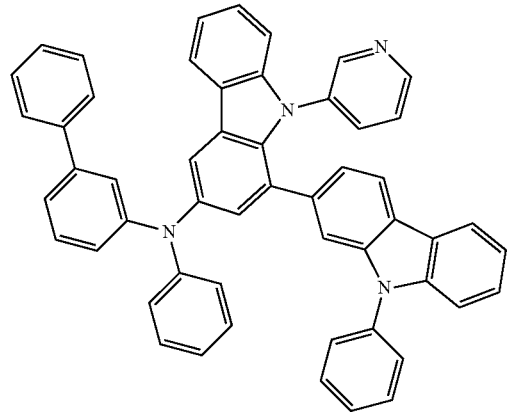
2-11
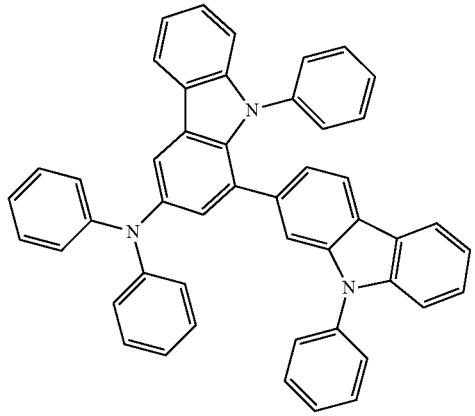
2-12
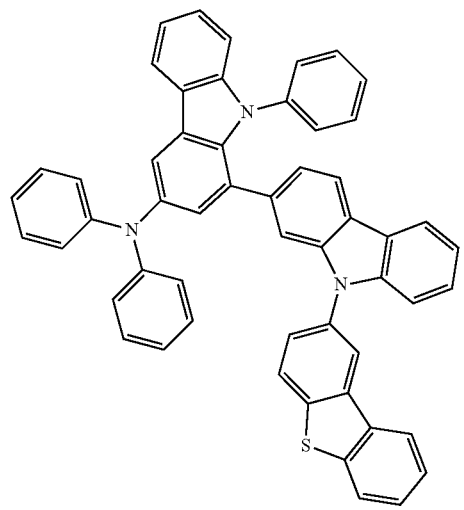
2-13
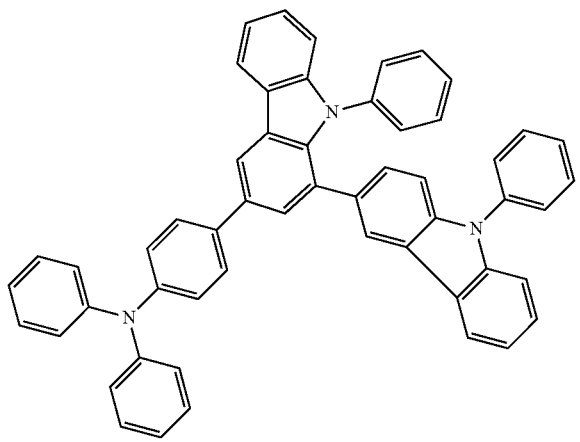
2-14
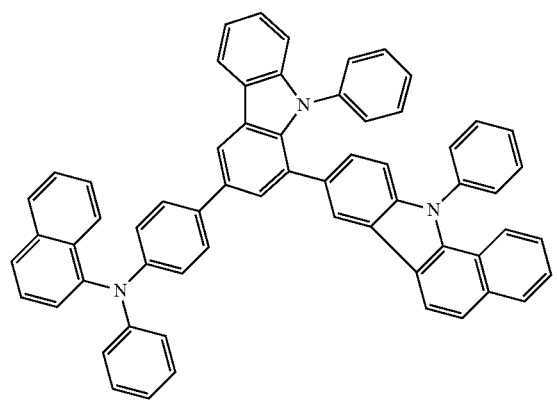
2-15
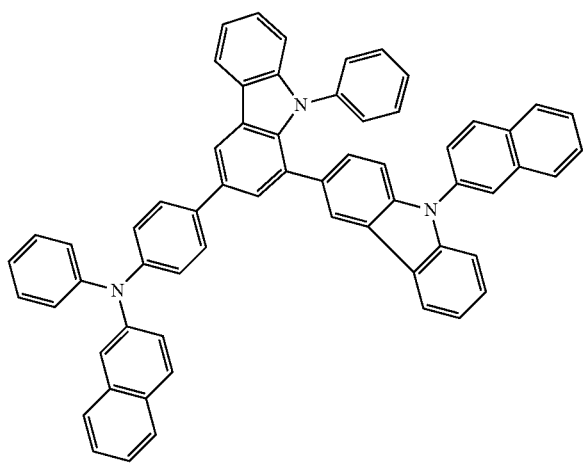

2-16
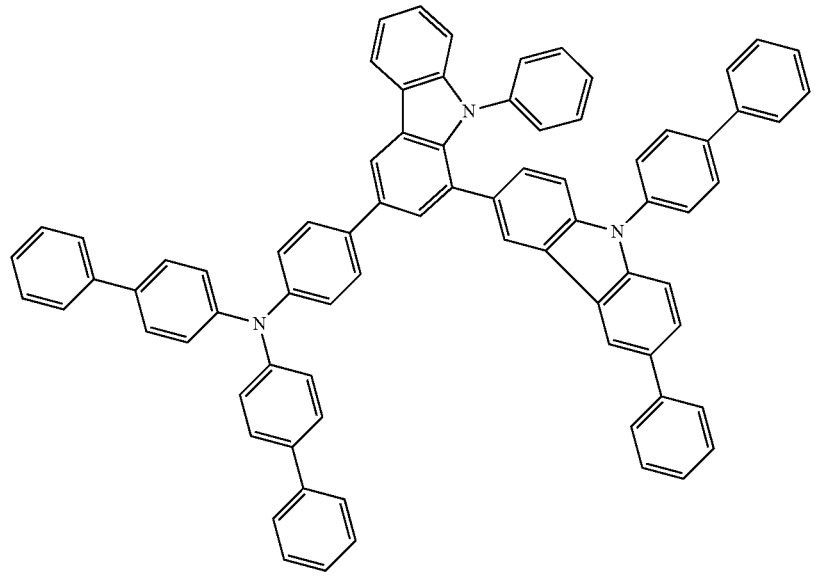
2-17 2-18
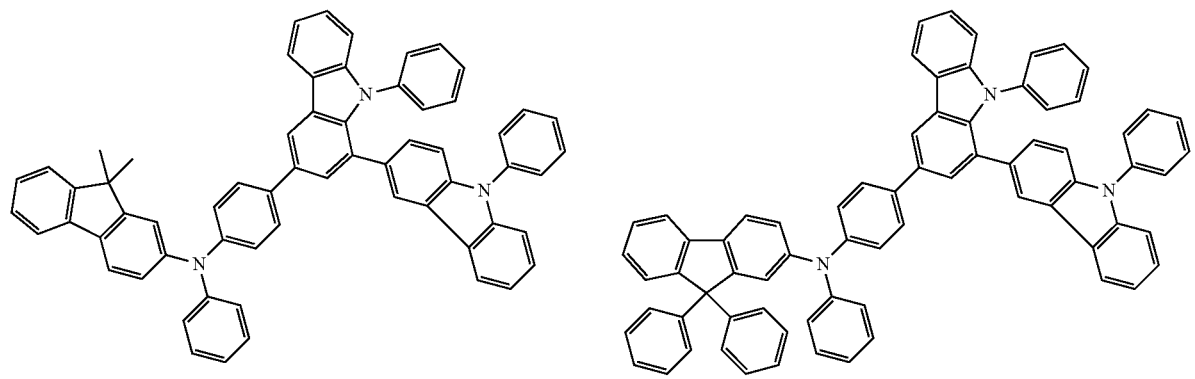
2-19 2-20
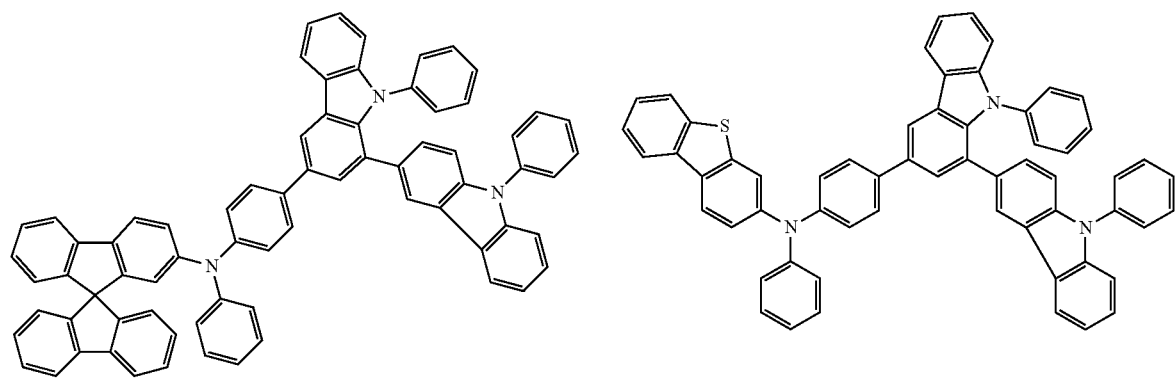

-continued
2-21
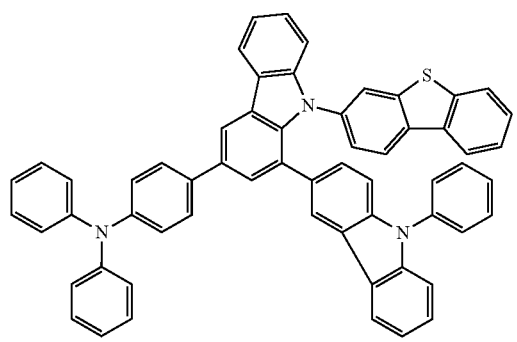
2-22
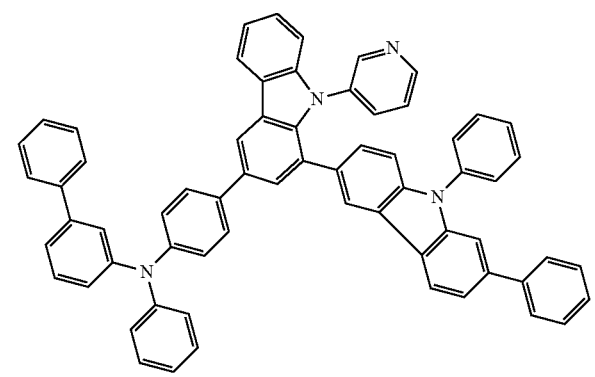
2-23
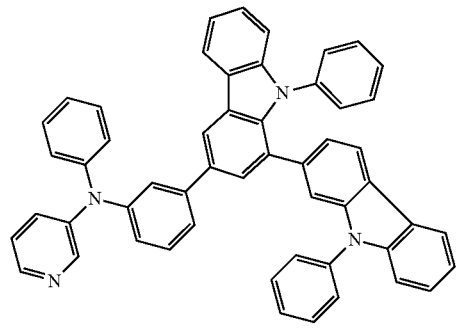
2-24
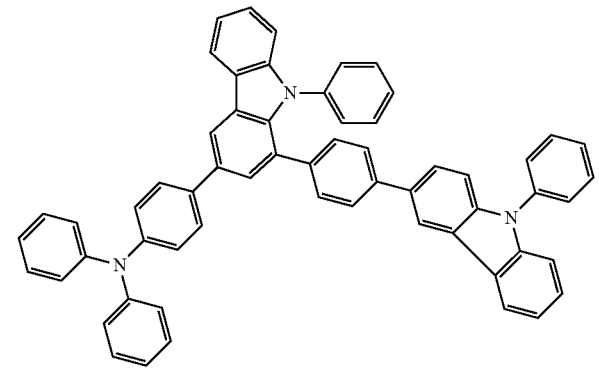
2-25
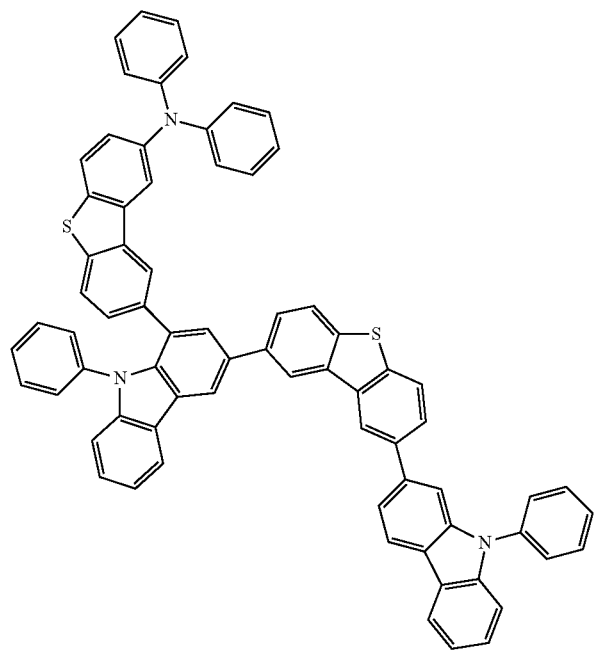
2-26
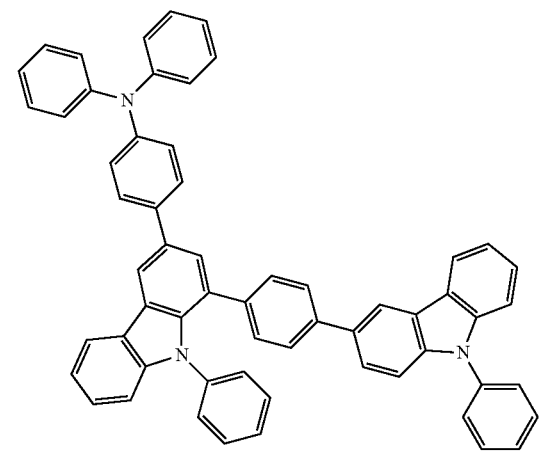

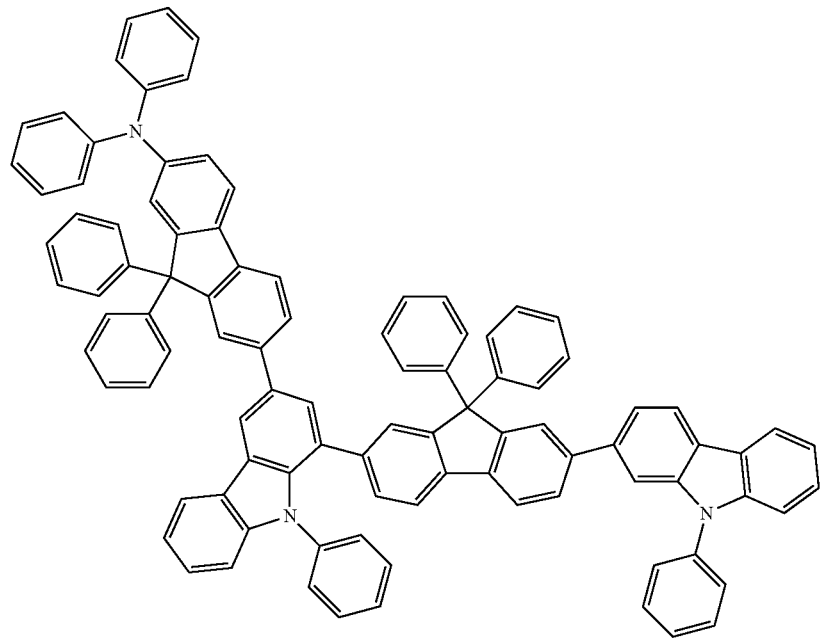
2-27
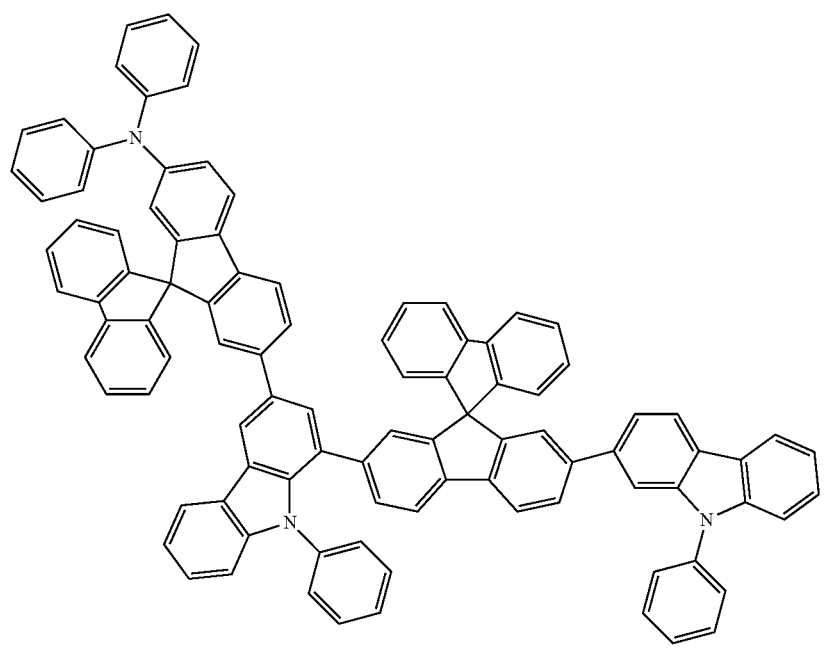
2-28
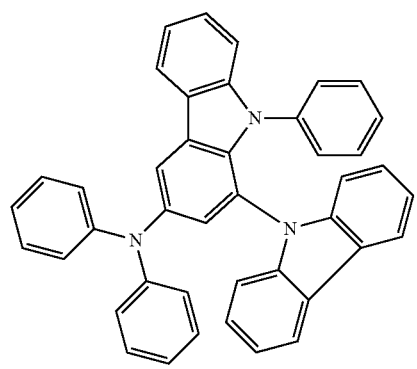
3-1
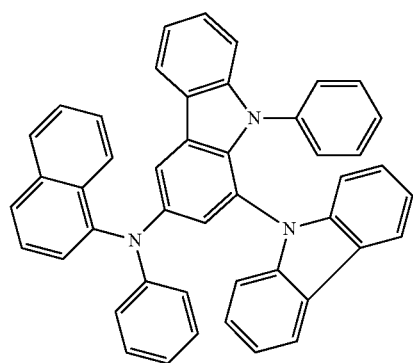
3-2

-continued
3-3
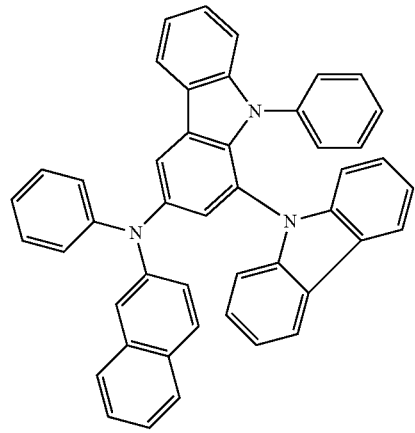
3-4
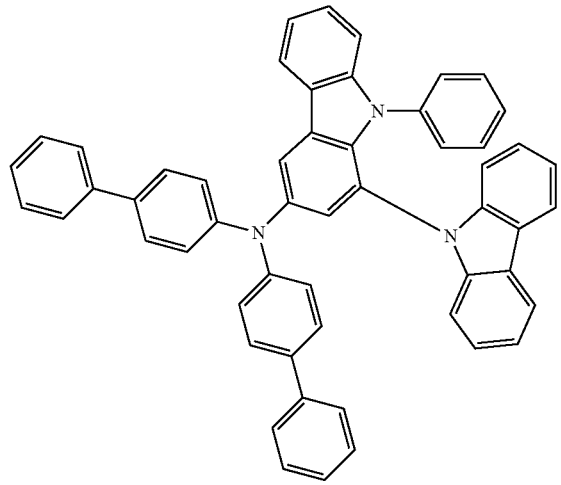
3-5
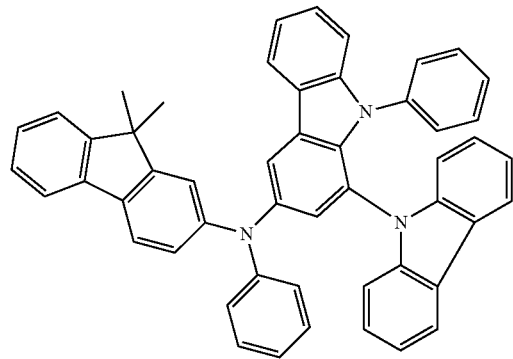
3-6
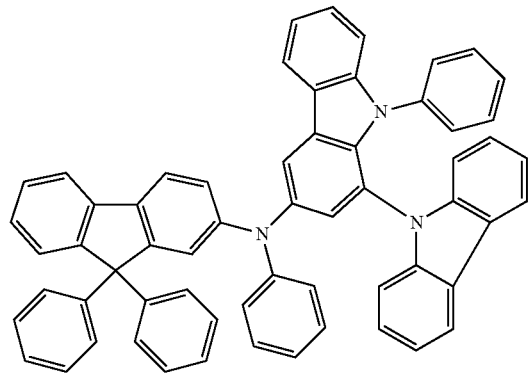
3-7
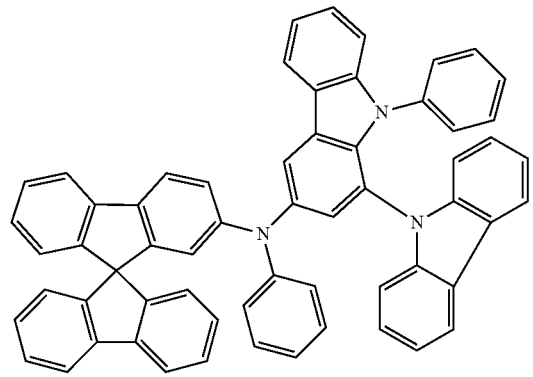
3-8
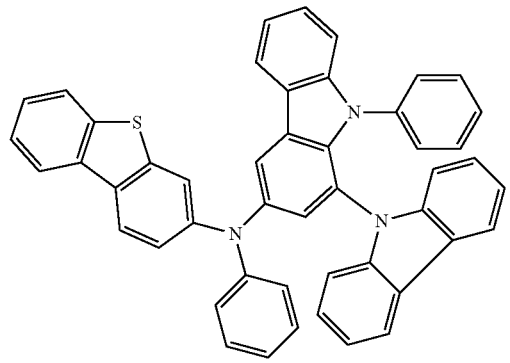

3-9
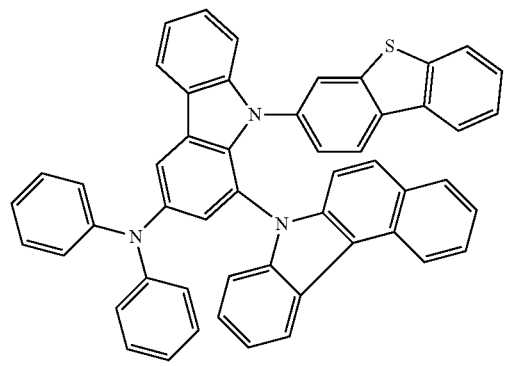
3-10
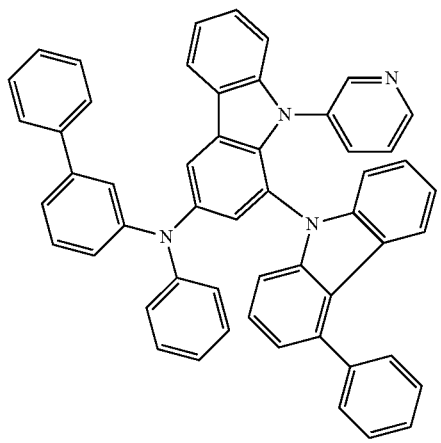
3-11
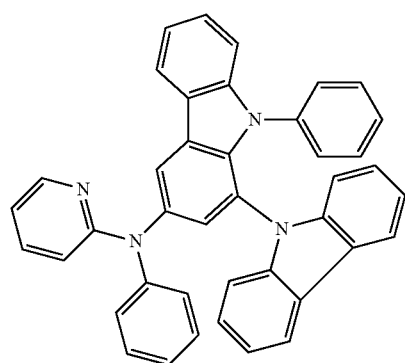
3-12
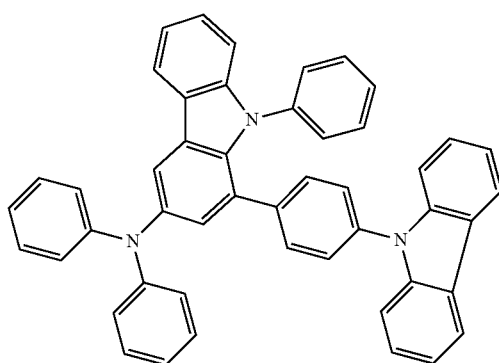
3-13
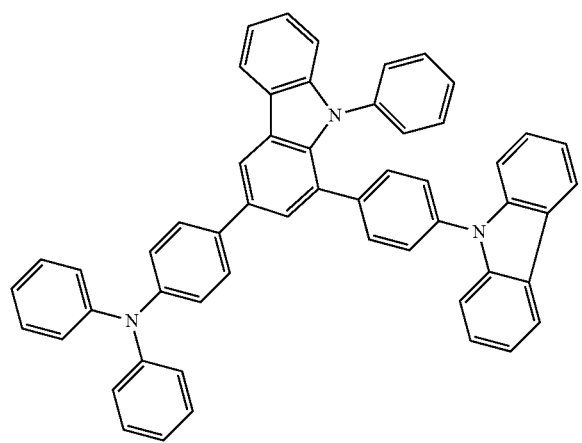
3-14
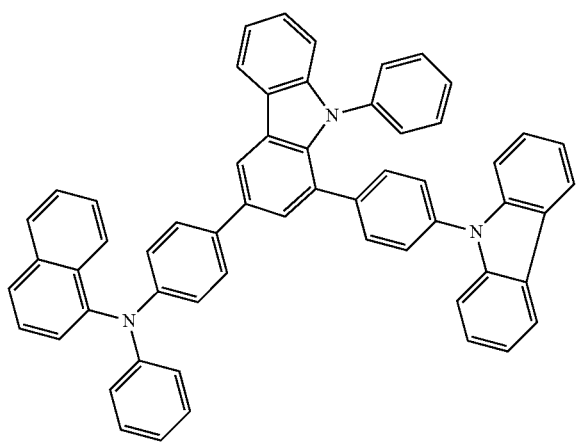

3-15
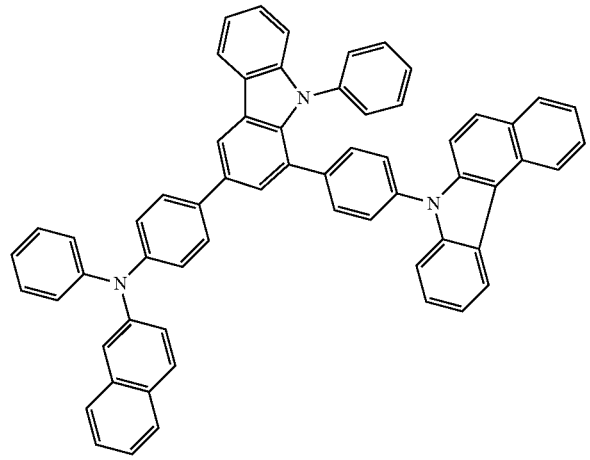
3-16
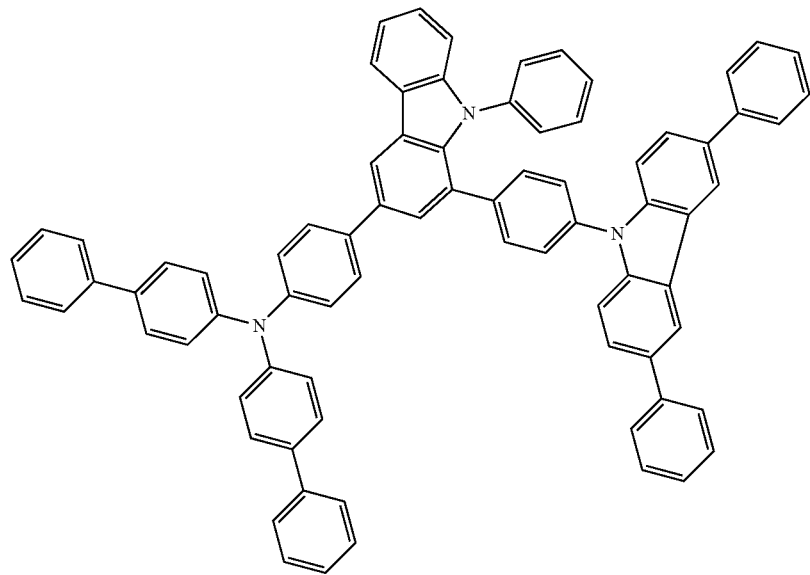
3-17
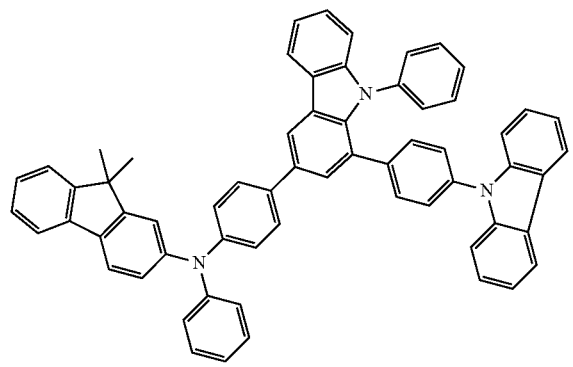
3-18
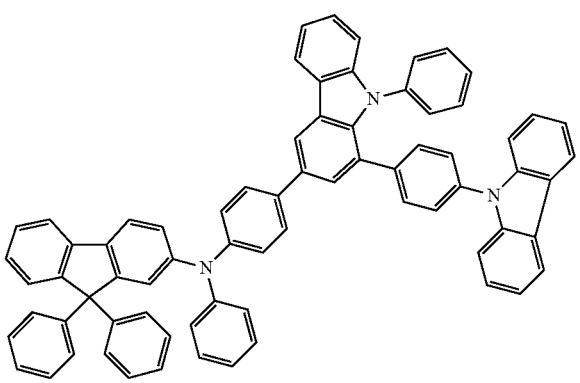

-continued
3-19
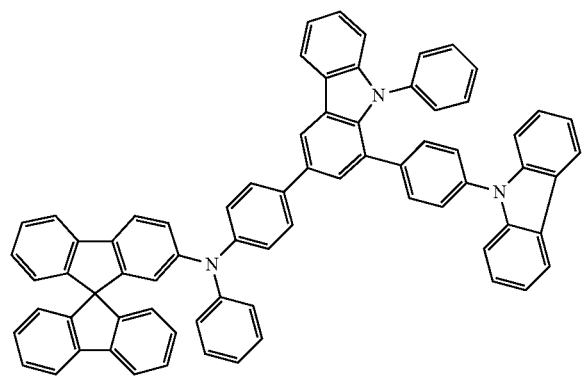
3-20
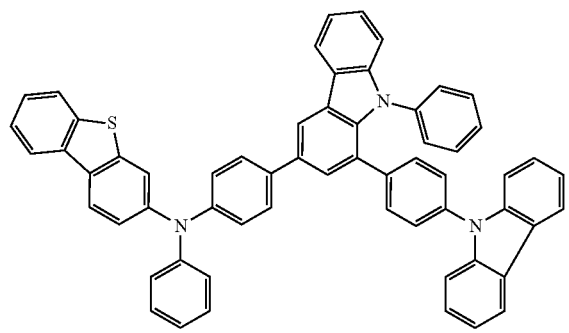
3-21
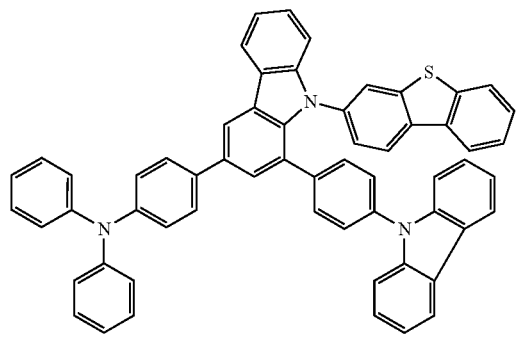
3-22
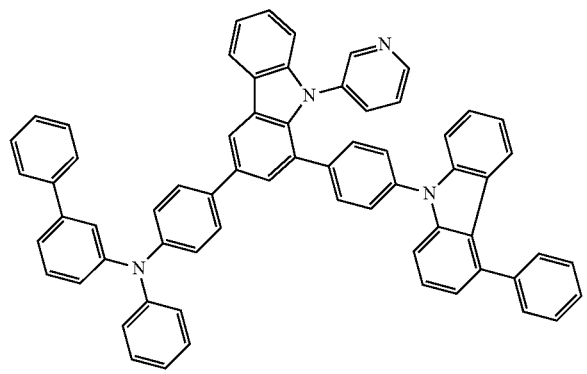
3-23
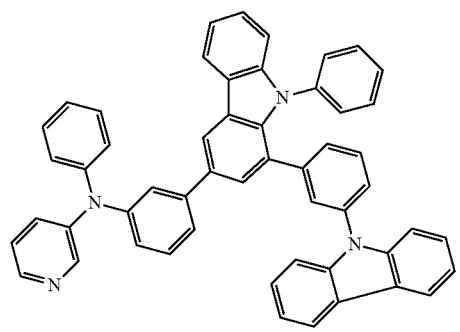
3-24
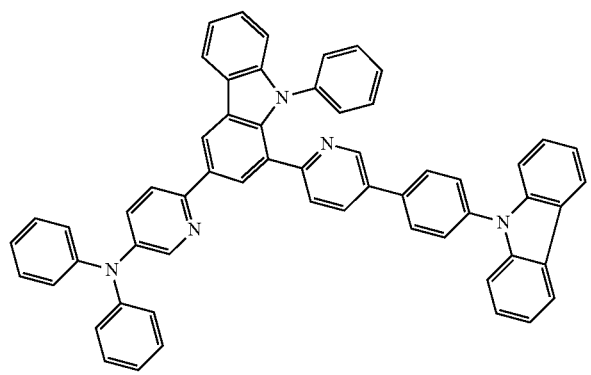

-continued
3-25
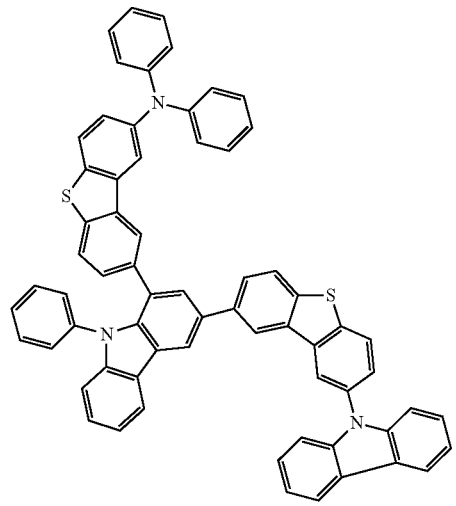
3-26
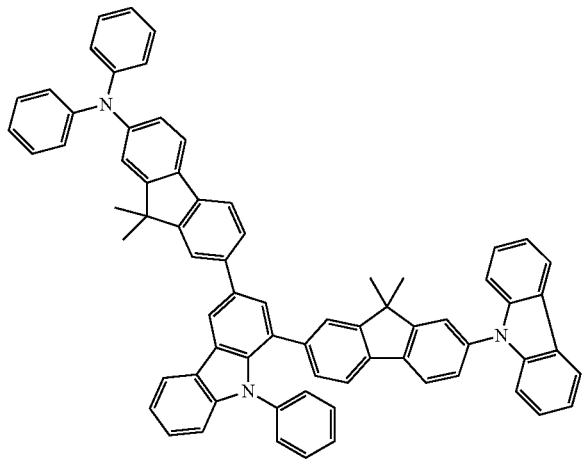
3-27
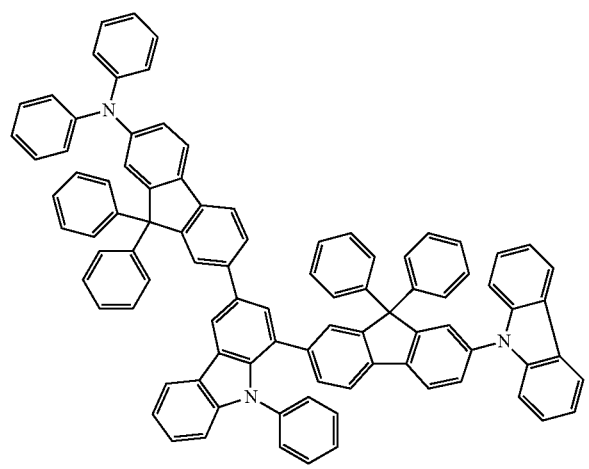
3-28
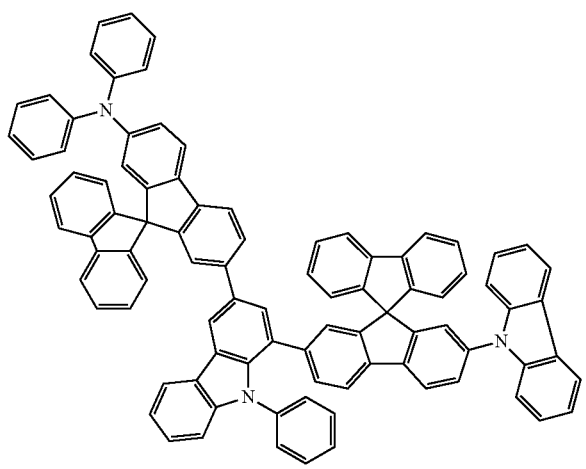
4-1
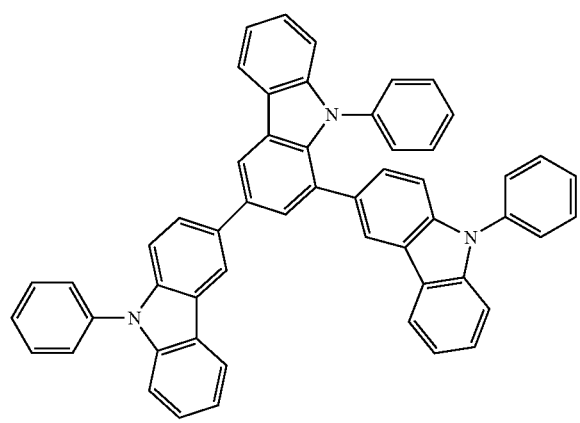
4-2
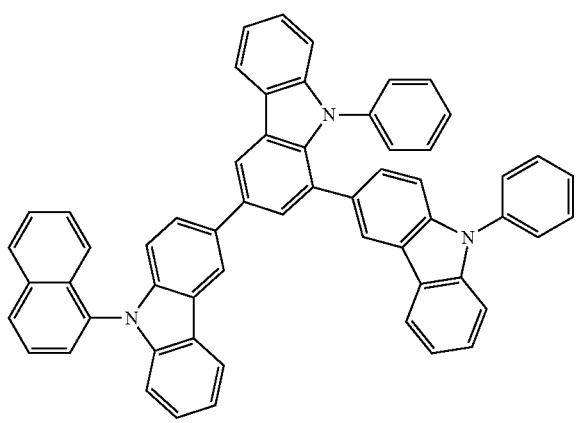

-continued
4-3
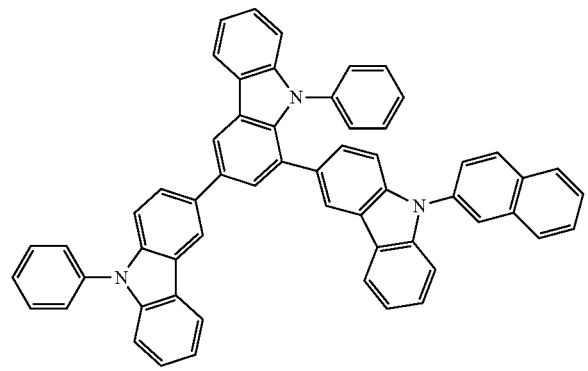
4-4
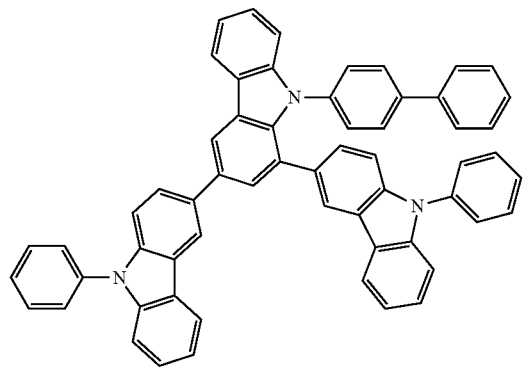
4-5
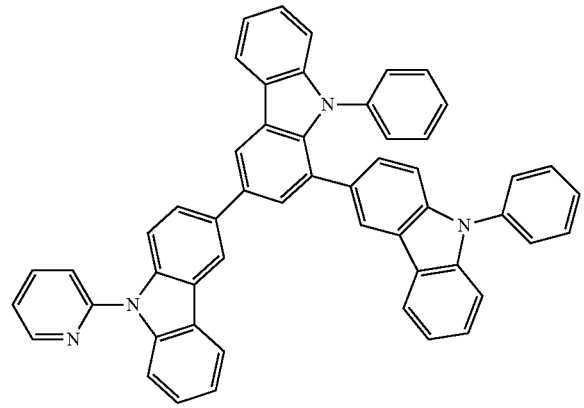
4-6
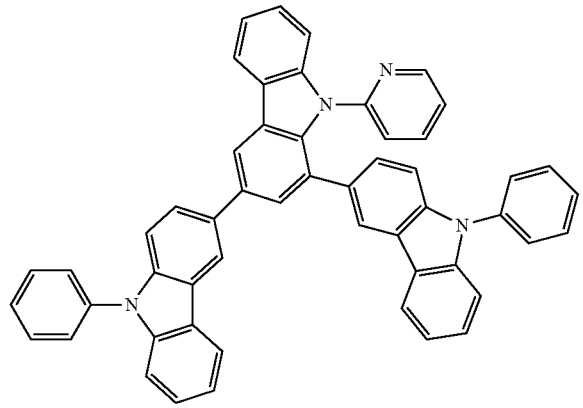
4-7
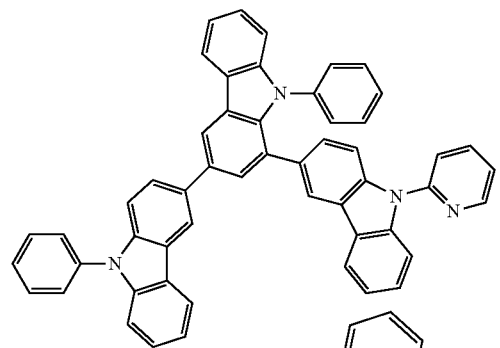
4-8
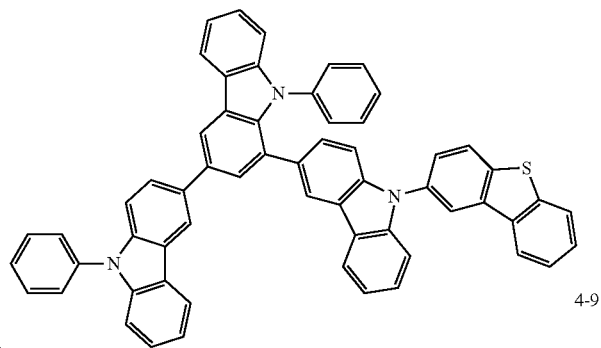
4-9
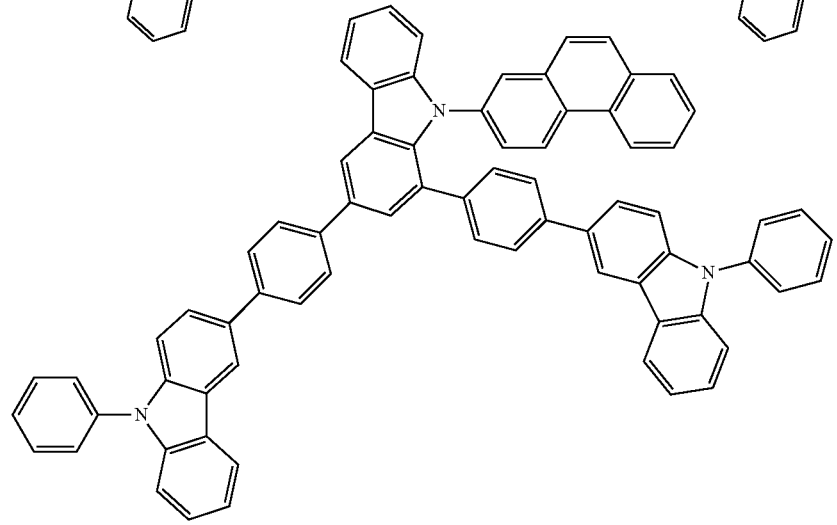

-continued
4-10
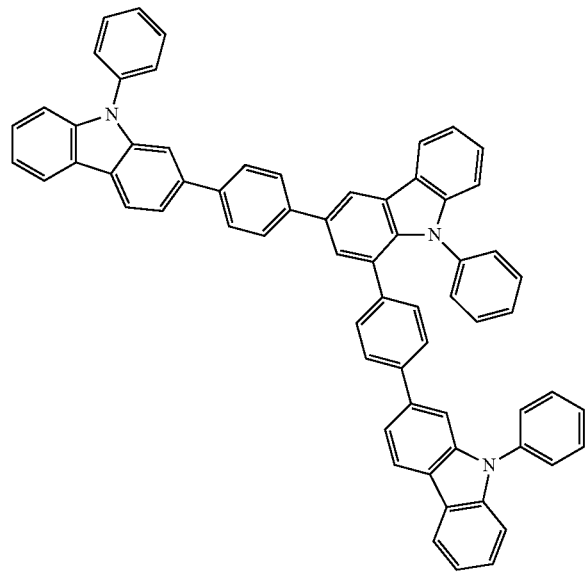
4-11
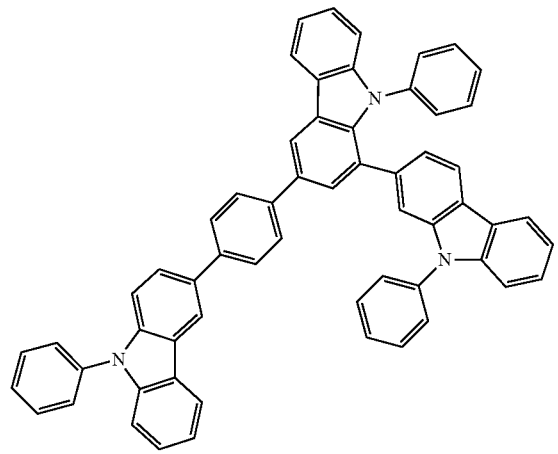
4-12
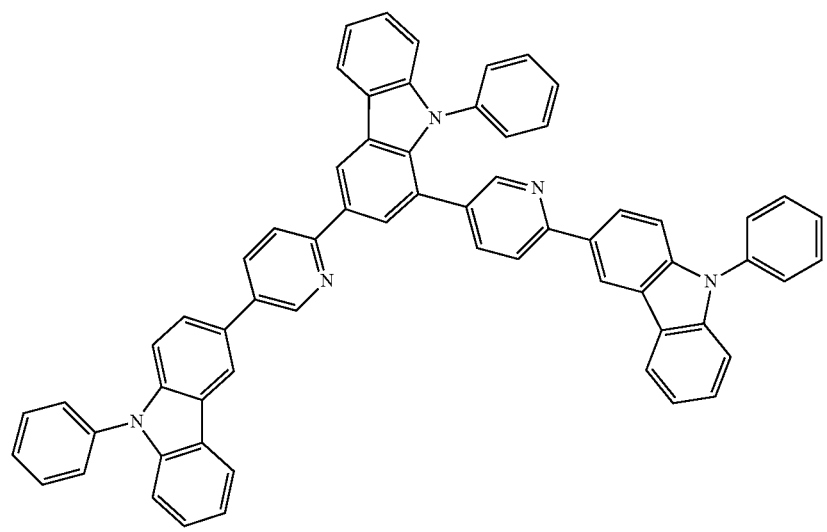
4-13
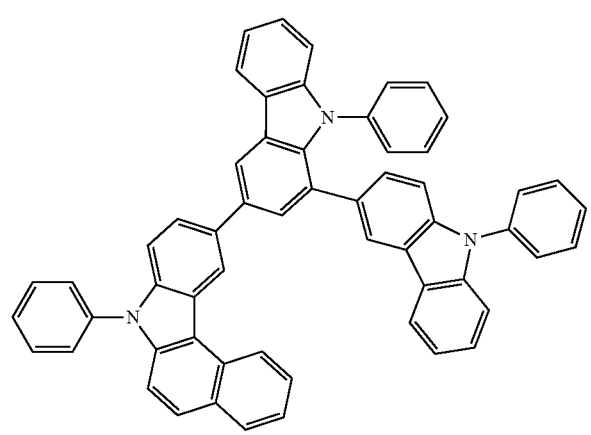
4-14
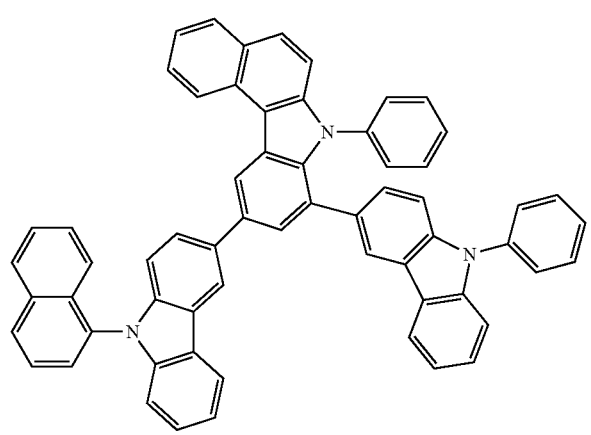

4-15
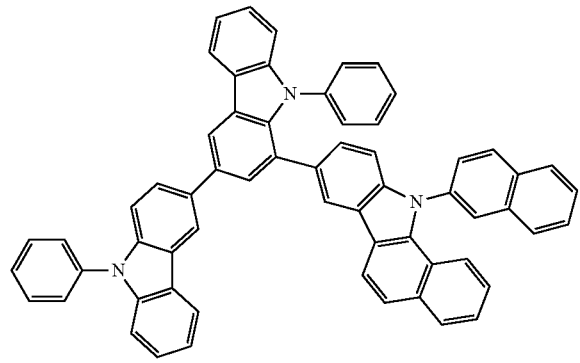
4-16
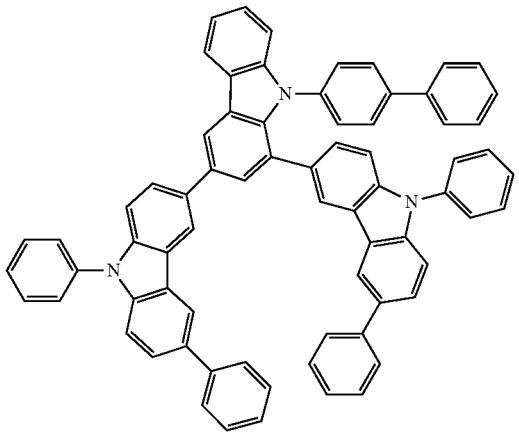
5-1
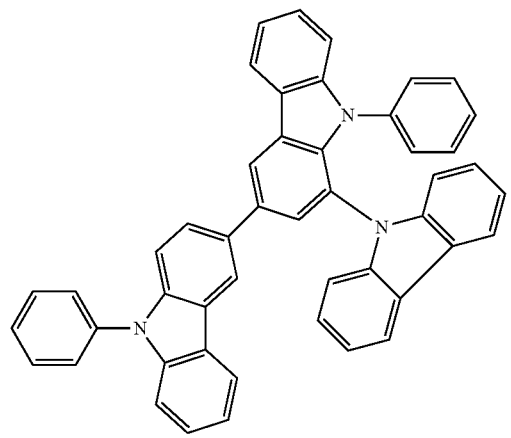
5-2
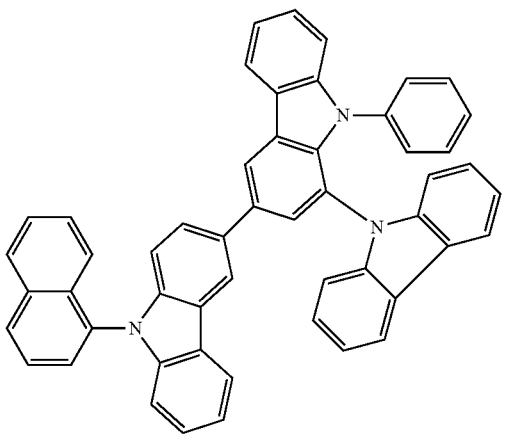
5-3
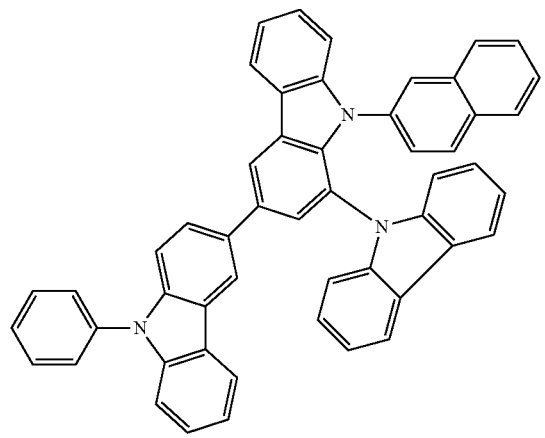
5-4
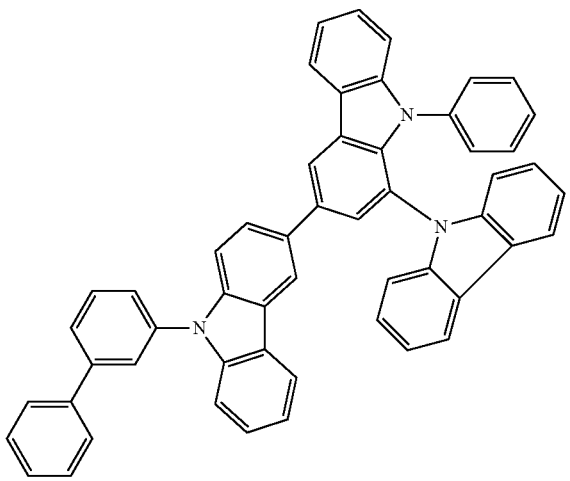

-continued
5-5
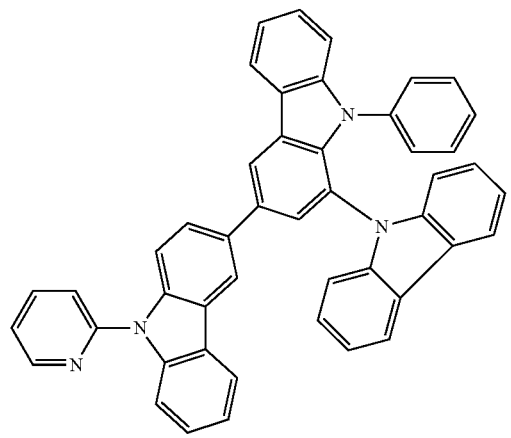
5-6
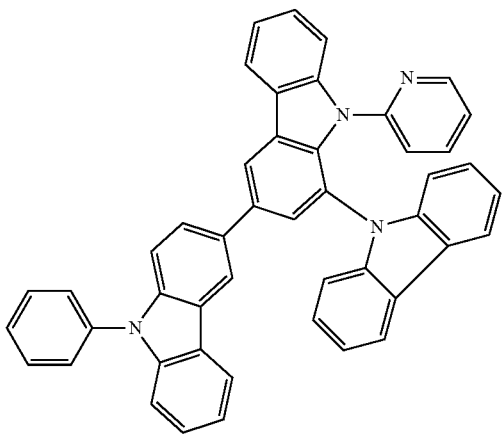
5-7
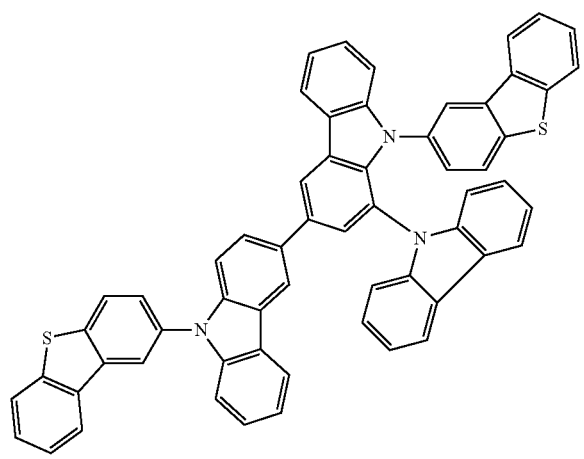
5-8
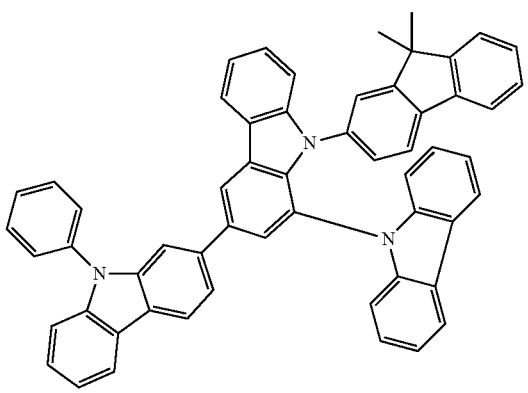
5-9
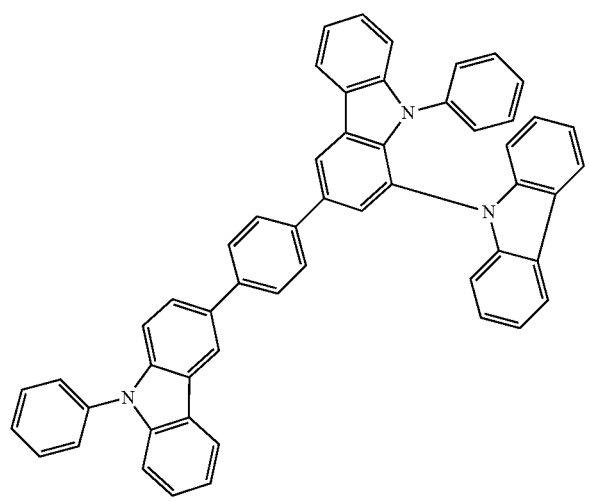
5-10
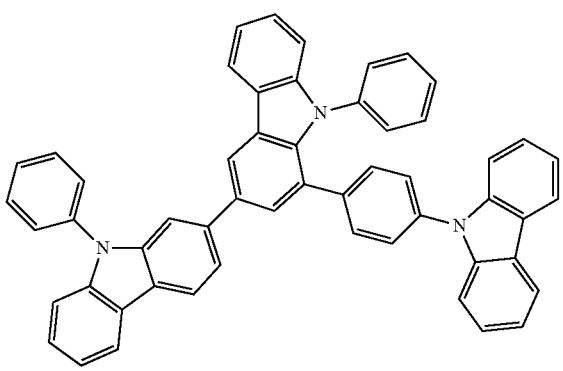

-continued
5-11
5-12
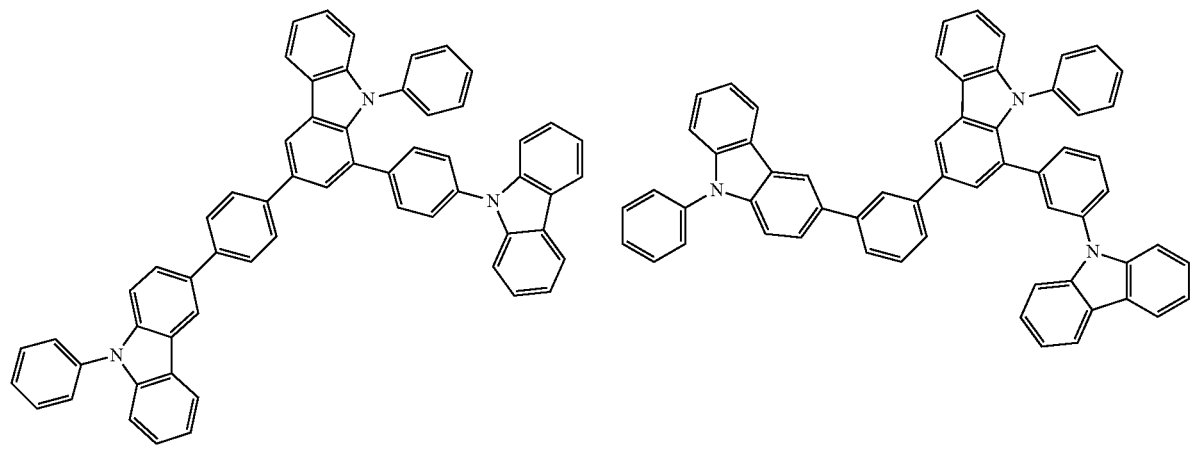
5-13
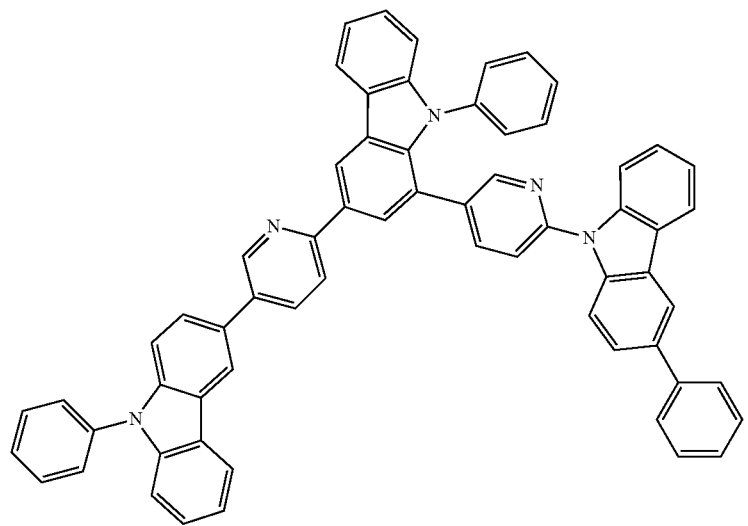
5-14
5-15
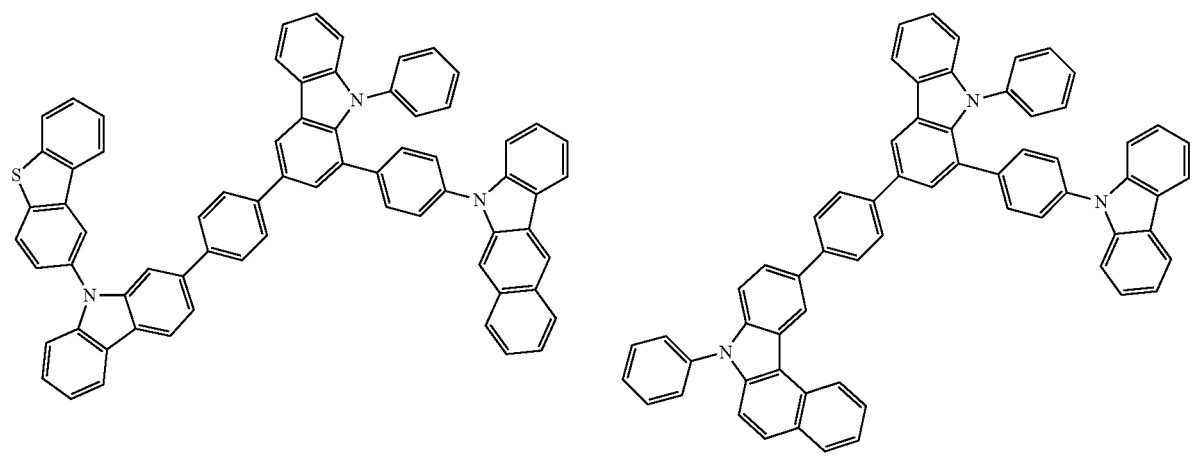

-continued
5-16
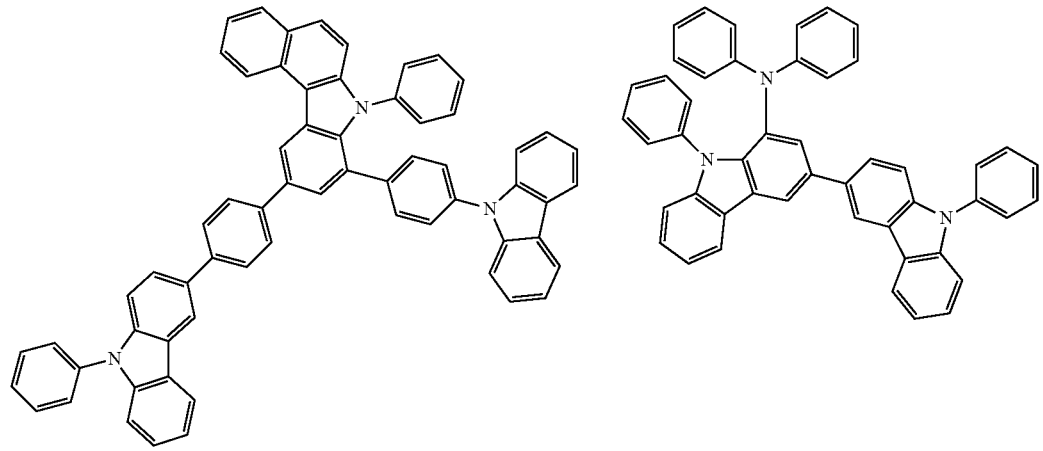
6-1
6-2
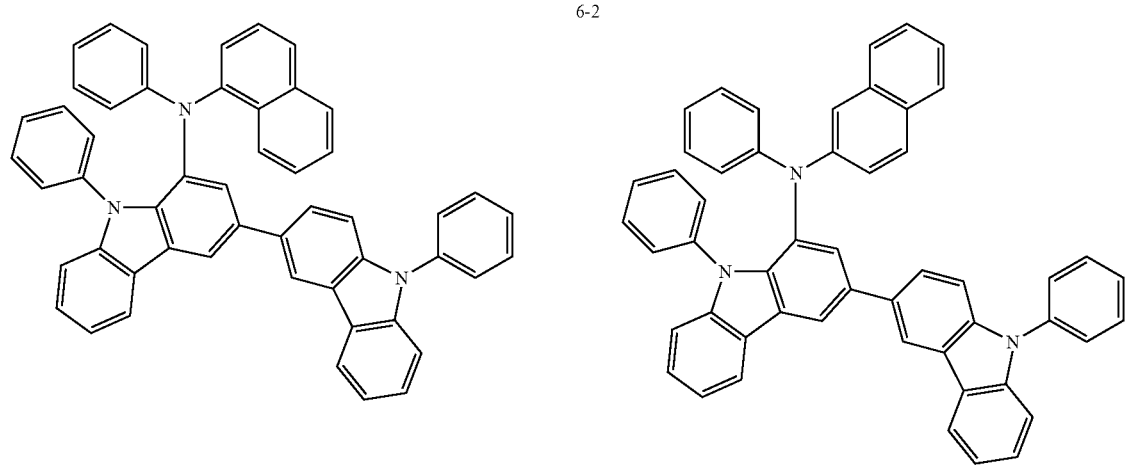
6-3
6-4
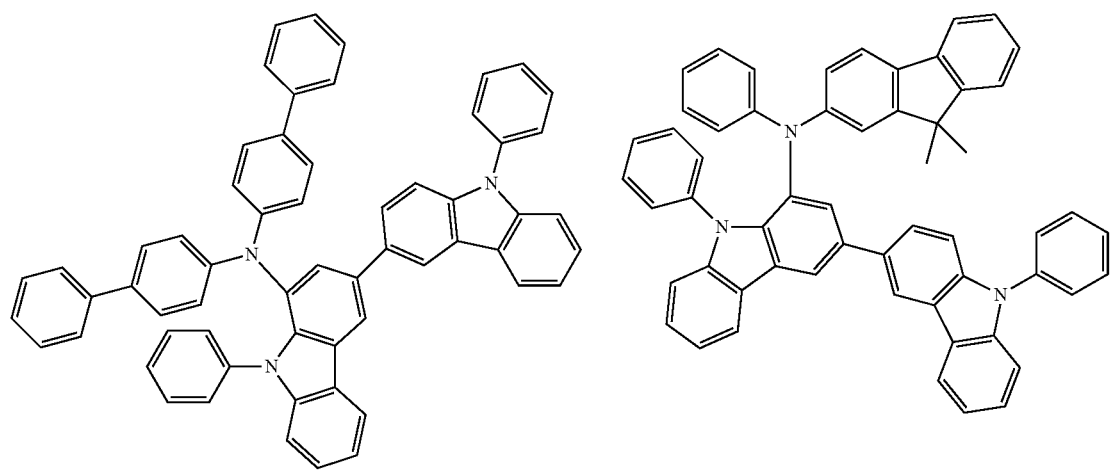
6-5

-continued
6-6
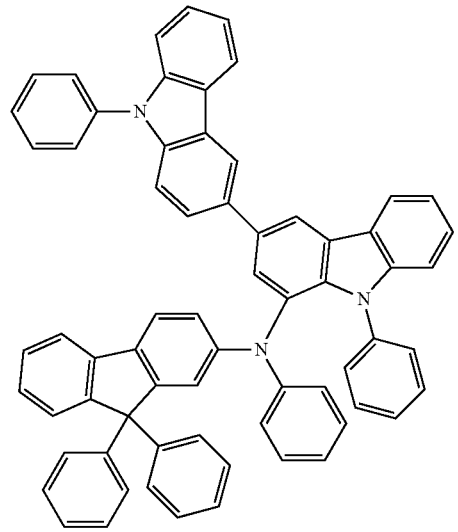
6-7
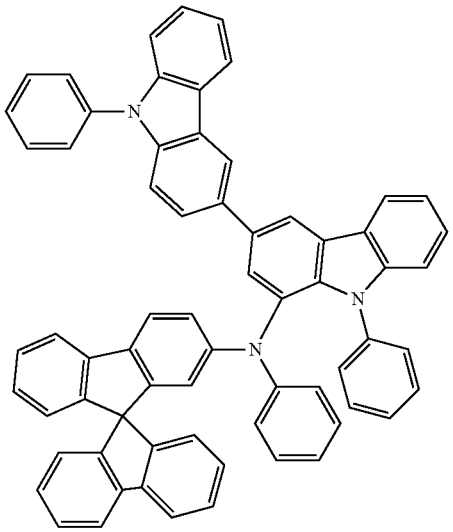
6-8
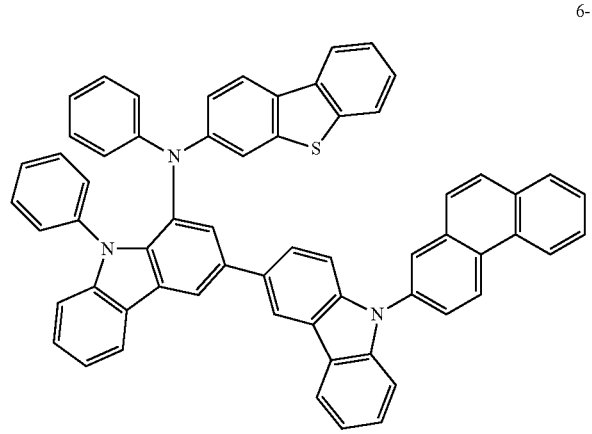
6-9
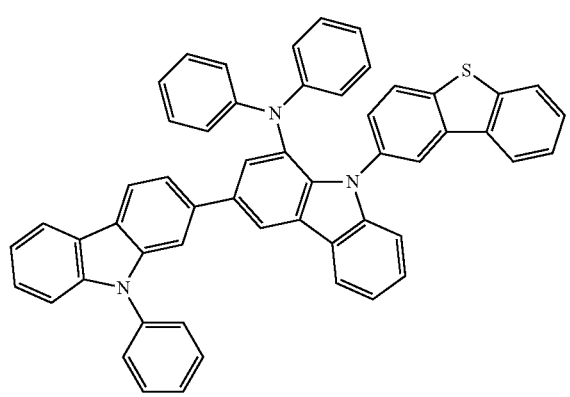
6-10
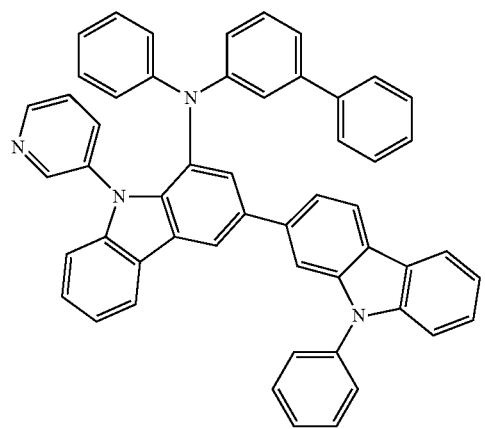
6-11
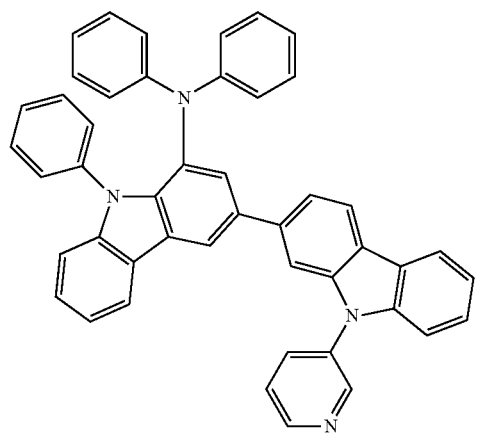

-continued
6-12
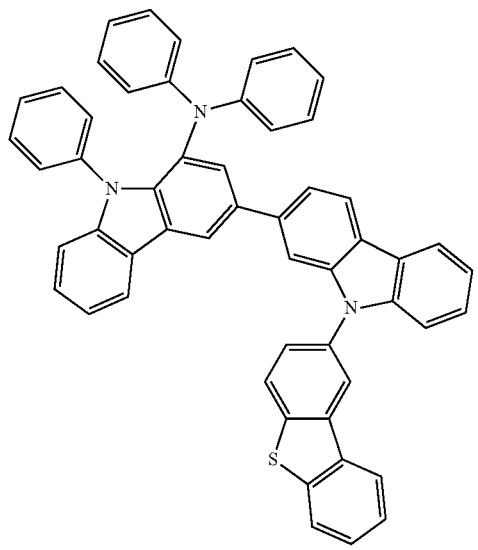
7-1
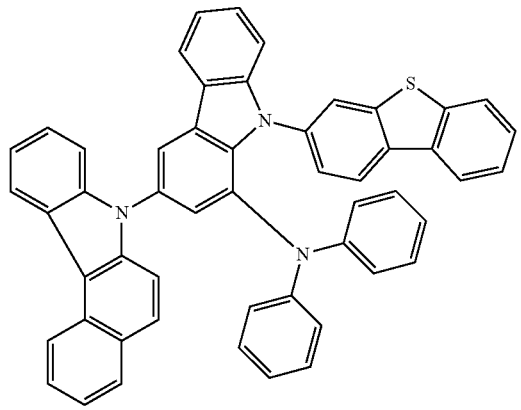
7-2
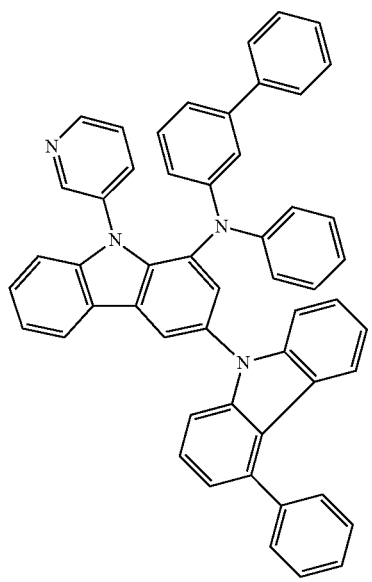
7-3
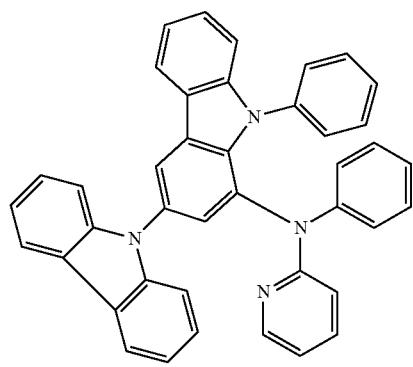
7-4
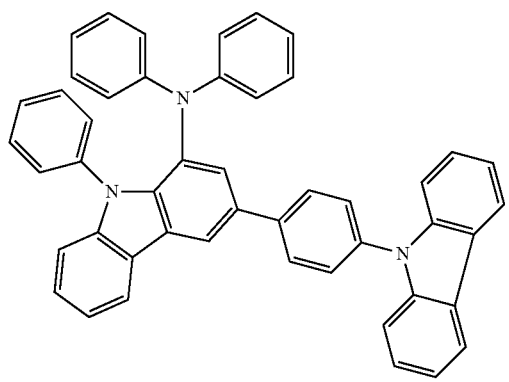
7-5
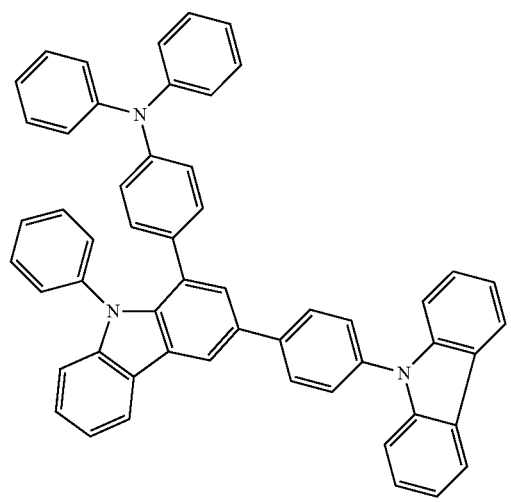

-continued
7-6
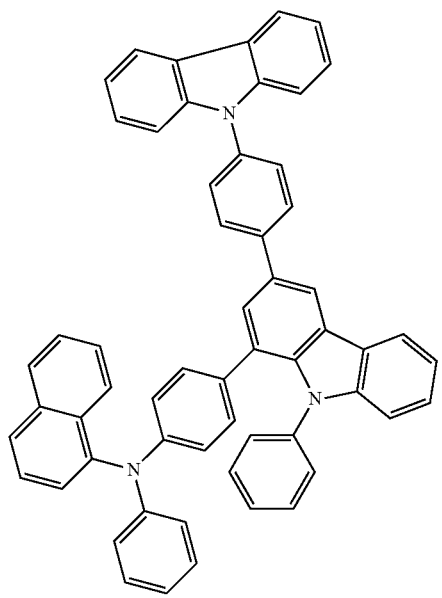
7-7
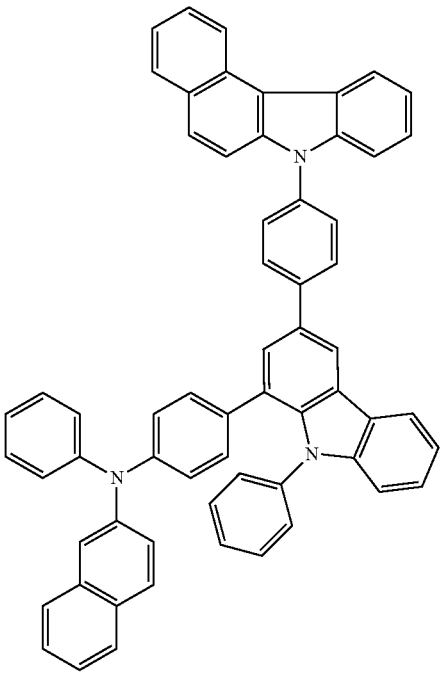
7-8
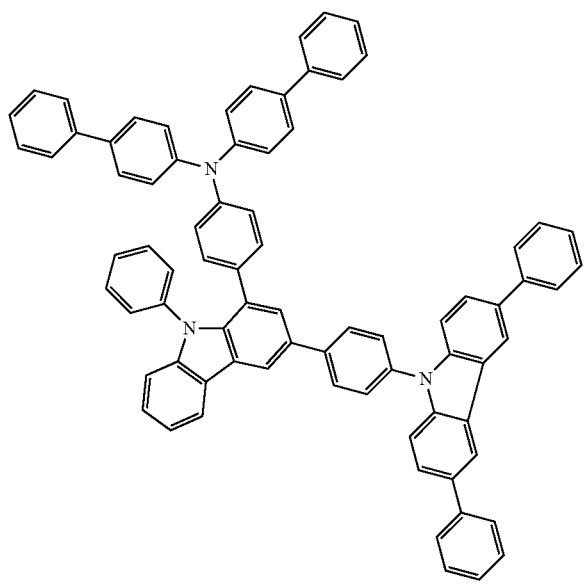
8-1
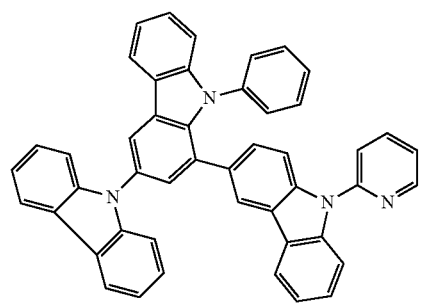
8-2
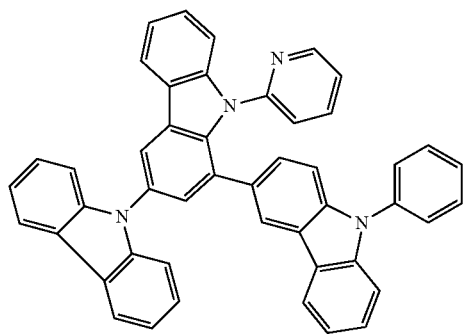
8-3
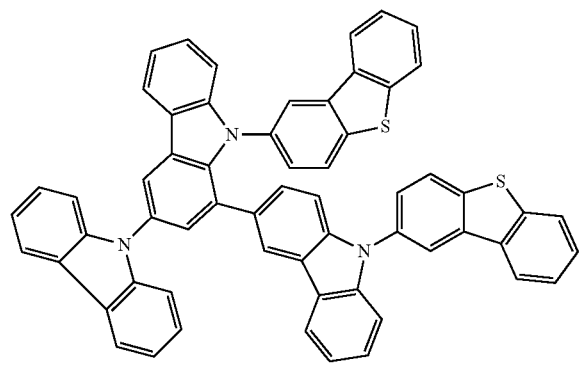

-continued
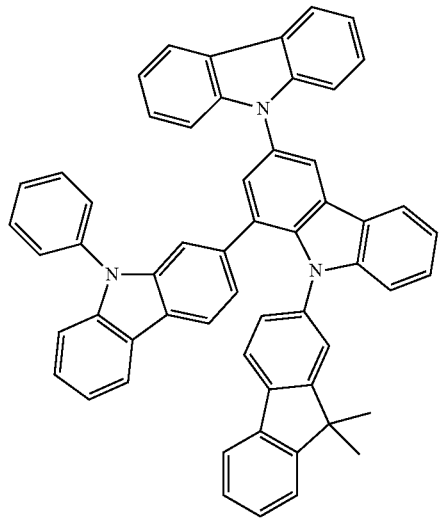
8-4
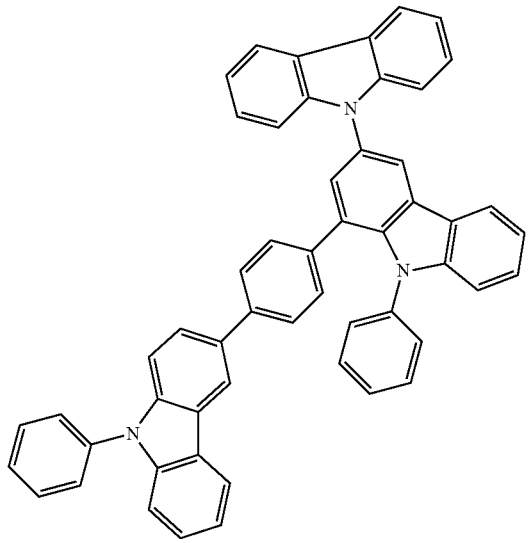
8-5
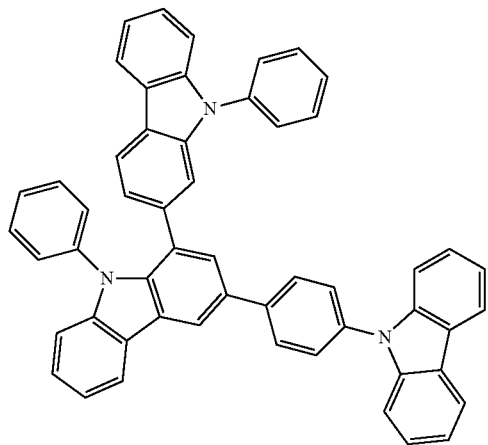
8-6
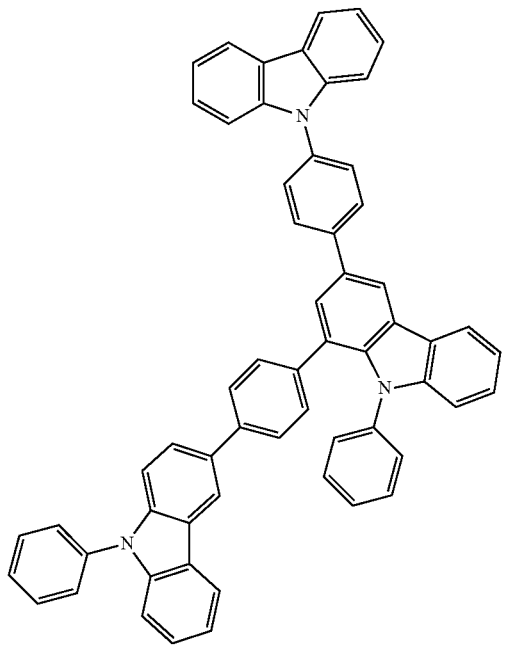
8-7

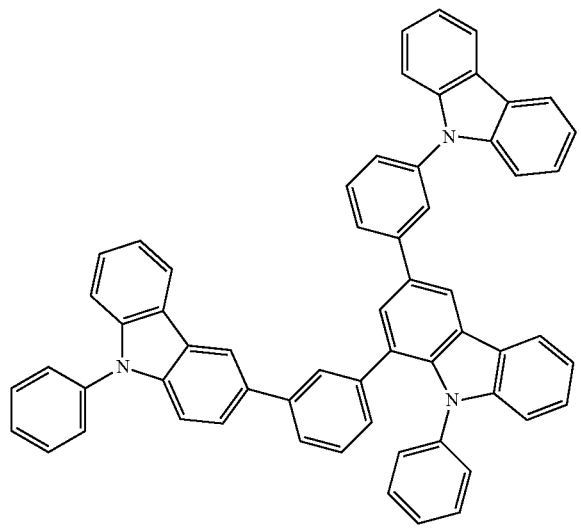

8-8

In another aspect of the present invention, the present invention provides a compound represented by formula 1 for an organic electric element.

In another aspect of the present invention, the present invention provides an organic electric element comprising a compound represented by formula 1.

Here, an organic electric element may comprise a first electrode, a second electrode, and an organic material layer formed between the first electrode and the second electrode, the organic material layer comprises the compound represented by Formula 1, and the compound may be comprised in at least one layer of a hole injection layer, a hole transport layer, an emission-auxiliary layer and a light emitting layer. That is, the compound represented by Formulas 1 may be used as material of a hole injection layer, a hole transport layer, an emission-auxiliary layer or a light emitting layer. Preferably, the compound represented by Formula 1 may be used as an emission-auxiliary layer material.

Preferably, there is provided an organic electric element comprising a compound represented by Formulas 2 to 9 in an organic electric element.

Preferably, there is provided an organic electric element comprising at least one of compounds 1-1 to 1-28, 2-1 to 2-28, 3-1 to 3-28, 4-1 to 4-16, 5-1 to 5-16, 6-1 to 6-12, 7-1 to 7-8, and 8-1 to 8-8 in an organic electric element.

Preferably, the organic electric element may comprise the compound represented by Formula 1 as a single compound or a mixture of two or more kinds. For example, an emission-auxiliary layer of the organic material layer may be formed of a single compound 1-1 or may be formed of a mixture of the compound 1-1 and the compound 1-2.

Meanwhile, the organic material layer may be formed by a spin coating process, a nozzle printing process, an inkjet printing process, a slot coating process, a dip coating process, or a roll-to-roll process.

In another aspect of the present invention, the present invention provides an organic electric element further comprising at least a layer to improve luminous efficiency which is formed on at least one of the sides the first and second electrodes, which is opposite to the organic material layer.

In another aspect of the present invention, the present invention provides an electronic device comprising a display device, wherein a display device comprises an organic electric element according to the present invention, and a control unit for controlling the display device. Preferably, the organic electric element may be any one of an organic light emitting diode, an organic solar cell, an organic photo conductor, an organic transistor, and an element for monochromatic or white illumination.

Hereinafter, Synthesis method of the compound represented by Formula 1 according to one embodiment of the present invention and Preparation method of an organic electric element will be described in detail by way of examples. However, the present invention is not limited to the following examples.

SYNTHESIS EXAMPLE

The compound (final products) represented by Formula 1 according to the present invention are synthesized by reacting Sub 1 and Sub 2 as shown in Reaction Scheme 1, but are not limited thereto.

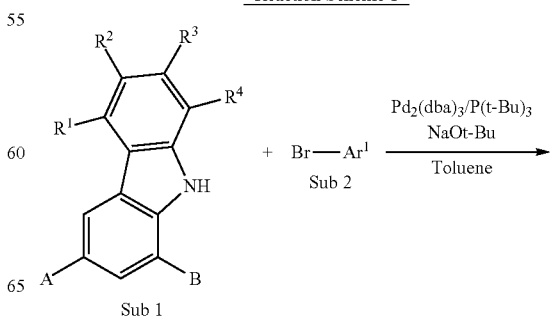

<Reaction Scheme 1>

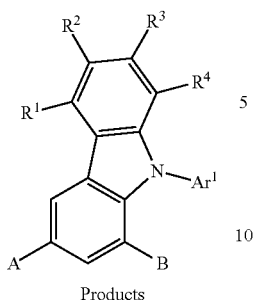

Products

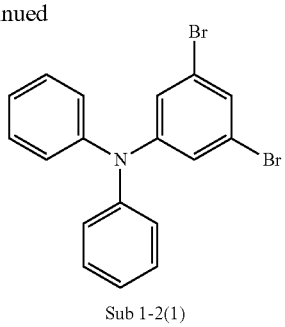

Sub 1-2(1)

I. Synthesis Example of Sub 1

The compound Sub 1 of Reaction Scheme 1 is synthesized by the following Reaction Scheme 2, but is not limited thereto.

<Reaction Scheme 2>

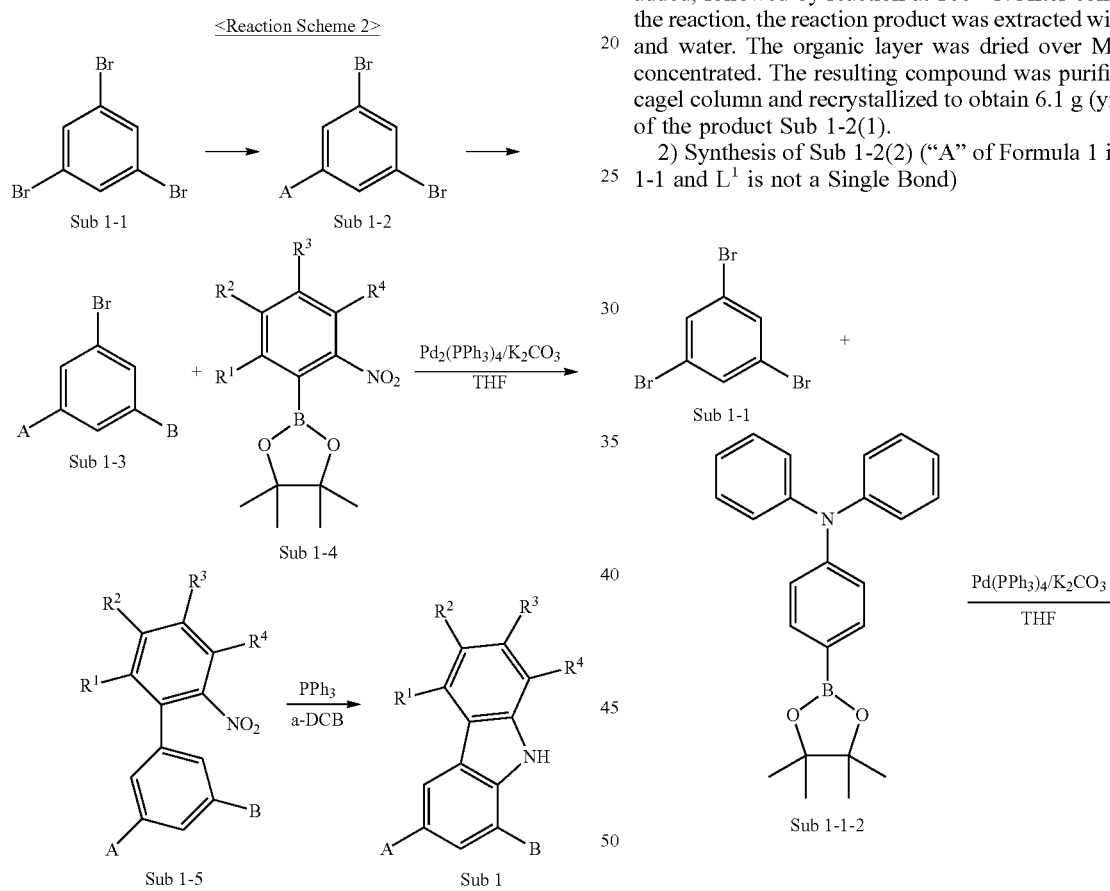

1. Synthesis Example of Sub 1-2
1) Synthesis of Sub 1-2(1) ("A" of Formula 1 is Formula 1-1 and $L^1$ is a Single Bond)

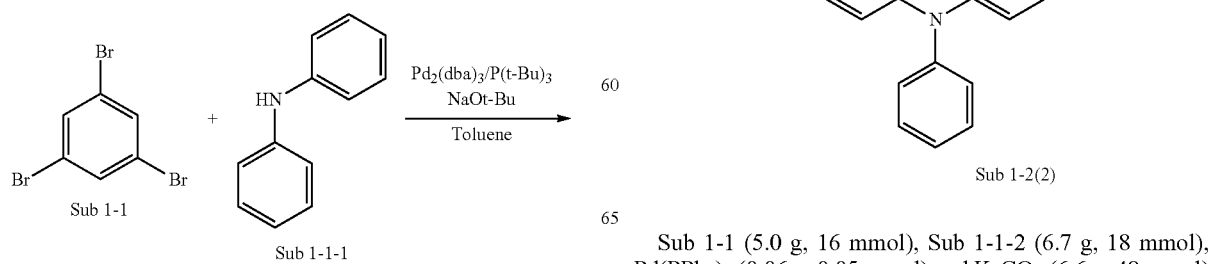

Sub 1-1 (6.3 g, 20 mmol), Sub 1-1-1 (3.4 g, 20 mmol), $Pd_2(dba)_3$ (0.5 g, 0.6 mmol), $P(t-Bu)_3$ (0.2 g, 2 mmol), t-BuONa (5.8 g, 60 mmol) and toluene (300 mL) were added, followed by reaction at 100° C. After completion of the reaction, the reaction product was extracted with $CH_2Cl_2$ and water. The organic layer was dried over $MgSO_4$ and concentrated. The resulting compound was purified by silicagel column and recrystallized to obtain 6.1 g (yield: 76%) of the product Sub 1-2(1).

2) Synthesis of Sub 1-2(2) ("A" of Formula 1 is Formula 1-1 and $L^1$ is not a Single Bond)

Sub 1-1 (5.0 g, 16 mmol), Sub 1-1-2 (6.7 g, 18 mmol), $Pd(PPh_3)_4$ (0.06 g, 0.05 mmol) and $K_2CO_3$ (6.6 g, 48 mmol)

were dissolved in anhydrous THF and a small amount of water, and refluxed for 24 hours. When the reaction was completed, the reactant was cooled to room temperature, extracted with CH$_2$Cl$_2$ and washed with water. A small amount of water from the washed product was removed with anhydrous MgSO$_4$. After filtration under reduced pressure, the organic solvent was concentrated, and the resulting product was separated by column chromatography to obtain 5.6 g (yield: 74%) of the product Sub 1-2(2).

3) Synthesis of Sub 1-2(3) ("A" of Formula 1 is Formula 1-2)

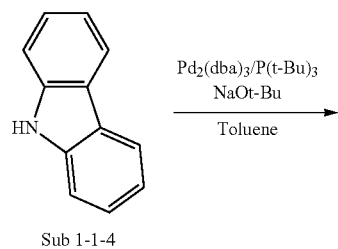

Sub 1-1-4

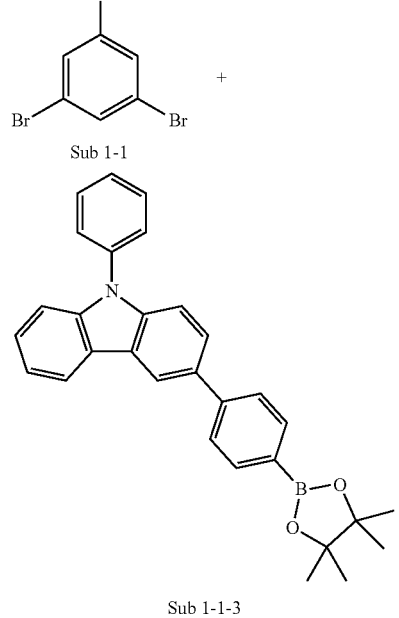

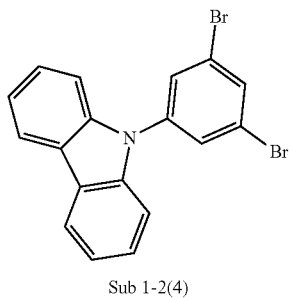

Sub 1-2(4)

Sub 1-1 (6.3 g, 20 mmol), Sub 1-1-4 (3.3 g, 20 mmol), Pd$_2$(dba)$_3$ (0.5 g, 0.6 mmol), P(t-Bu)$_3$ (0.2 g, 2 mmol), t-BuONa (5.8 g, 60 mmol), toluene (300 mL) were added, and 6.0 g (yield: 75%) of the product Sub 1-2(4) was obtained by using the same manner as described above for the synthesis of compound Sub 1-2(1).

5) Synthesis of Sub 1-2(5) ("A" of Formula 1 is Formula 1-3 and L$^3$ is Not a Single Bond)

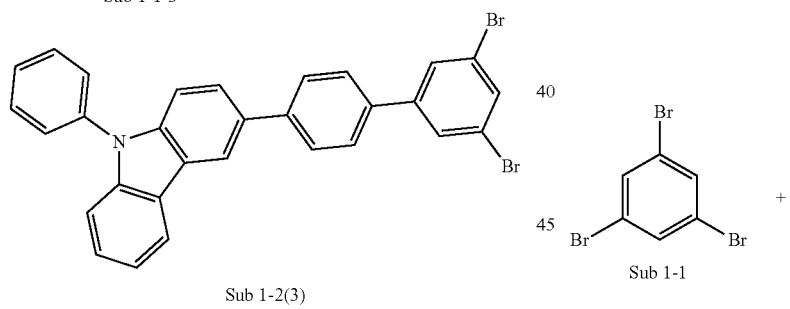

Sub 1-2(3)

Sub 1-1 (5.0 g, 16 mmol), Sub 1-1-3 (8.0 g, 18 mmol), Pd(PPh$_3$)$_4$ (0.06 g, 0.05 mmol) and K$_2$CO$_3$ (6.6 g, 48 mmol) were dissolved in anhydrous THF and a small amount water, and 6.3 g (yield: 71%) of the product Sub 1-2(3) was obtained by using the same manner as described above for the synthesis of compound Sub 1-2(2).

4) Synthesis of Sub 1-2(4) ("A" of Formula 1 is Formula 1 and L$^3$ is a Single Bond)

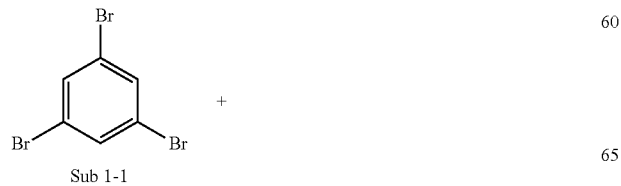

Sub 1-1

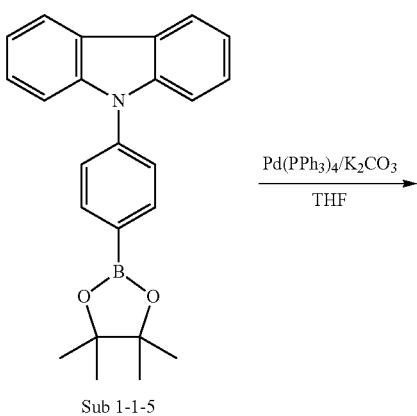

Sub 1-1-5

-continued

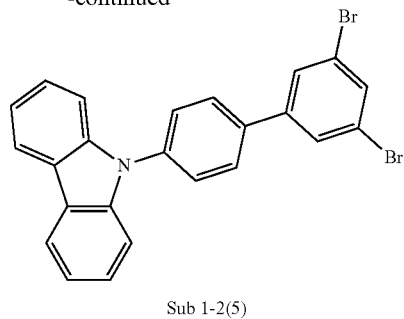

Sub 1-2(5)

Sub 1-1 (5.0 g, 16 mmol), Sub 1-1-5 (6.6 g, 18 mmol), Pd(PPb$_3$)$_4$ (0.06 g, 0.05 mmol), K$_2$CO$_3$ (6.6 g, 48 mmol) were dissolved in anhydrous THF and a small amount water, and 5.5 g (yield: 72%) of the product Sub 1-2(5) was obtained by using the same manner as described above for the synthesis of compound Sub 1-2(2).

2. Synthesis Example of Sub 1-3

Sub 1-3 can be synthesized by using the synthesis methods of Sub 1-2(1) and Sub 1-2(2) when "B" in formula 1 is the formula 1-1, by using the synthesis method of Sub 1-2(3) when "B" in formula 1 is the formula 1-2, and by using the synthesis methods of Sub 1-2(4) and Sub 1-2(5) when "B" in formula 1 is the formula 1-3.

Meanwhile, examples of Sub 1-3 are as followings, but are not limited to, and Table 1 below shows the FD-MS values thereof.

Sub 1-3(1)

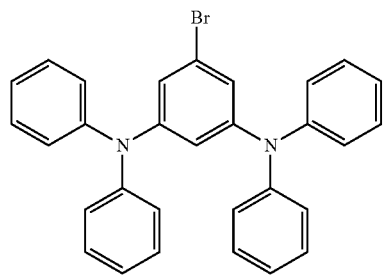

Sub 1-3(2)

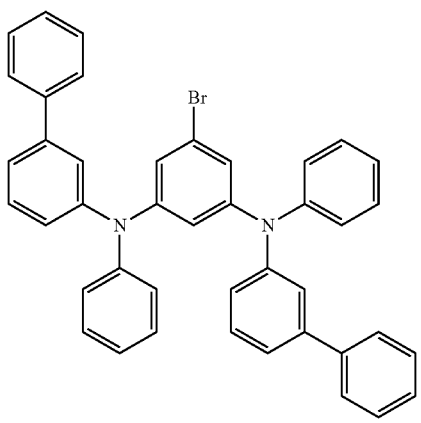

Sub 1-3(3)

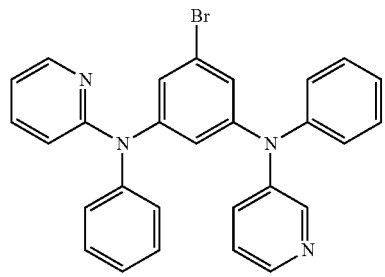

Sub 1-3(4)

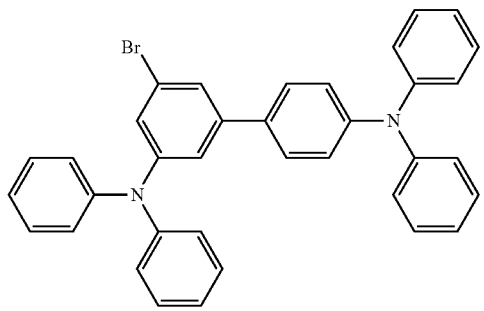

Sub 1-3(5)

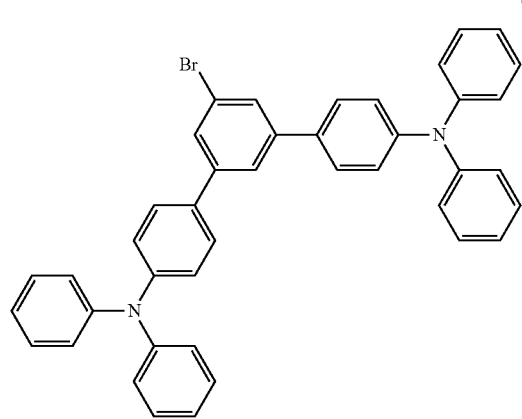

Sub 1-3(6)

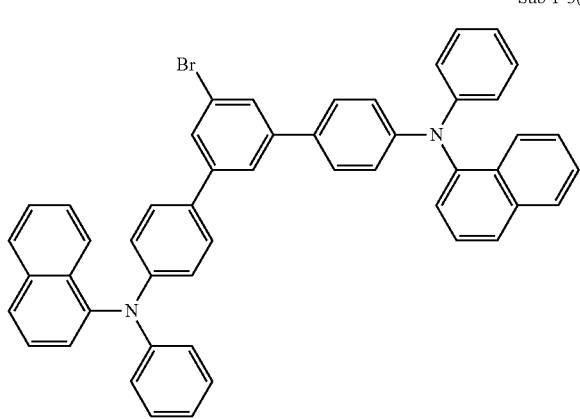

Sub 1-3(7)
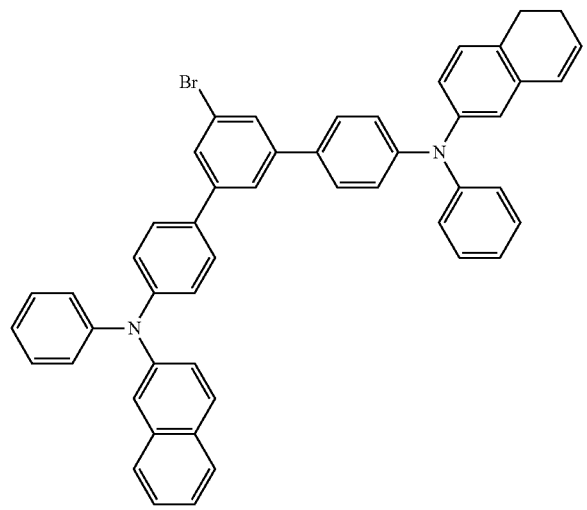
Sub 1-3(8)
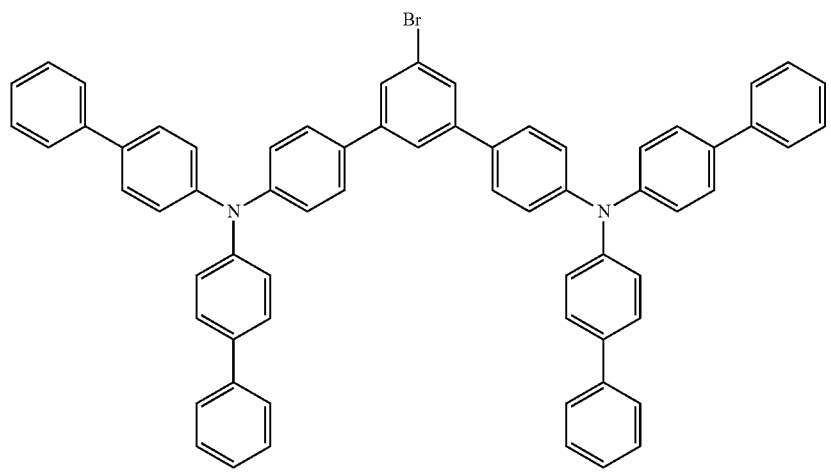
Sub 1-3(9)
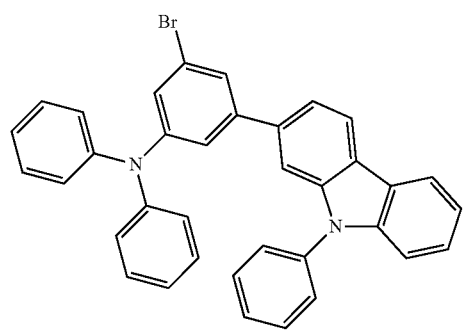
Sub 1-3(10)
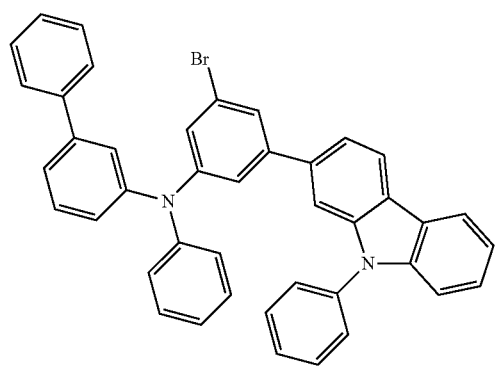

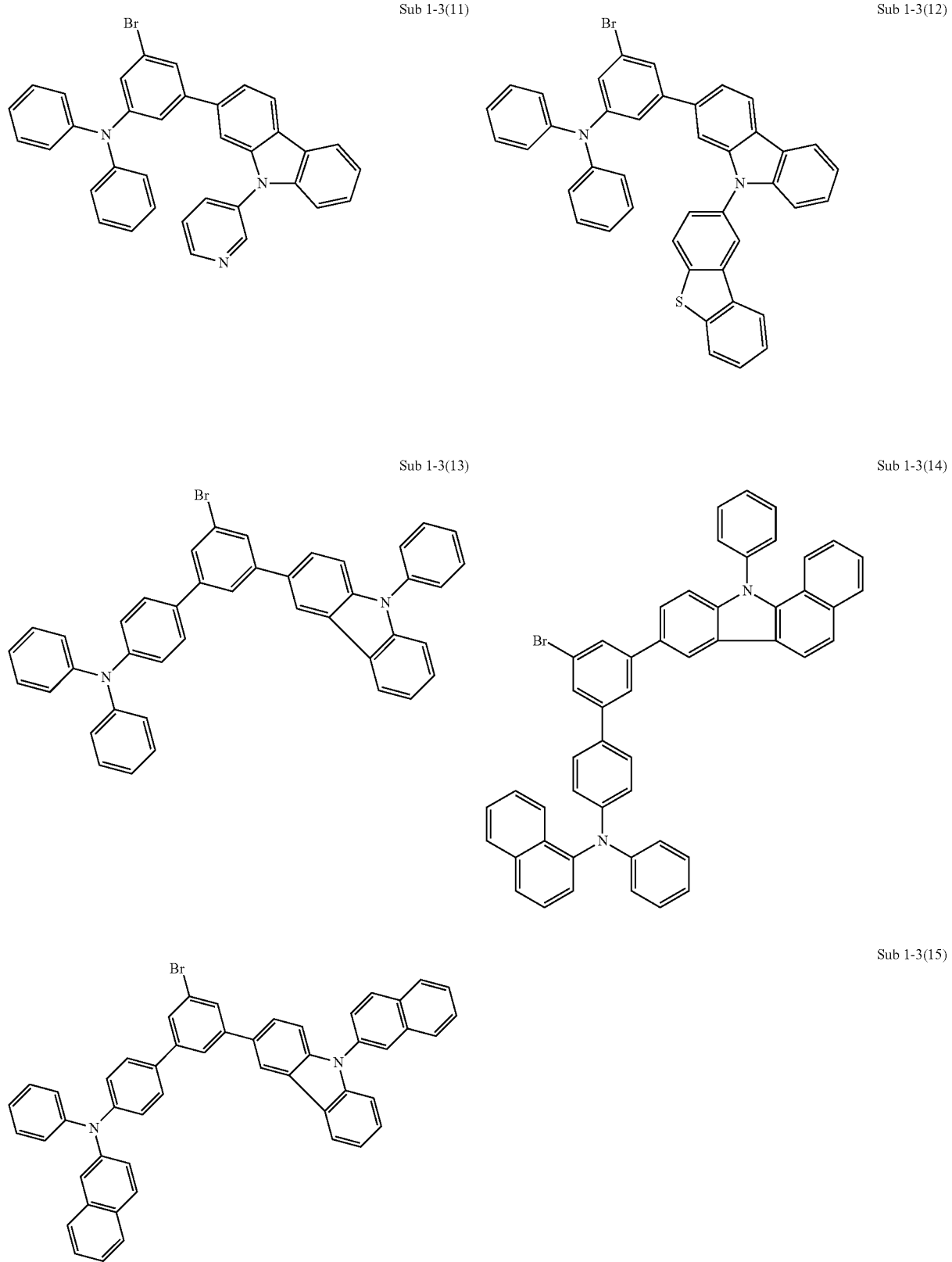

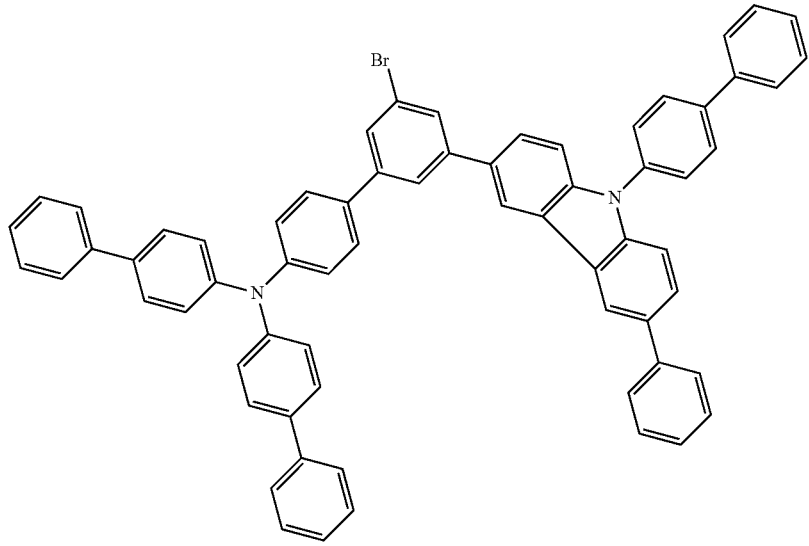
Sub 1-3(16)
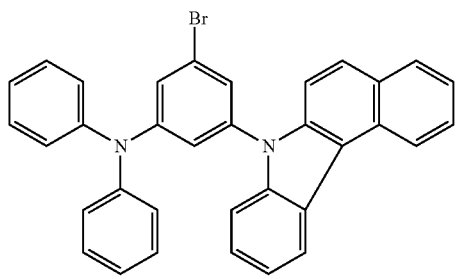
Sub 1-3(17)
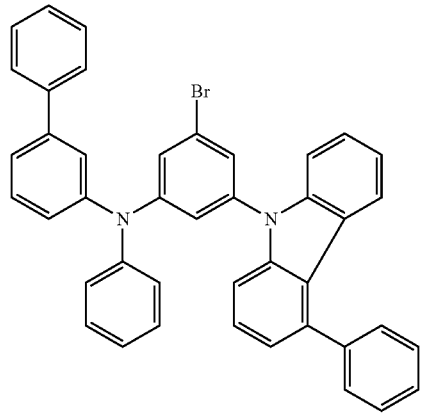
Sub 1-3(18)
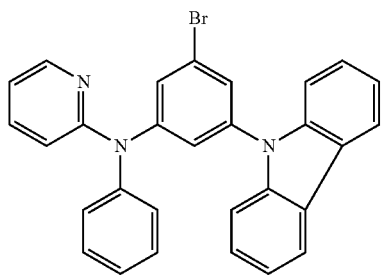
Sub 1-3(19)
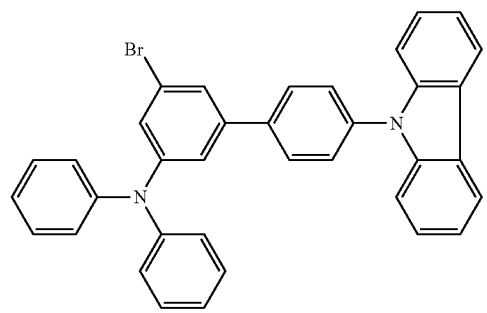
Sub 1-3(20)

-continued
Sub 1-3(21)
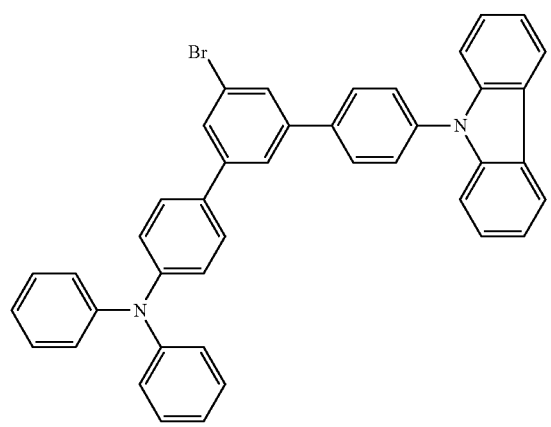
Sub 1-3(22)
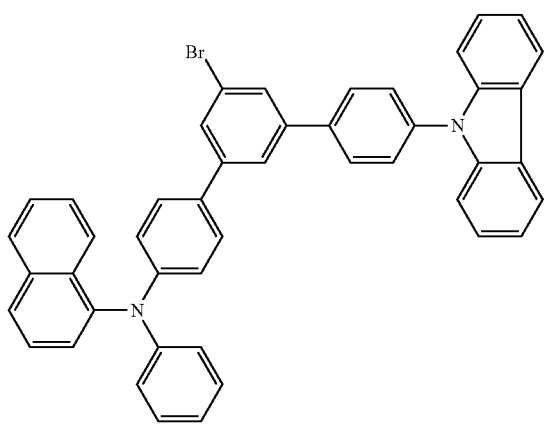
Sub 1-3(23)
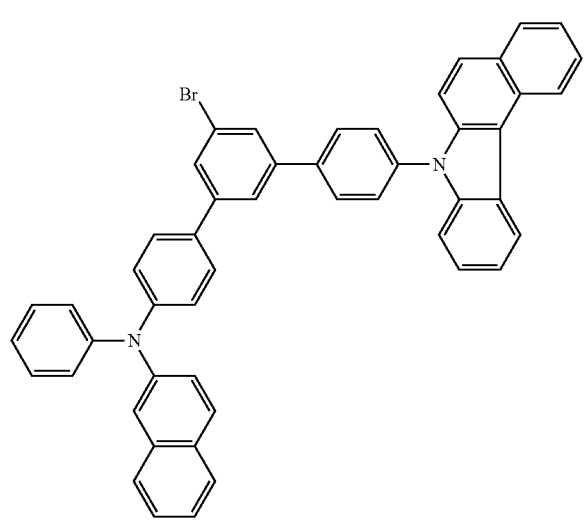
Sub 1-3(24)
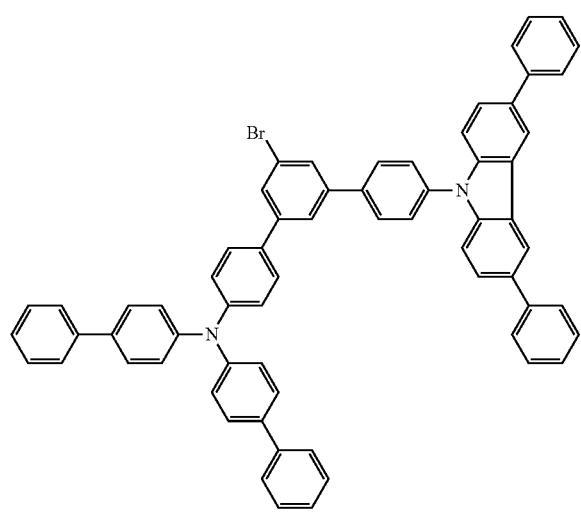
Sub 1-3(25)
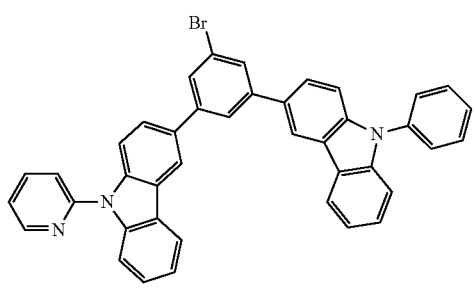

-continued
Sub 1-3(26)
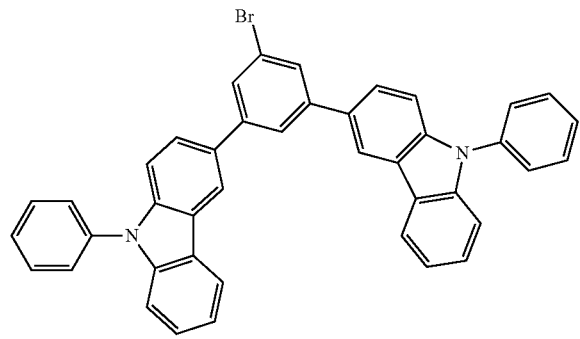
Sub 1-3(27)
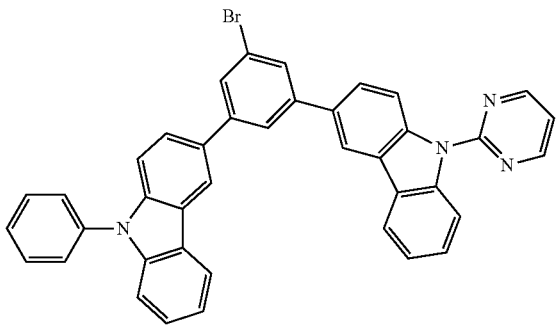
Sub 1-3(28)
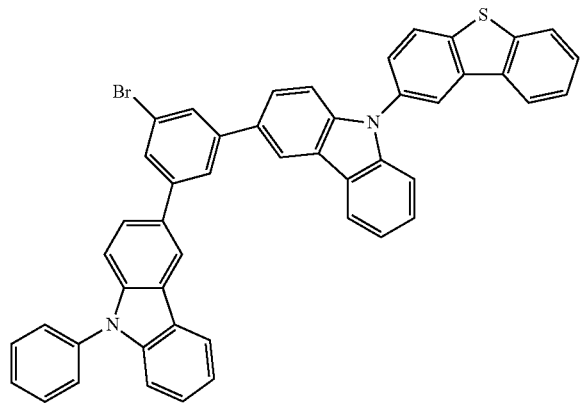
Sub 1-3(29)
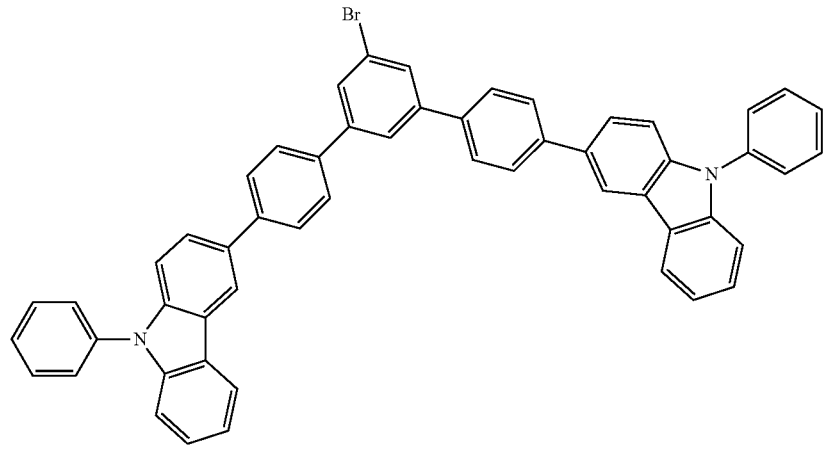
Sub 1-3(30)
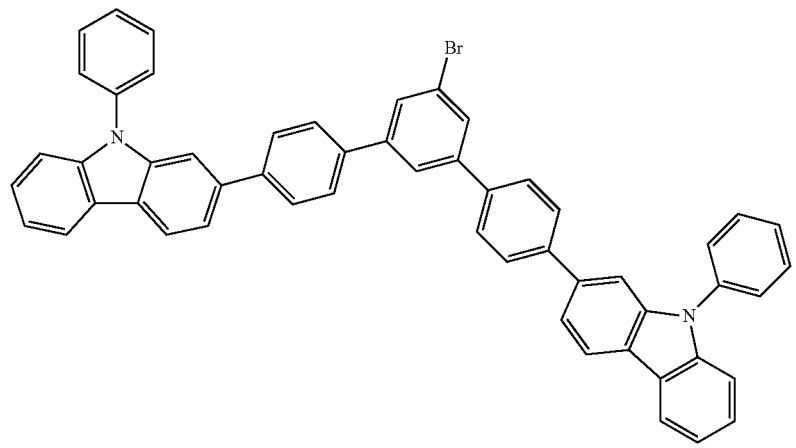

Sub 1-3(31)
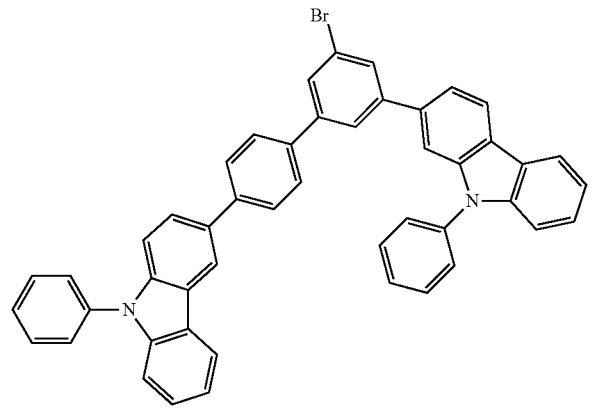
Sub 1-3(32)
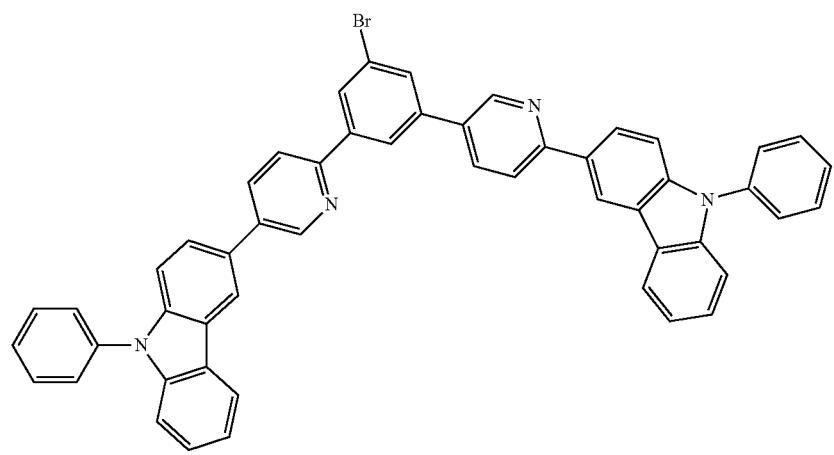
Sub 1-3(33)
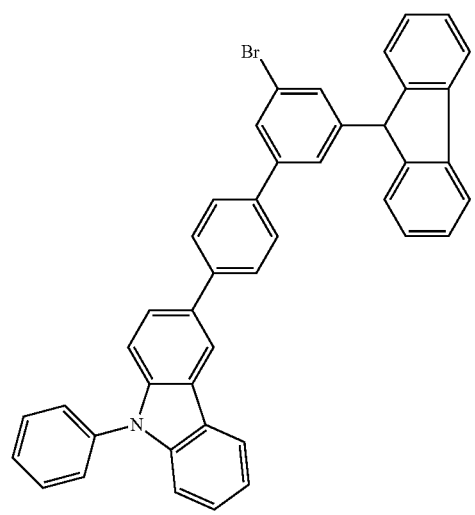

-continued
Sub 1-3(34)
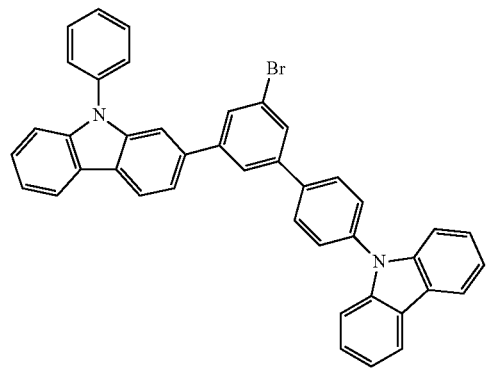
Sub 1-3(35)
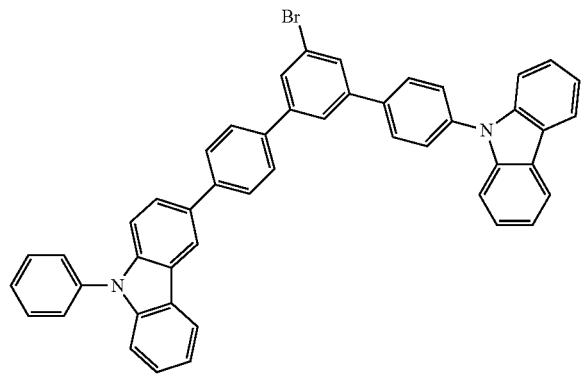
Sub 1-3(36)
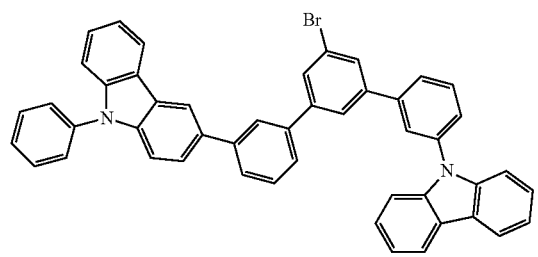
Sub 1-3(37)
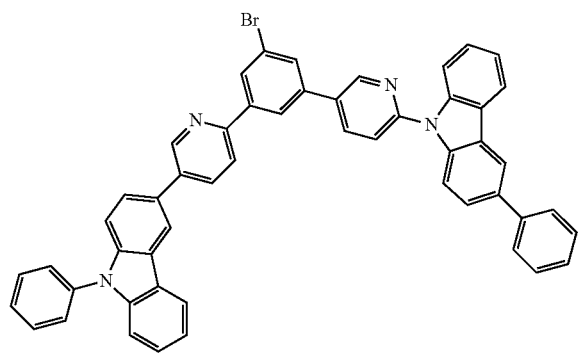
Sub 1-3(38)
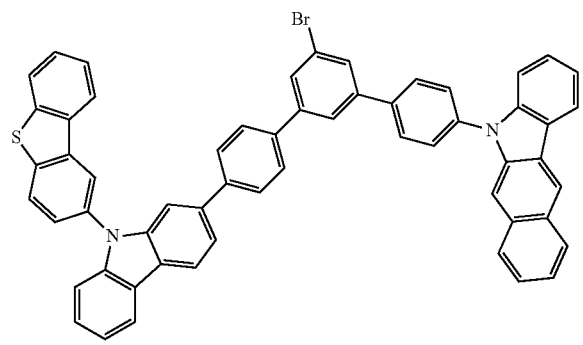
Sub 1-3(39)
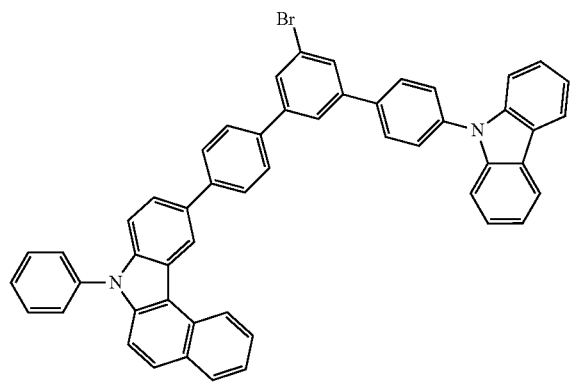
Sub 1-3(40)
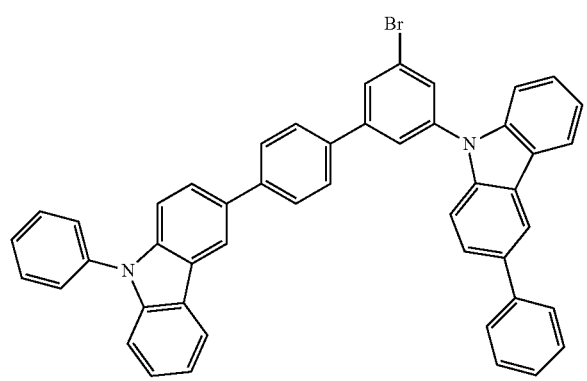

TABLE 1

| Compound | FD-MS | Compound | FD-MS |
|---|---|---|---|
| Sub 1-3(1) | m/z = 490.10($C_{30}H_{23}BrN_2$ = 491.42) | Sub 1-3(2) | m/z = 642.17($C_{42}H_{31}BrN_2$ = 643.61) |
| Sub 1-3(3) | m/z = 492.09($C_{28}H_{21}BrN_4$ = 493.40) | Sub 1-3(4) | m/z = 566.14($C_{36}H_{27}BrN_2$ = 567.52) |
| Sub 1-3(5) | m/z = 642.17($C_{42}H_{31}BrN_2$ = 643.61) | Sub 1-3(6) | m/z = 742.20($C_{50}H_{35}BrN_2$ = 743.73) |
| Sub 1-3(7) | m/z = 742.20($C_{50}H_{35}BrN_2$ = 743.73) | Sub 1-3(8) | m/z = 946.29($C_{66}H_{47}BrN_2$ = 948.00) |
| Sub 1-3(9) | m/z = 564.12($C_{36}H_{25}BrN_2$ = 565.50) | Sub 1-3(10) | m/z = 640.15($C_{42}H_{29}BrN_2$ = 641.60) |
| Sub 1-3(11) | m/z = 565.12($C_{35}H_{24}BrN_3$ = 566.49) | Sub 1-3(12) | m/z = 670.11($C_{42}H_{27}BrN_2S$ = 671.65) |
| Sub 1-3(13) | m/z = 640.15($C_{42}H_{29}BrN_2$ = 641.60) | Sub 1-3(14) | m/z = 740.18($C_{59}H_{33}BrN_2$ = 741.71) |
| Sub 1-3(15) | m/z = 740.18($C_{50}H_{33}BrN_2$ = 741.71) | Sub 1-3(16) | m/z = 944.28($C_{66}H_{45}BrN_2$ = 945.98) |
| Sub 1-3(17) | m/z = 538.10($C_{34}H_{23}BrN_2$ = 539.46) | Sub 1-3(18) | m/z = 640.15($C_{42}H_{29}BrN_2$ = 641.60) |
| Sub 1-3(19) | m/z = 489.08($C_{29}H_{20}BrN_3$ = 490.39) | Sub 1-3(20) | m/z = 564.12($C_{36}H_{25}BrN_2$ = 565.50) |
| Sub 1-3(21) | m/z = 640.15($C_{42}H_{29}BrN_2$ = 641.60) | Sub 1-3(22) | m/z = 690.17($C_{46}H_{31}BrN_2$ = 691.66) |
| Sub 1-3(23) | m/z = 740.18($C_{50}H_{33}BrN_2$ = 741.71) | Sub 1-3(24) | m/z = 944.28($C_{66}H_{45}BrN_2$ = 945.98) |
| Sub 1-3(25) | m/z = 639.13($C_{41}H_{26}BrN_3$ = 640.57) | Sub 1-3(26) | m/z = 638.14($C_{42}H_{27}BrN_2$ = 639.58) |
| Sub 1-3(27) | m/z = 640.13($C_{40}H_{25}BrN_4$ = 641.56) | Sub 1-3(28) | m/z = 744.12($C_{48}H_{29}BrN_2S$ = 745.73) |
| Sub 1-3(29) | m/z = 790.20($C_{54}H_{35}BrN_2$ = 791.77) | Sub 1-3(30) | m/z = 790.20($C_{54}H_{35}BrN_2$ = 791.77) |
| Sub 1-3(31) | m/z = 714.17($C_{48}H_{31}BrN_2$ = 715.68) | Sub 1-3(32) | m/z = 792.19($C_{52}H_{33}BrN_4$ = 793.75) |
| Sub 1-3(33) | m/z = 638.14($C_{42}H_{27}BrN_2$ = 639.58) | Sub 1-3(34) | m/z = 638.14($C_{42}H_{27}BrN_2$ = 639.58) |
| Sub 1-3(35) | m/z = 714.17($C_{48}H_{31}BrN_2$ = 715.68) | Sub 1-3(36) | m/z = 714.17($C_{48}H_{31}BrN_2$ = 715.68) |
| Sub 1-3(37) | m/z = 792.19($C_{52}H_{33}BrN_4$ = 793.75) | Sub 1-3(38) | m/z = 870.17($C_{58}H_{35}BrN_2S$ = 871.88) |
| Sub 1-3(39) | m/z = 764.18($C_{52}H_{33}BrN_2$ = 765.74) | Sub 1-3(40) | m/z = 714.17($C_{48}H_{31}BrN_2$ = 715.68) |

3. Synthesis Example of Sub 1-5

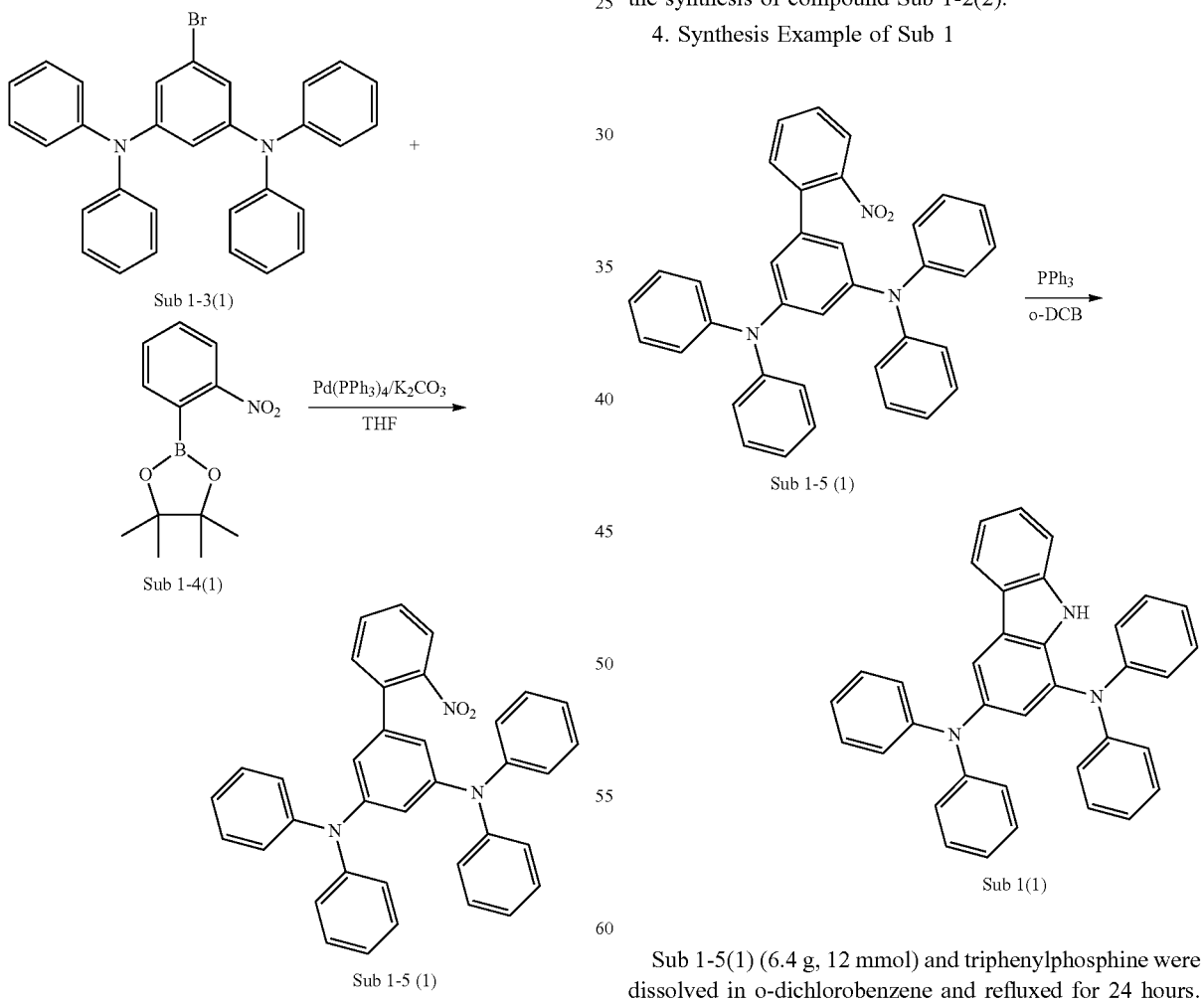

Sub 1-3(1) (7.9 g, 16 mmol), Sub 1-4(1) (5.5 g, 18 mmol), Pd(PPh$_3$)$_4$ (0.06 g, 0.05 mmol) and K$_2$CO$_3$ (6.6 g, 48 mmol) were dissolved in anhydrous THF and a small amount water, and 3.9 g (yield: 76%) of the product Sub 1-5(1) was obtained by using the same manner as described above for the synthesis of compound Sub 1-2(2).

4. Synthesis Example of Sub 1

Sub 1-5(1) (6.4 g, 12 mmol) and triphenylphosphine were dissolved in o-dichlorobenzene and refluxed for 24 hours. When the reaction was completed, the solvent was removed by distillation under reduced pressure, and the concentrated product was separated by column chromatography to obtain 4.7 g (yield: 78%) of the product Sub 1 (1).

Meanwhile, examples of Sub 1 are as followings, but are not limited to, and Table 2 below shows the FD-MS values thereof.
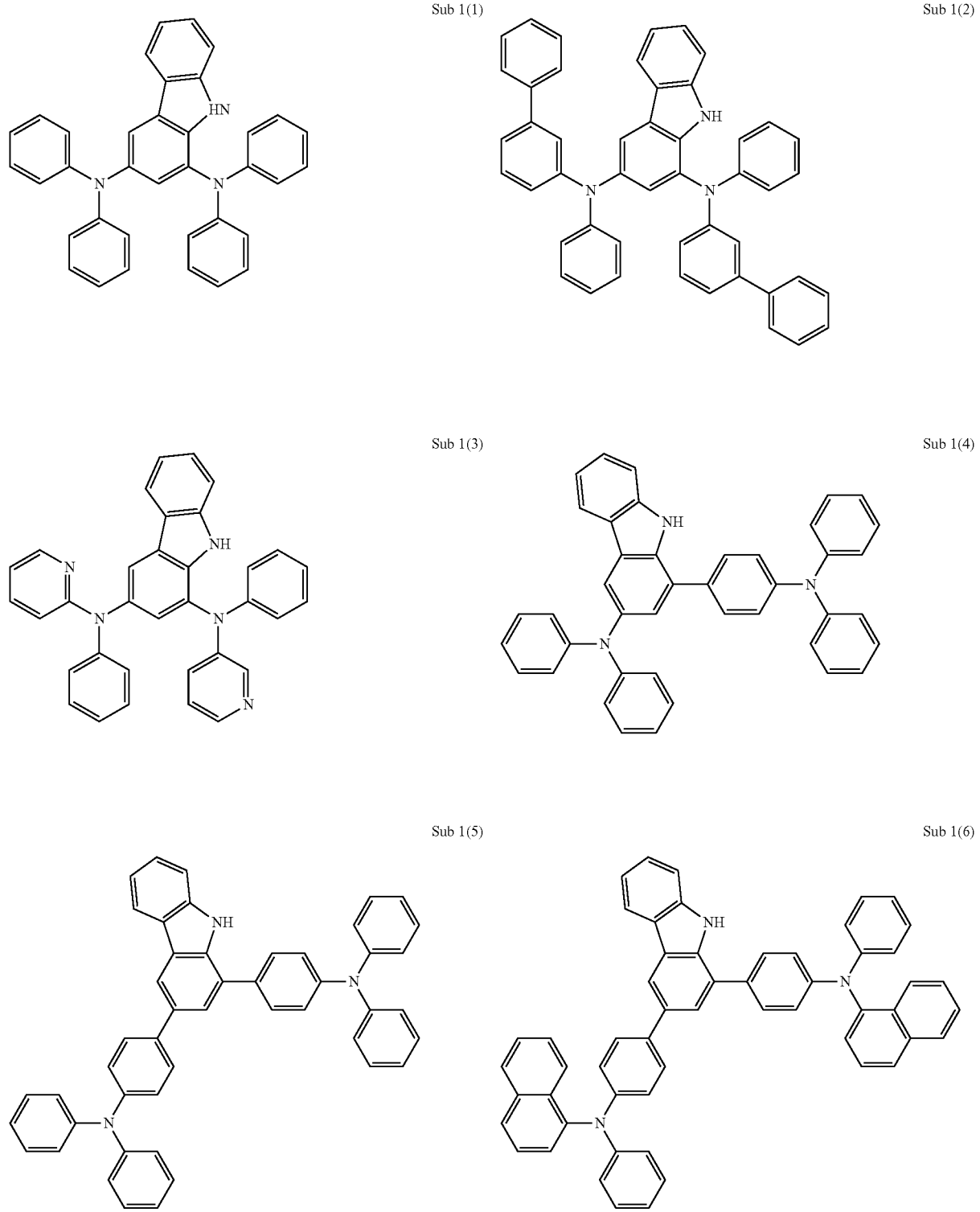

Sub 1(7)
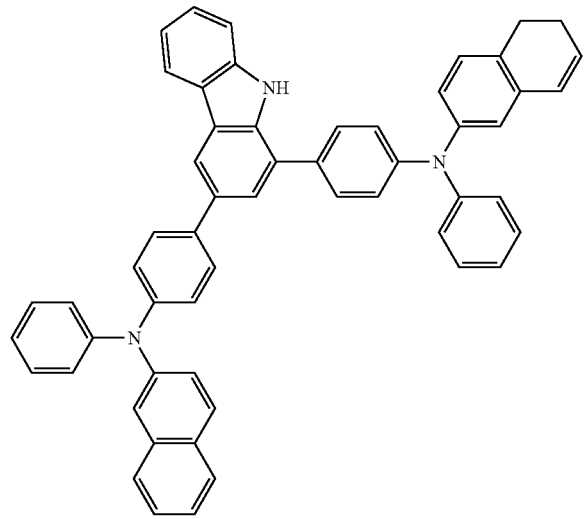
Sub 1(8)
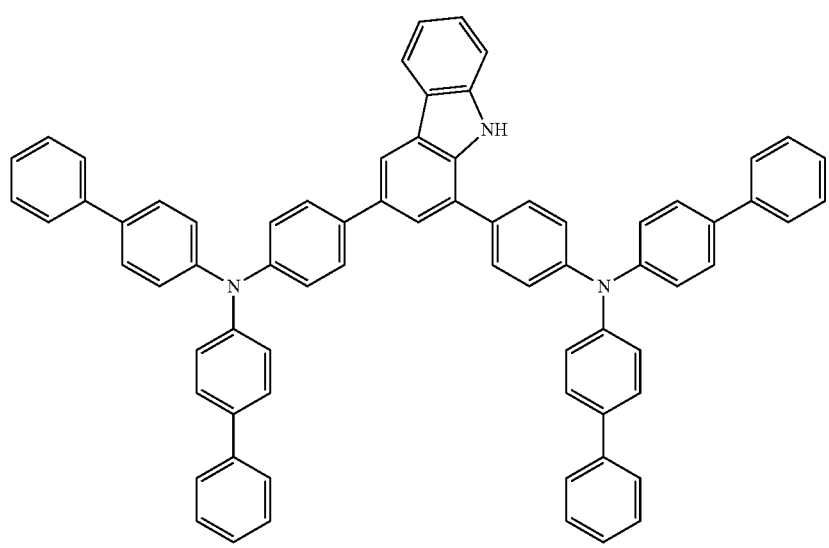
Sub 1(9)
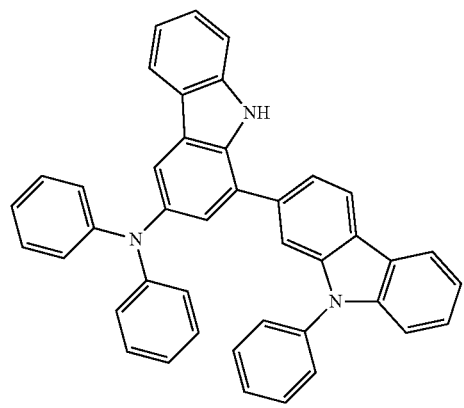
Sub 1(10)
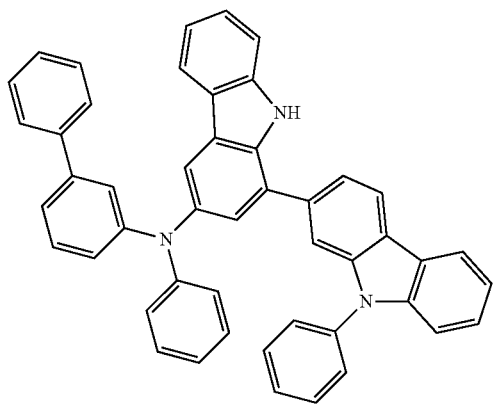

-continued
Sub 1(11)
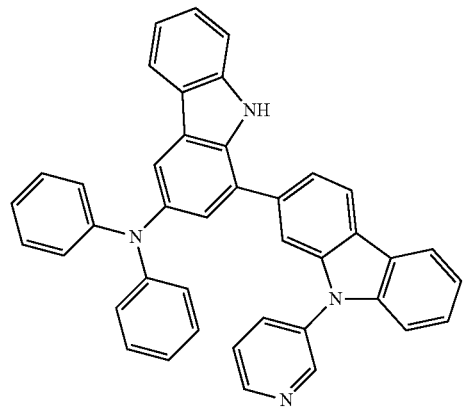
Sub 1(12)
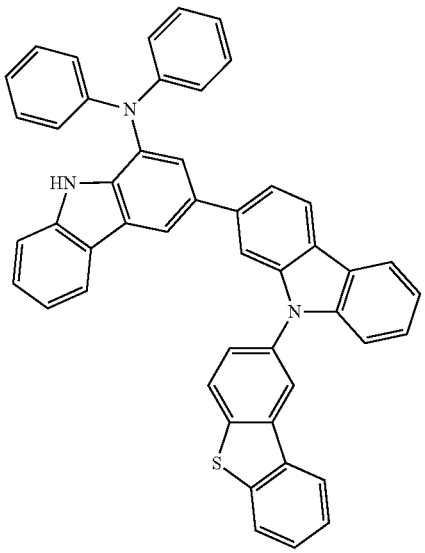
Sub 1(13)
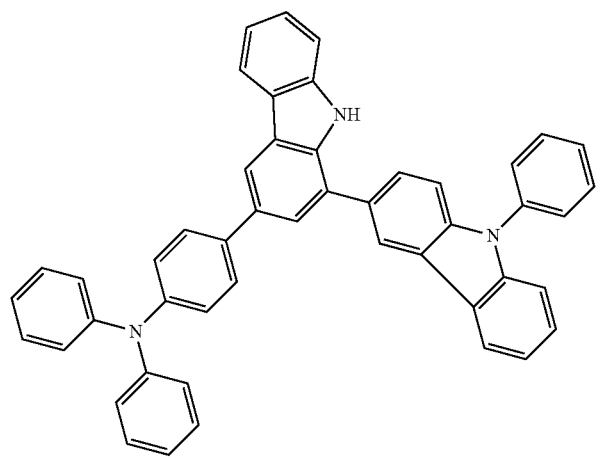
Sub 1(14)
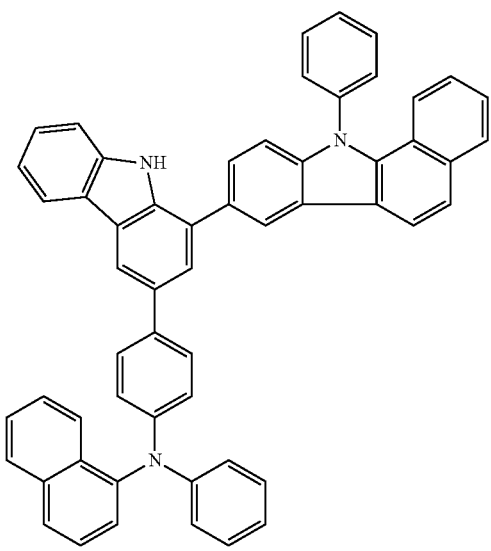
Sub 1(15)
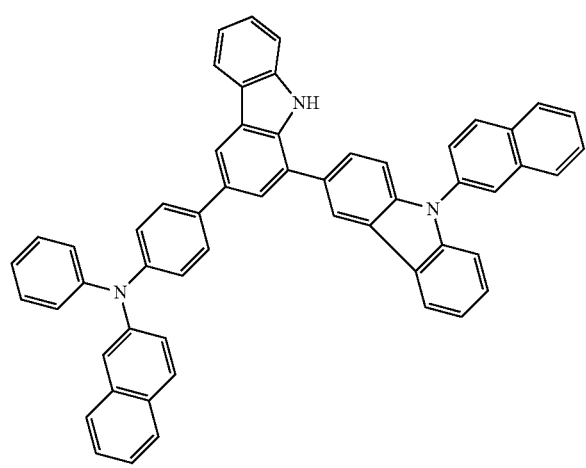

Sub 1(16)
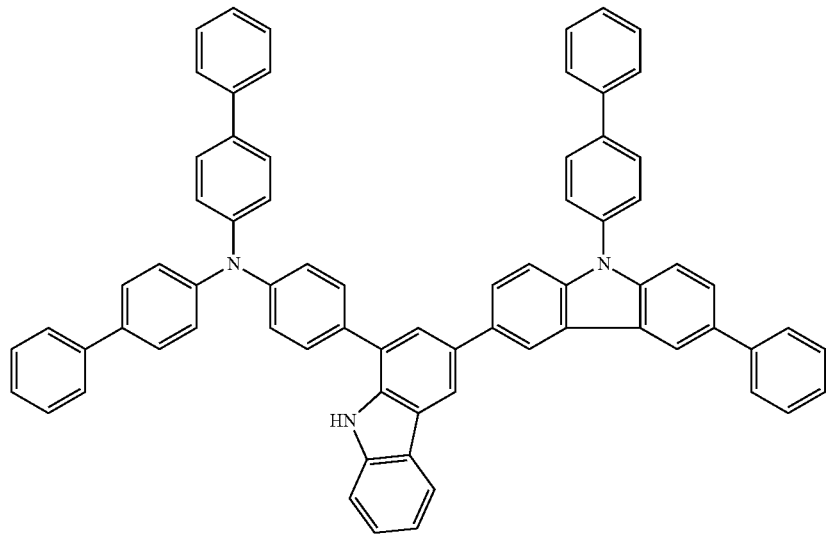
Sub 1(17)
Sub 1(18)
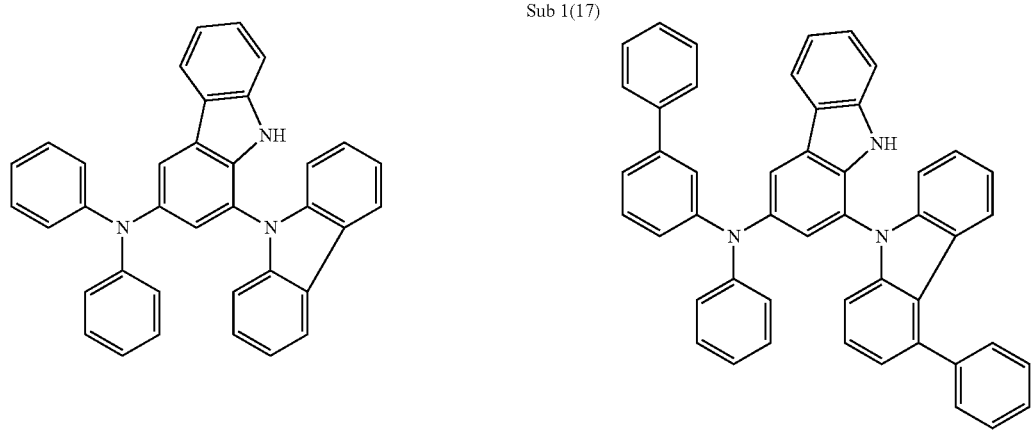
Sub 1(19)
Sub 1(20)
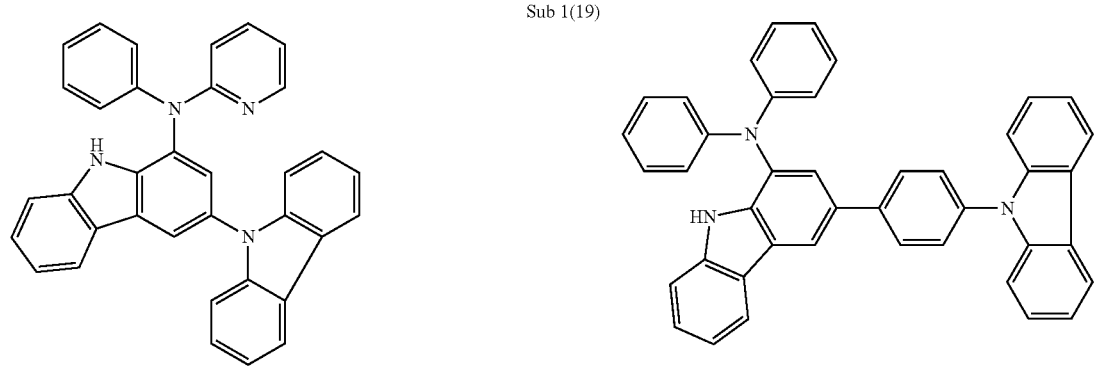

Sub 1(21)
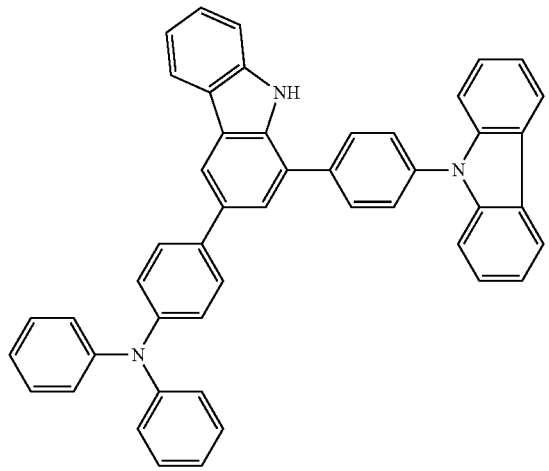
Sub 1(22)
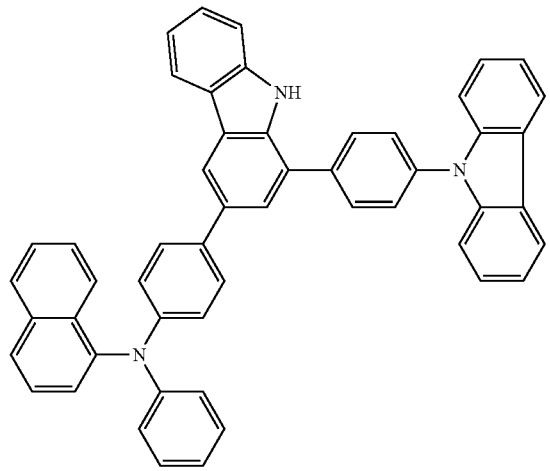
Sub 1(23)
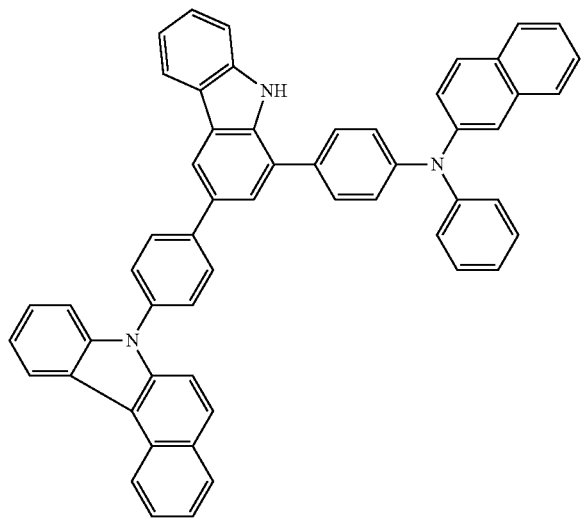
Sub 1(24)
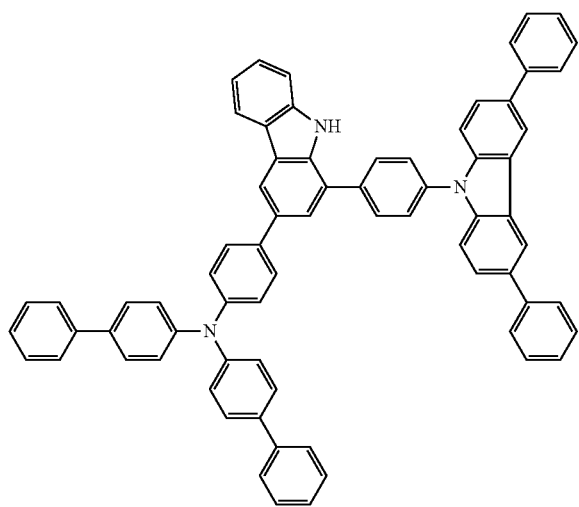
Sub 1(25)
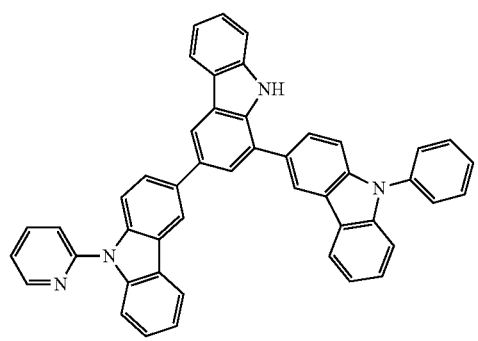

-continued
Sub 1(26)
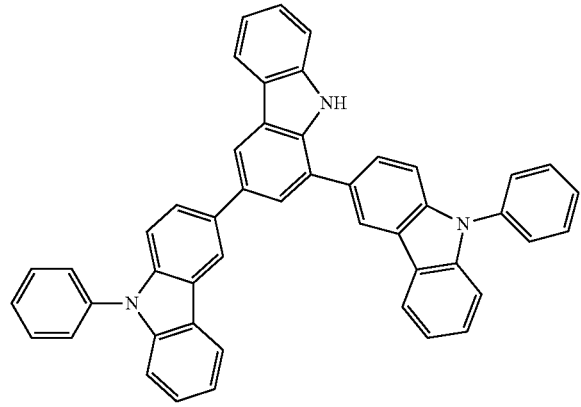
Sub 1(27)
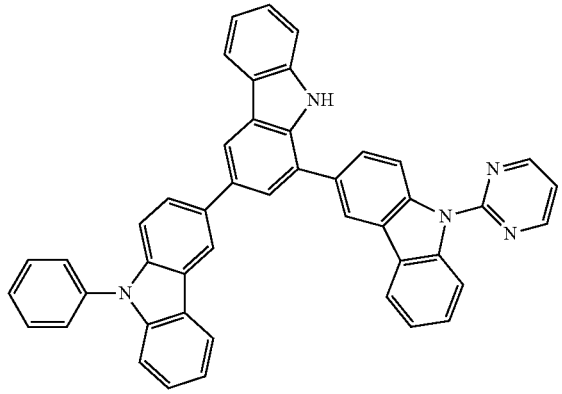
Sub 1(28)
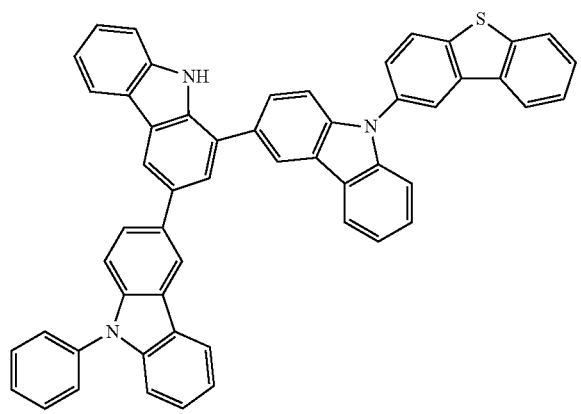
Sub 1(29)
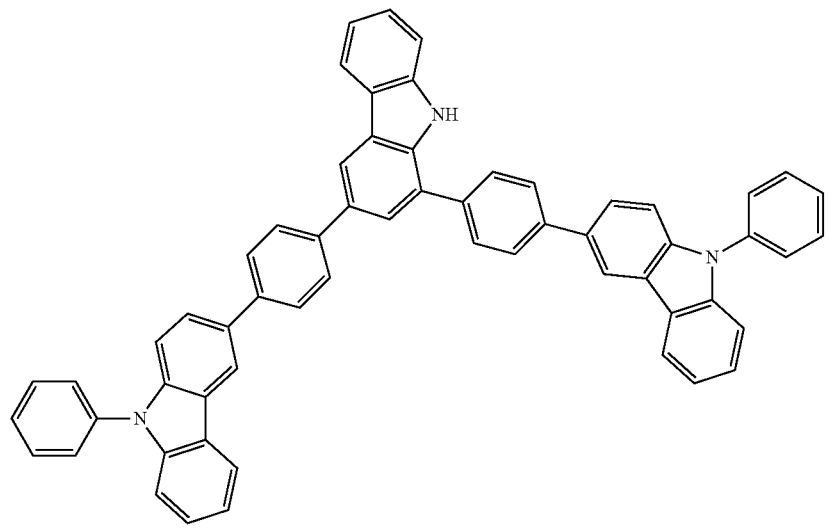

-continued
Sub 1(30)
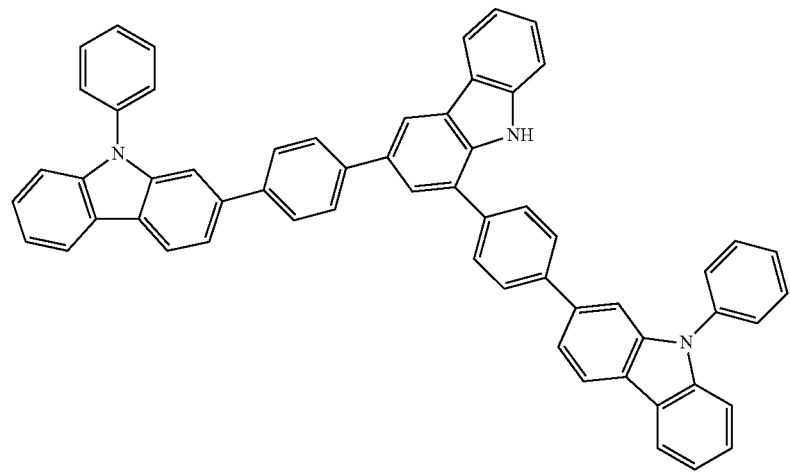
Sub 1(31)
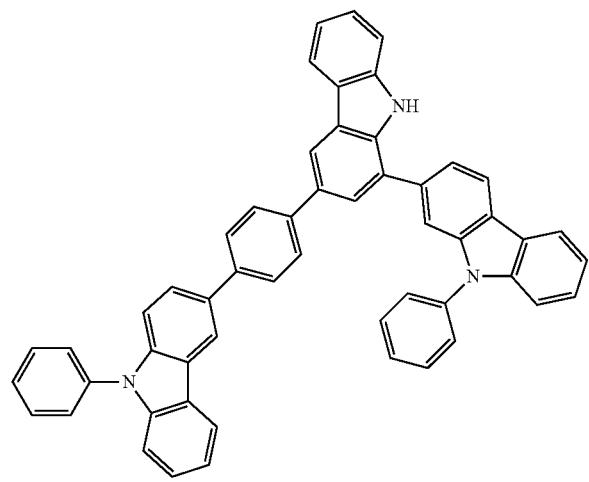
Sub 1(32)
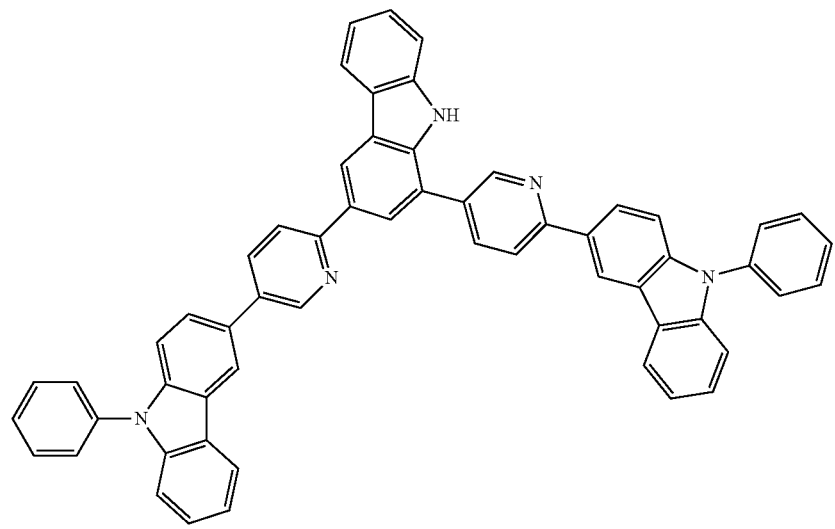

Sub 1(33)
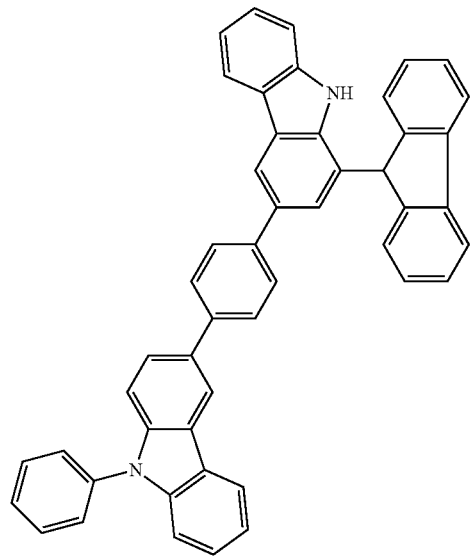
Sub 1(34)
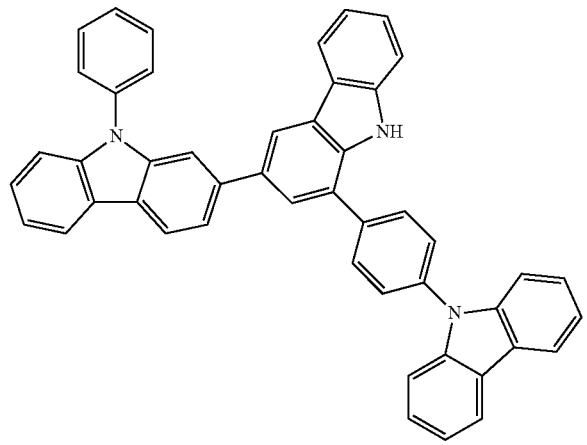
Sub 1(35)
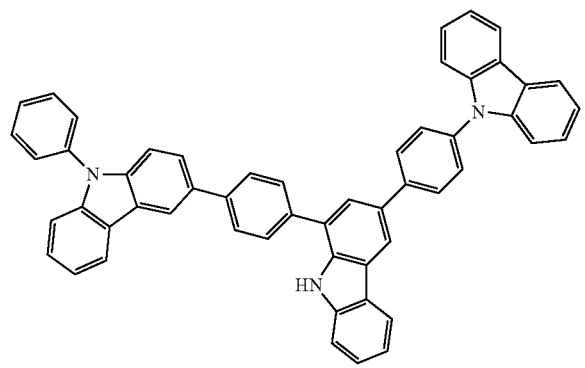
Sub 1(36)
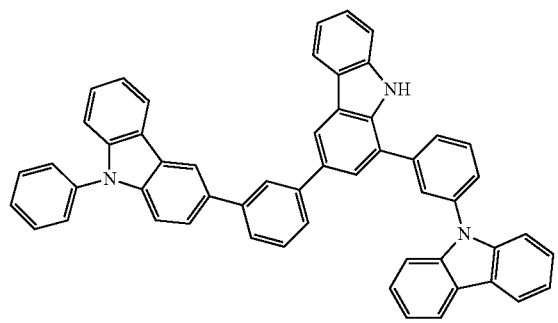
Sub 1(37)
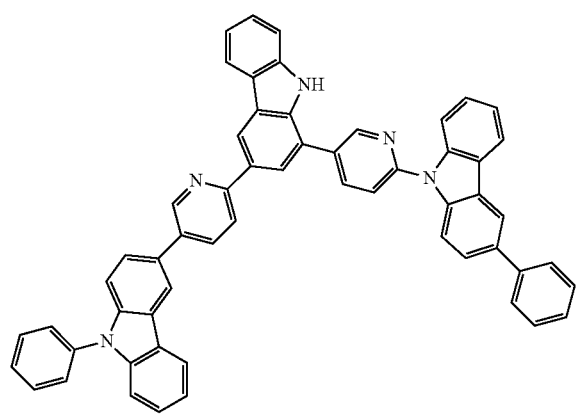
Sub 1(38)
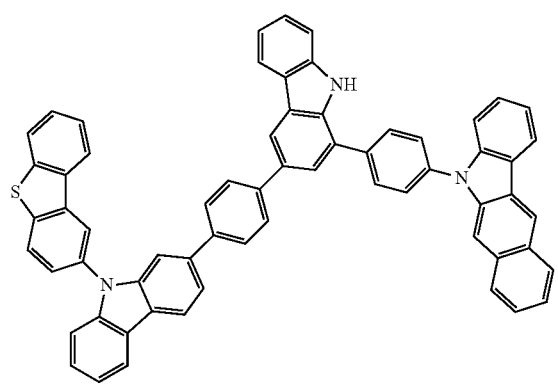

Sub 1(39)
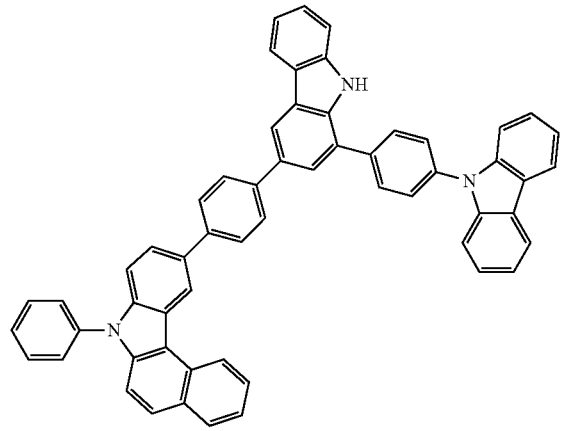
Sub 1(40)
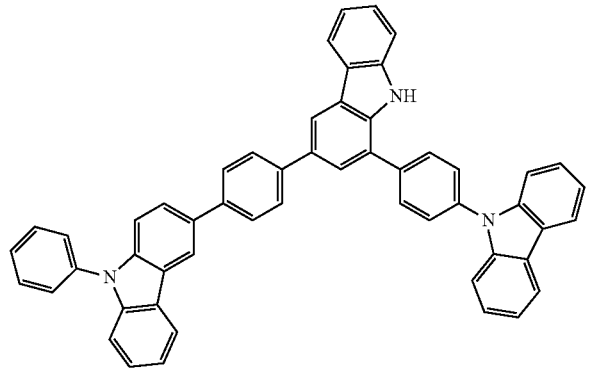
Sub 1(41)
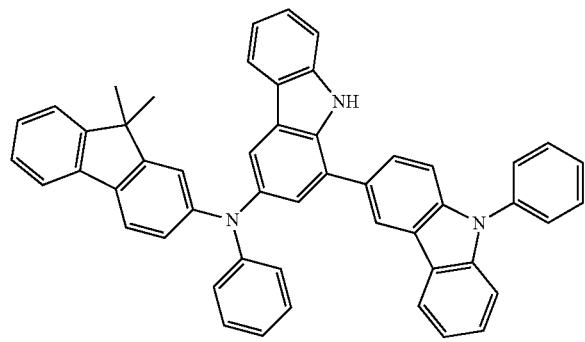
Sub 1(42)
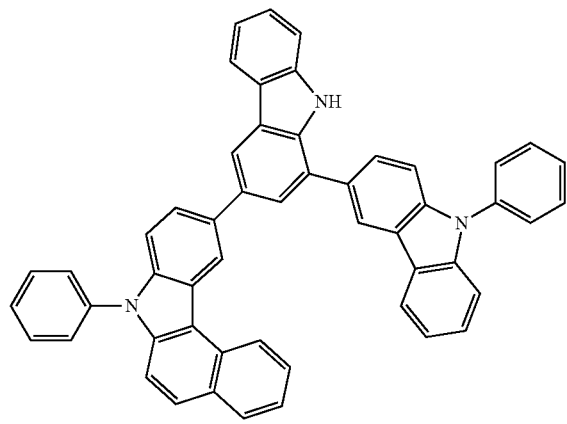
Sub 1(43)
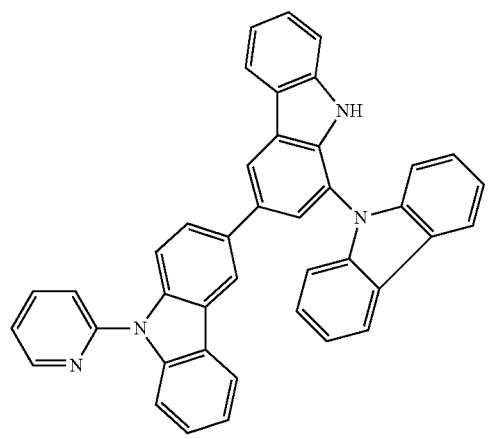
Sub 1(44)
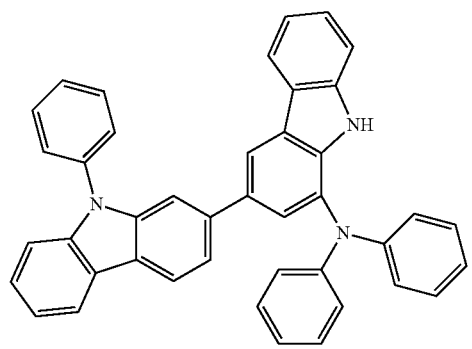

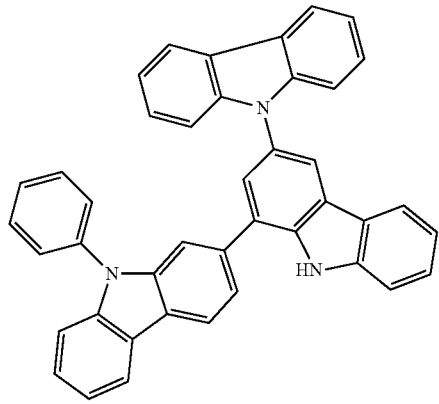

Sub 1(45)

TABLE 2

| compound | FD-MS | compound | FD-MS |
|---|---|---|---|
| Sub 1(1) | m/z = 501.22($C_{36}H_{27}N_3$ = 501.62) | Sub 1(2) | m/z = 653.28($C_{48}H_{35}N_3$ = 653.81) |
| Sub 1(3) | m/z = 503.21 ($C_{34}H_{25}N_5$ = 503.60) | Sub 1(4) | m/z = 577.25($C_{42}H_{31}N_3$ = 577.72) |
| Sub 1(5) | m/z = 653.28($C_{48}H_{35}N_3$ = 653.81) | Sub 1(6) | m/z = 753.31($C_{56}H_{39}N_3$ = 753.93) |
| Sub 1(7) | m/z = 753.31($C_{56}H_{39}N_3$ = 753.93) | Sub 1(8) | m/z = 957.41($C_{72}H_{51}N_3$ = 958.20) |
| Sub 1(9) | m/z = 575.24($C_{42}H_{29}N_3$ = 575.70) | Sub 1(10) | m/z = 651.27($C_{48}H_{33}N_3$ = 651.80) |
| Sub 1(11) | m/z = 576.23($C_{41}H_{25}N_4$ = 576.69) | Sub 1(12) | m/z = 681.22($C_{48}H_{31}N_3S$ = 681.84) |
| Sub 1(13) | m/z = 651.27($C_{48}H_{33}N_3$ = 651.80) | Sub 1(14) | m/z = 751.30($C_{56}H_{37}N_3$ = 751.91) |
| Sub 1(15) | m/z = 751.30($C_{56}H_{37}N_3$ = 751.91) | Sub 1(16) | m/z = 955.39($C_{72}H_{49}N_3$ = 956.18) |
| Sub 1(17) | m/z = 549.22($C_{40}H_{27}N_3$ = 549.66) | Sub 1(18) | m/z = 651.27($C_{45}H_{33}N_3$ = 651.80) |
| Sub 1(19) | m/z = 500.20($C_{35}H_{24}N_4$ = 500.59) | Sub 1(20) | m/z = 575.24($C_{42}H_{29}N_3$ = 575.70) |
| Sub 1(21) | m/z = 651.27($C_{46}H_{33}N_3$ = 651.80) | Sub 1(22) | m/z = 701.28($C_{52}H_{35}N_3$ = 701.85) |
| Sub 1(23) | m/z = 751.30($C_{56}H_{37}N_3$ = 751.91) | Sub 1(24) | m/z = 955.39($C_{72}H_{49}N_3$ = 956.18) |
| Sub 1(25) | m/z = 650.25($C_{47}H_{30}N_4$ = 650.77) | Sub 1(26) | m/z = 649.25($C_{48}H_{31}N_3$ = 649.78) |
| Sub 1(27) | m/z = 651.24($C_{46}H_{29}N_5$ = 651.76) | Sub 1(28) | m/z = 755.24($C_{54}H_{35}NS$ = 755.92) |
| Sub 1(29) | m/z = 801.31($C_{60}H_{30}N_3$ = 801.967) | Sub 1(30) | m/z = 801.31($C_{60}H_{39}N_3$ = 801.97) |
| Sub 1(31) | m/z = 825.28($C_{54}H_{35}N_3$ = 725.88) | Sub 1(32) | m/z = 803.30($C_{58}H_{37}N_5$ = 803.95) |
| Sub 1(33) | m/z = 649.25($C_{40}H_{31}N_3$ = 649.78) | Sub 1(34) | m/z = 649.25($C_{48}H_{31}N_3$ = 649.78) |
| Sub 1(35) | m/z = 725.28($C_{54}H_{35}N_3$ = 725.88) | Sub 1(36) | m/z = 725.28($C_{54}H_{35}N_3$ = 725.88) |
| Sub 1(37) | m/z = 803.30($C_{58}H_{37}N_9$ = 803.95) | Sub 1(38) | m/z = 881.29($C_{64}H_{39}N_3S$ = 882.08) |
| Sub 1(39) | m/z = 775.30($C_{58}H_{37}N_3$ = 775.93) | Sub 1(40) | m/z = 725.28($C_{54}H_{35}N_3$ = 725.88) |
| Sub 1(41) | m/z = 691.30($C_{51}H_{37}N_3$ = 691.86) | Sub 1(42) | m/z = 699.27($C_{52}H_{33}N_3$ = 699.84) |
| Sub 1(43) | m/z = 574.22($C_{41}H_{26}N_4$ = 574.67) | Sub 1(44) | m/z = 575.24($C_{42}H_{29}N_5$ = 575.70) |
| Sub 1(45) | m/z = 573.22($C_{42}H_{27}N_3$ = 573.68) | | |

I. Example of Sub 2

Examples of Sub 2 of the reaction scheme 1 are as followings, but are not limited to.

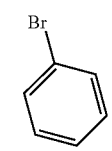

Sub 2-1

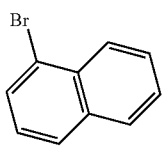

Sub 2-2

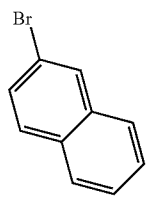

Sub 2-3

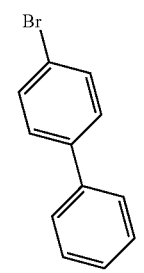

Sub 2-4

Sub 2-5
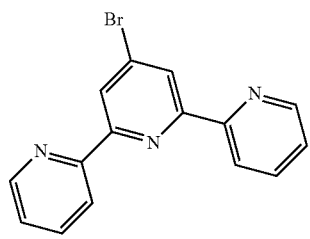
Sub 2-6
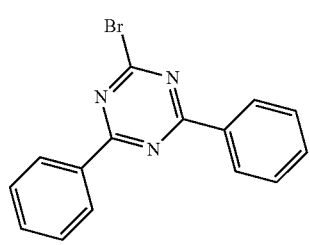
Sub 2-7
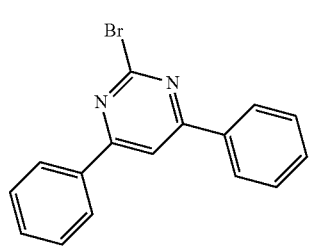
Sub 2-8
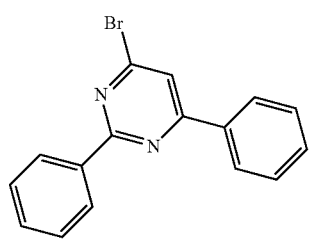
Sub 2-9
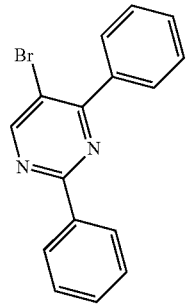
Sub 2-10
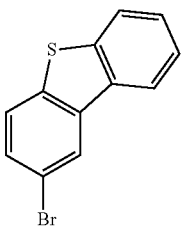
Sub 2-11
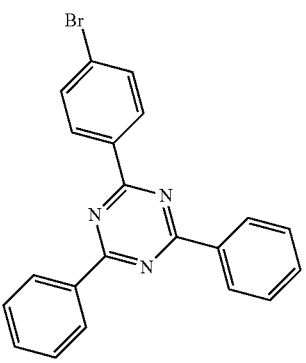
Sub 2-12
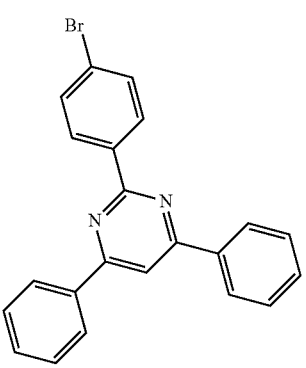
Sub 2-13
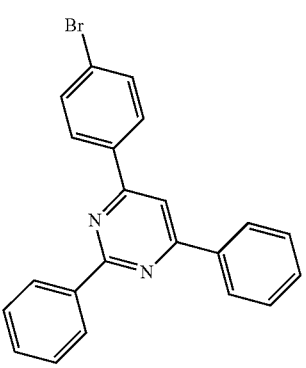
Sub 2-14
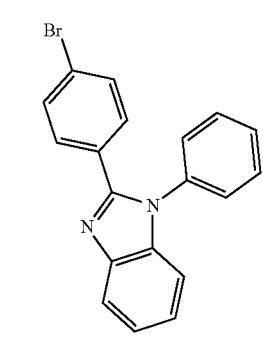

-continued

Sub 2-15

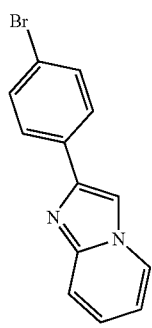

Sub 2-16

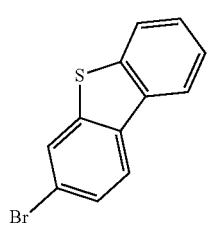

Sub 2-17

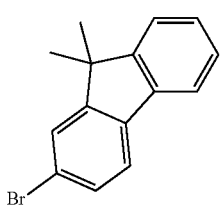

III. Synthesis Example of Final Products
1. Synthesis Example of Compound 1-1

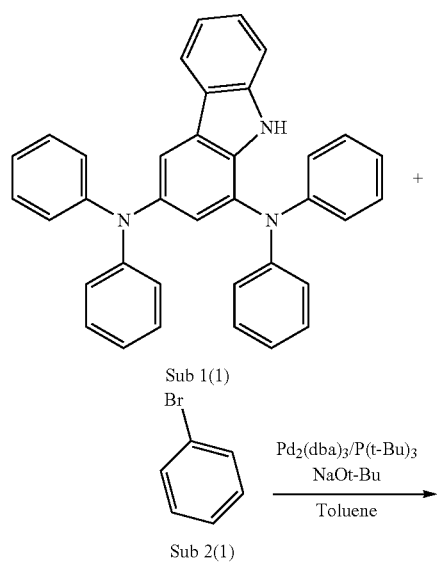

-continued

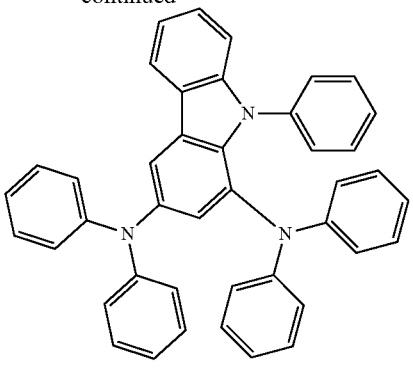

1-1

Sub 1(1) (10.0 g, 20 mmol), Sub 2-1 (3.5 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, followed by reaction at 100° C. After completion of the reaction, the reaction product was extracted with CH$_2$Cl$_2$ and water. The organic layer was dried over MgSO$_4$ and concentrated. The resulting compound was purified by silicagel column and recrystallized to obtain 6.5 g (yield: 65%) of the product 1-1.

2. Synthesis Example of Compound 2-5

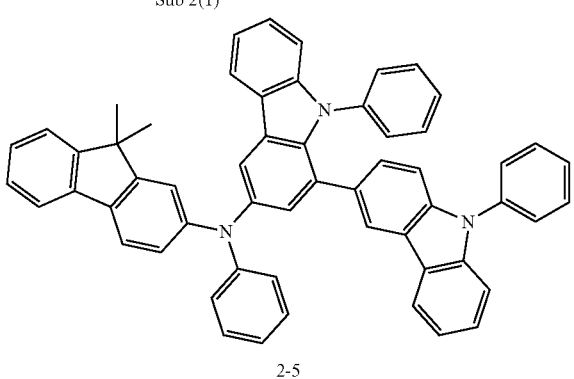

Sub 1(41) (13.8 g, 20 mmol), Sub 2-1 (3.5 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 9.5 g (yield: 62%) of the product 2-5 was obtained by using the same manner as described above for the synthesis of the product 1-1.

3. Synthesis Example of Compound 3-9

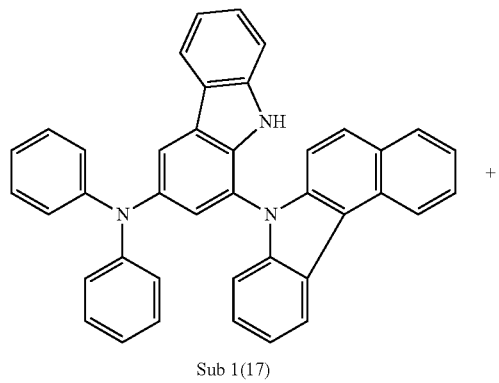
Sub 1(17)

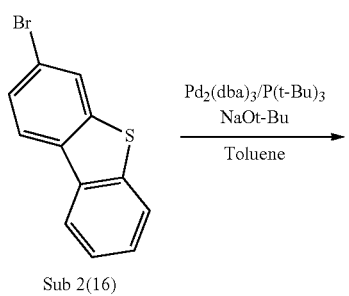
Sub 2(16)

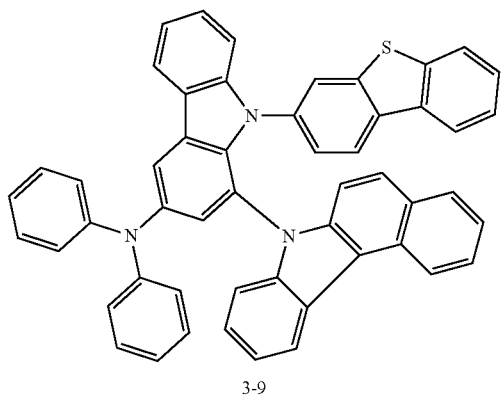
3-9

Sub 1(17) (11.0 g, 20 mmol), Sub 2-16 (5.8 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 8.8 g (yield: 60%) of the product 3-9 was obtained by using the same manner as described above for the synthesis of the product 1-1.

4. Synthesis Example of Compound 4-13

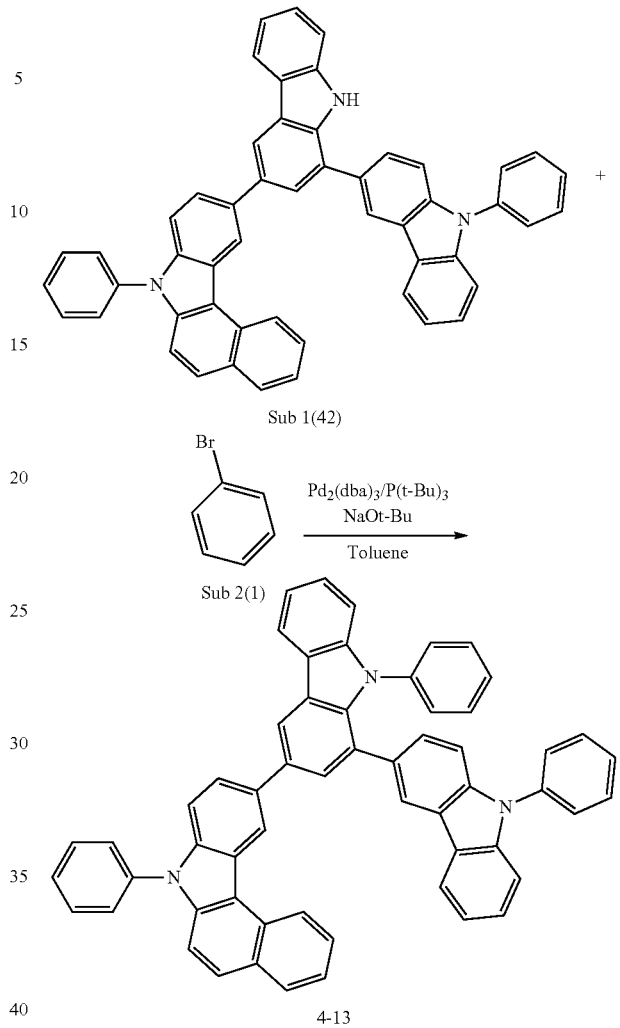

Sub 1(42) (14.0 g, 20 mmol), Sub 2-1 (3.5 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 9.8 g (yield: 63%) of the product 4-13 was obtained by using the same manner as described above for the synthesis of the product 1-1.

5. Synthesis Example of Compound 5-5

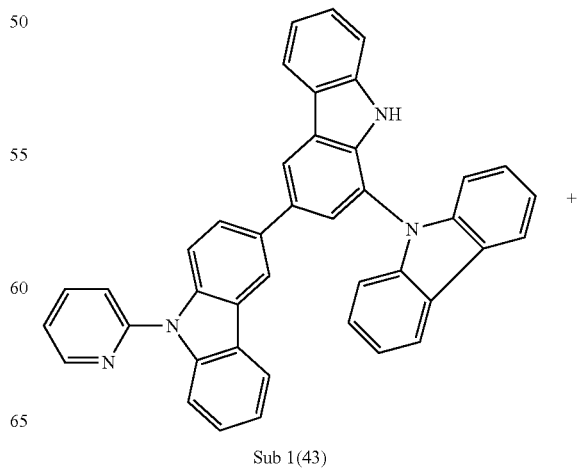
Sub 1(43)

-continued

Sub 1(43) (14.0 g, 20 mmol), Sub 2(1) (3.5 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 8.5 g (yield: 65%) of the product 5-5 was obtained by using the same manner as described above for the synthesis of the product 1-1.

6. Synthesis Example of Compound 6-9

-continued

Sub 1(44) (11.5 g, 20 mmol), Sub 2-10-(5.8 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 8.9 g (yield: 59%) of the product 6-9 was obtained by using the same manner as described above for the synthesis of the product 1-1.

7. Synthesis Example of Compound 7-7

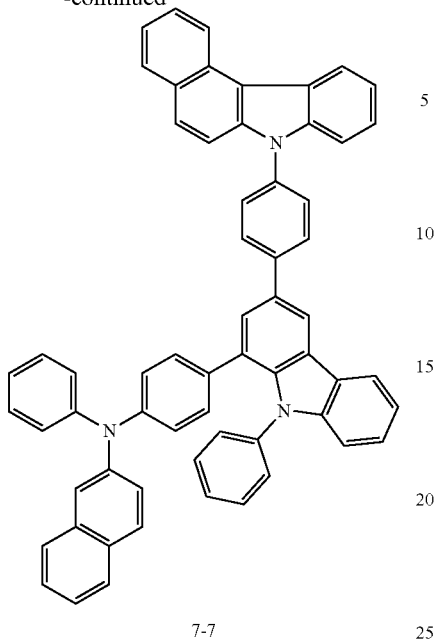

7-7

Sub 1(23) (15.0 g, 20 mmol), Sub 2-1 (3.5 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 10.8 g (yield: 65%) of the product 7-7 was obtained by using the same manner as described above for the synthesis of the product 1-1.

8. Synthesis Example of Compound 8-4

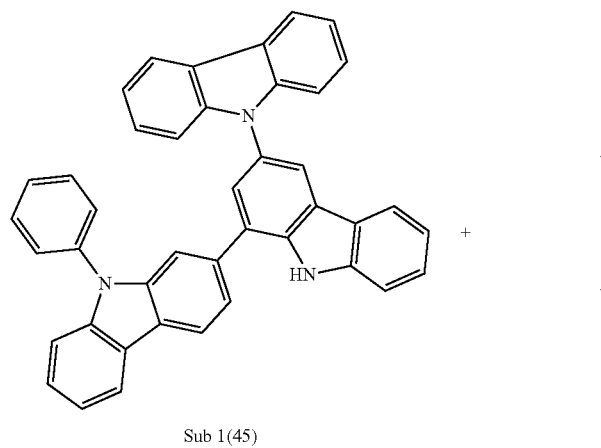

Sub 1(45)

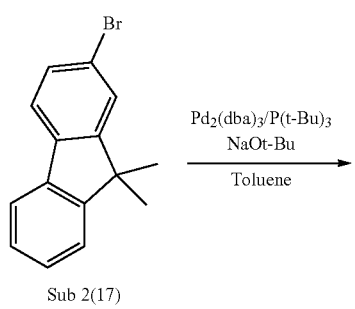

Sub 2(17)

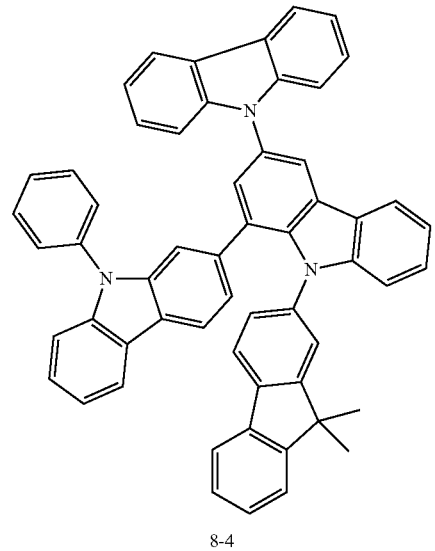

8-4

Sub 1(45) (11.5 g, 20 mmol), Sub 2-17 (6.0 g, 22 mmol), Pd$_2$(dba)$_3$ (0.5 g, 0.6 mmol), P(t-Bu)$_3$ (0.2 g, 2 mmol), t-BuONa (5.8 g, 60 mmol) and toluene (300 mL) were added, and 9.2 g (yield: 60%) of the product 8-4 was obtained by using the same manner as described above for the synthesis of the product 1-1.

Meanwhile, Table 3 shows FD-MS values of the compounds of the present invention prepared according to the above synthesis example.

TABLE 3

| Compound | FD-MS | Compound | FD-MS |
| --- | --- | --- | --- |
| 1-1 | m/z = 577.25(C$_{42}$H$_{31}$N$_3$ = 577.72) | 1-2 | m/z = 677.28(C$_{50}$H$_{35}$N$_3$ = 677.83) |
| 1-3 | m/z = 677.28(C$_{50}$H$_{35}$N$_3$ = 677.83) | 1-4 | m/z = 881.38(C$_{66}$H$_{47}$N$_3$ = 882.10) |
| 1-5 | m/z = 809.38(C$_{60}$H$_{47}$N$_3$ = 810.04) | 1-6 | m/z = 1057.44(C$_{80}$H$_{55}$N$_3$ = 1058.31) |
| 1-7 | m/z = 1053.41(C$_{80}$H$_{51}$N$_3$ = 1054.28) | 1-8 | m/z = 789.23(C$_{54}$H$_{35}$N$_3$S$_2$ = 790.01) |
| 1-9 | m/z = 683.24(C$_{48}$H$_{33}$N$_3$S = 683.86) | 1-10 | m/z = 730.31(C$_{53}$H$_{38}$N$_4$ = 730.90) |
| 1-11 | m/z = 579.24(C$_{40}$H$_{29}$N$_5$ = 579.69) | 1-12 | m/z = 653.28(C$_{48}$H$_{35}$N$_3$ = 653.81) |
| 1-13 | m/z = 729.31(C$_{54}$H$_{39}$N$_3$ = 729.91) | 1-14 | m/z = 829.35(C$_{62}$H$_{43}$N$_3$ = 830.02) |
| 1-15 | m/z = 829.35(C$_{62}$H$_{43}$N$_3$ = 830.02) | 1-16 | m/z = 1033.44(C$_{78}$H$_{55}$N$_3$ = 1034.29) |
| 1-17 | m/z = 961.44(C$_{72}$H$_{55}$N$_3$ = 962.23) | 1-18 | m/z = 1209.50(C$_{92}$H$_{63}$N$_3$ = 1210.50) |
| 1-19 | m/z = 1205.47(C$_{92}$H$_{59}$N$_3$ = 1206.47) | 1-20 | m/z = 941.29(C$_{66}$H$_{43}$N$_3$S$_2$ = 942.20) |
| 1-21 | m/z = 835.30(C$_{60}$H$_{41}$N$_3$S = 836.05) | 1-22 | m/z = 882.37(C$_{65}$H$_{46}$N$_4$ = 883.09) |
| 1-23 | m/z = 731.30(C$_{52}$H$_{37}$N$_5$ = 731.88) | 1-24 | m/z = 807.34(C$_{58}$H$_{41}$N$_5$ = 807.98) |

TABLE 3-continued

| Compound | FD-MS | Compound | FD-MS |
|---|---|---|---|
| 1-25 | m/z = 941.29($C_{66}H_{43}N_3S_2$ = 942.20) | 1-26 | m/z = 961.44($C_{72}H_{55}N_3$ = 962.23) |
| 1-27 | m/z = 1209.50($C_{92}H_{63}N_3$ = 1210.50) | 1-28 | m/z = 1209.50($C_{92}H_{63}N_3$ = 1210.50) |
| 2-1 | m/z = 651.27($C_{48}H_{33}N_3$ = 651.80) | 2-2 | m/z = 701.28($C_{52}H_{35}N_3$ = 701.85) |
| 2-3 | m/z = 701.28($C_{52}H_{35}N_3$ = 701.85) | 2-4 | m/z = 803.33($C_{60}H_{41}N_3$ = 803.99) |
| 2-5 | m/z = 767.33($C_{57}H_{41}N_3$ = 767.96) | 2-6 | m/z = 891.36($C_{67}H_{45}N_3$ = 892.09) |
| 2-7 | m/z = 889.35($C_{67}H_{43}N_3$ = 890.08) | 2-8 | m/z = 857.29($C_{62}H_{39}N_3S$ = 858.06) |
| 2-9 | m/z = 757.26($C_{54}H_{35}N_3S$ = 757.94) | 2-10 | m/z = 728.29($C_{53}H_{36}N_4$ = 728.88) |
| 2-11 | m/z = 652.26($C_{47}H_{32}N_4$ = 652.78) | 2-12 | m/z = 757.26(C54H35N3S = 757.94) |
| 2-13 | m/z = 727.30($C_{54}H_{37}N_3$ = 727.89) | 2-14 | m/z = 827.33($C_{62}H_{41}N_3$ = 828.01) |
| 2-15 | m/z = 827.33($C_{62}H_{41}N_3$ = 828.01) | 2-16 | m/z = 1031.42($C_{78}H_{53}N_3$ = 1032.28) |
| 2-17 | m/z = 843.36($C_{63}H_{45}N_3$ = 844.05) | 2-18 | m/z = 967.39($C_{73}H_{49}N_3$ = 968.19) |
| 2-19 | m/z = 965.38($C_{73}H_{47}N_3$ = 966.17) | 2-20 | m/z = 833.29($C_{60}H_{39}N_3S$ = 834.04) |
| 2-21 | m/z = 833.29($C_{60}H_{39}N_3S$ = 834.04) | 2-22 | m/z = 880.36($C_{65}H_{44}N_4$ = 881.07) |
| 2-23 | m/z = 728.29($C_{53}H_{36}N_4$ = 728.88) | 2-24 | m/z = 803.33($C_{60}H_{41}N_3$ = 803.99) |
| 2-25 | m/z = 1015.31($C_{72}H_{45}N_3S_2$ = 1016.28) | 2-26 | m/z = 803.33($C_{60}H_{41}N_3$ = 803.99) |
| 2-27 | m/z = 1283.52($C_{98}H_{65}N_3$ = 1284.58) | 2-28 | m/z = 1279.49($C_{98}H_{61}N_3$ = 1280.55) |
| 3-1 | m/z = 575.24($C_{42}H_{29}N_3$ = 575.70) | 3-2 | m/z = 625.25($C_{46}H_{31}N_3$ = 625.76) |
| 3-3 | m/z = 625.25($C_{46}H_{31}N_3$ = 625.76) | 3-4 | m/z = 727.30($C_{54}H_{37}N_3$ = 727.89) |
| 3-5 | m/z = 691.30($C_{51}H_{37}N_3$ = 691.86) | 3-6 | m/z = 815.33($C_{61}H_{41}N_3$ = 816.00) |
| 3-7 | m/z = 813.31($C_{61}H_{39}N_3$ = 813.98) | 3-8 | m/z = 681.22($C_{48}H_{31}N_3S$ = 681.84) |
| 3-9 | m/z = 731.24($C_{52}H_{33}N_3S$ = 731.90) | 3-10 | m/z = 728.29($C_{53}H_{36}N_4$ = 728.88) |
| 3-11 | m/z = 576.23($C_{41}H_{28}N_4$ = 576.69) | 3-12 | m/z = 651.27($C_{48}H_{33}N_3$ = 651.80) |
| 3-13 | m/z = 727.30($C_{54}H_{37}N_3$ = 727.89) | 3-14 | m/z = 777.31($C_{58}H_{39}N_3$ = 777.95) |
| 3-15 | m/z = 827.33($C_{62}H_{41}N_3$ = 828.01) | 3-16 | m/z = 1031.42($C_{78}H_{53}N_3$ = 1032.28) |
| 3-17 | m/z = 843.36($C_{63}H_{45}N_3$ = 844.05) | 3-18 | m/z = 967.39($C_{73}H_{49}N_3$ = 968.19) |
| 3-19 | m/z = 965.38($C_{73}H_{47}N_3$ = 966.17) | 3-20 | m/z = 833.29($C_{60}H_{39}N_3S$ = 834.04) |
| 3-21 | m/z = 833.29($C_{60}H_{39}N_3S$ = 834.04) | 3-22 | m/z = 880.36($C_{65}H_{44}N_4$ = 881.07) |
| 3-23 | m/z = 728.29($C_{53}H_{36}N_4$ = 728.88) | 3-24 | m/z = 805.32($C_{58}H_{39}N_5$ = 805.96) |
| 3-25 | m/z = 939.27($C_{66}H_{41}N_3S_2$ = 940.18) | 3-26 | m/z = 959.42($C_{72}H_{53}N_3$ = 960.21) |
| 3-27 | m/z = 1207.49($C_{92}H_{61}N_3$ = 1208.49) | 3-28 | m/z = 1207.49($C_{92}H_{61}N_3$ = 1208.49) |
| 4-1 | m/z = 725.28($C_{54}H_{35}N_3$ = 725.88) | 4-2 | m/z = 775.30($C_{58}H_{37}N_3$ = 775.93) |
| 4-3 | m/z = 775.30($C_{58}H_{37}N_3$ = 775.93) | 4-4 | m/z = 801.31($C_{60}H_{39}N_3$ = 801.97) |
| 4-5 | m/z = 726.28($C_{53}H_{34}N_4$ = 726.86) | 4-6 | m/z = 726.28($C_{53}H_{34}N_4$ = 726.86) |
| 4-7 | m/z = 726.28($C_{53}H_{34}N_4$ = 726.86) | 4-8 | m/z = 831.27($C_{60}H_{37}N_3S$ = 832.02) |
| 4-9 | m/z = 977.38($C_{74}H_{47}N_3$ = 978.19) | 4-10 | m/z = 877.35($C_{66}H_{43}N_3$ = 878.07) |
| 4-11 | m/z = 801.31($C_{60}H_{39}N_3$ = 801.97) | 4-12 | m/z = 879.34($C_{64}H_{41}N_5$ = 880.04) |
| 4-13 | m/z = 775.30($C_{58}H_{37}N_3$ = 775.93) | 4-14 | m/z = 825.31($C_{62}H_{39}N_3$ = 825.99) |
| 4-15 | m/z = 825.31($C_{62}H_{39}N_3$ = 825.99) | 4-16 | m/z = 953.38($C_{72}H_{47}N_3$ = 954.16) |
| 5-1 | m/z = 649.25($C_{48}H_{31}N_3$ = 649.78) | 5-2 | m/z = 699.27($C_{52}H_{33}N_3$ = 699.84) |
| 5-3 | m/z = 699.27($C_{52}H_{33}N_3$ = 699.84) | 5-4 | m/z = 725.28($C_{54}H_{35}N_3$ = 725.88) |
| 5-5 | m/z = 650.25($C_{47}H_{30}N_4$ = 650.77) | 5-6 | m/z = 650.25($C_{47}H_{30}N_4$ = 650.77) |
| 5-7 | m/z = 861.23($C_{60}H_{35}N_3S_2$ = 862.07) | 5-8 | m/z = 765.31($C_{57}H_{39}N_3$ = 765.94) |
| 5-9 | m/z = 725.28($C_{54}H_{35}N_3$ = 725.88) | 5-10 | m/z = 725.28($C_{54}H_{35}N_3$ = 725.88) |
| 5-11 | m/z = 801.31($C_{60}H_{39}N_3$ = 801.97) | 5-12 | m/z = 801.31($C_{60}H_{39}N_3$ = 801.97) |
| 5-13 | m/z = 879.34($C_{64}H_{41}N_5$ = 880.04) | 5-14 | m/z = 957.32($C_{70}H_{43}N_3S$ = 958.18) |
| 5-15 | m/z = 851.33($C_{64}H_{41}N_3$ = 852.03) | 5-16 | m/z = 851.33($C_{64}H_{41}N_3$ = 852.03) |
| 6-1 | m/z = 651.27($C_{48}H_{33}N_3$ = 651.80) | 6-2 | m/z = 701.28($C_{52}H_{35}N_3$ = 701.85) |
| 6-3 | m/z = 701.28($C_{52}H_{35}N_3$ = 701.85) | 6-4 | m/z = 803.33($C_{60}H_{41}N_3$ = 803.99) |
| 6-5 | m/z = 767.33($C_{57}H_{41}N_3$ = 767.96) | 6-6 | m/z = 891.36($C_{67}H_{45}N_3$ = 892.09) |
| 6-7 | m/z = 889.35($C_{67}H_{43}N_3$ = 890.08) | 6-8 | m/z = 857.29($C_{62}H_{39}N_3S$ = 858.06) |
| 6-9 | m/z = 757.26($C_{54}H_{35}N_3S$ = 757.94) | 6-10 | m/z = 728.29($C_{53}H_{36}N_4$ = 728.88) |
| 6-11 | m/z = 652.26($C_{47}H_{32}N_4$ = 652.78) | 6-12 | m/z = 757.26(C54H35N3S = 757.94) |
| 7-1 | m/z = 731.24($C_{52}H_{33}N_3S$ = 731.90) | 7-2 | m/z = 728.29($C_{53}H_{36}N_4$ = 728.88) |
| 7-3 | m/z = 576.23($C_{41}H_{28}N_4$ = 576.69) | 7-4 | m/z = 651.27($C_{48}H_{33}N_3$ = 651.80) |
| 7-5 | m/z = 727.30($C_{54}H_{37}N_3$ = 727.89) | 7-6 | m/z = 777.31($C_{58}H_{39}N_3$ = 777.95) |
| 7-7 | m/z = 827.33($C_{62}H_{41}N_3$ = 828.01) | 7-8 | m/z = 1031.42($C_{78}H_{53}N_3$ = 1032.28) |
| 8-1 | m/z = 650.25($C_{47}H_{30}N_4$ = 650.77) | 8-2 | m/z = 650.25($C_{47}H_{30}N_4$ = 650.77) |
| 8-3 | m/z = 861.23($C_{60}H_{35}N_3S_2$ = 862.07) | 8-4 | m/z = 765.31($C_{57}H_{39}N_3$ = 765.94) |
| 8-5 | m/z = 725.28($C_{54}H_{35}N_3$ = 725.88) | 8-6 | m/z = 725.28($C_{54}H_{35}N_3$ = 725.88) |
| 8-7 | m/z = 801.31($C_{60}H_{39}N_3$ = 801.97) | 8-8 | m/z = 801.31($C_{60}H_{39}N_3$ = 801.97) |

Fabrication and Evaluation of Organic Electronic Element

Example 1

Green OLED (an Emission-auxiliary Layer)

Organic light emitting diodes (OLEDs) were fabricated according to a conventional method by using a compound of the present invention as an emission-auxiliary layer material.

First, an ITO layer (anode) was formed on a glass substrate, and then 4,4',4''-tris[2-naphthyl(phenyl)amino]triphenylamine (hereinafter, "2-TNATA") was vacuum-deposited on the ITO layer to form a hole injection layer with a thickness of 60 nm.

Subsequently, N,N'-Bis(1-naphthalenyl)-N,N'-bis-phenyl-(1,1'-biphenyl)-4,4'-diamine (hereinafter, "NPB") was vacuum-deposited with a thickness of 60 nm on the hole injection layer to form a hole transport layer.

Subsequently, compound 1-1 of the present invention was vacuum-deposited on the hole transport layer to form a emission-auxiliary layer with a thickness of 20 nm.

A light emitting layer with a thickness of 30 nm was deposited on the emission-auxiliary layer by using 4,4'-N,N'-dicarbazole-biphenyl (hereinafter, "CBP") as a host material and tris(2-phenylpyridine)-iridium (hereinafter, "Ir(ppy)₃") as a dopant material in a weight ratio of 95:5.

Next, (1,1'-biphenyl-4-olato)bis(2-methyl-8-quinolinolato)aluminum (hereinafter, "BAlq") was vacuum-deposited with a thickness of 10 nm on the light emitting layer to form a hole blocking layer, and tris-(8-hydroxyquinoline)aluminum (hereinafter, "Alq₃") was vacuum-deposited with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Example 2 to Example 28

Green OLED (an Emission-auxiliary Layer)

The OLEDs were fabricated in the same manner as described in Example 1 except that any one of the inventive compounds described in Table 4 instead of the inventive compound 1-1 was used as an emission-auxiliary layer material.

Comparative Example 1

The OLED was fabricated in the same manner as described in Example 1 except that an emission-auxiliary layer was not formed.

Comparative Example 2 to Comparative Example 9

The OLEDs were fabricated in the same manner as described in Example 1 except that any one of Comparative compounds 1 to 8 instead of the inventive compound 1-1 was used as an emission-auxiliary layer material.
<Comp.compd 1> <Comp.compd 2> <Comp.compd 3> <Comp.compd 4>

<Comp. compd 5>

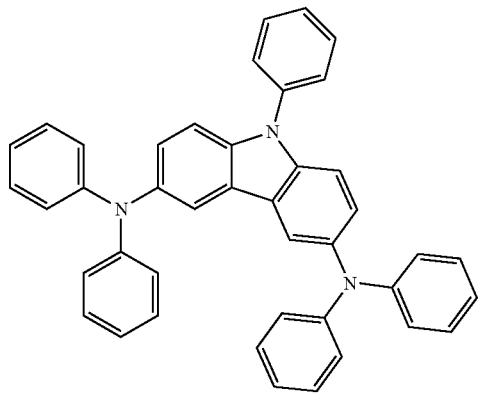

<Comp. compd 6>

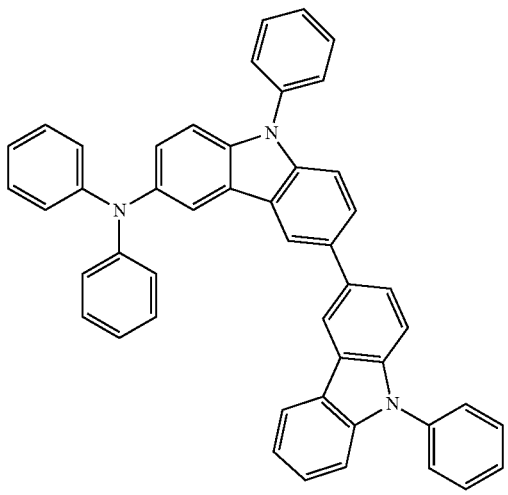

<Comp. compd 7>

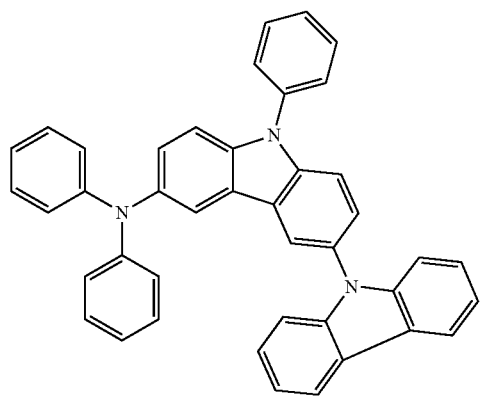

<Comp. compd 8>

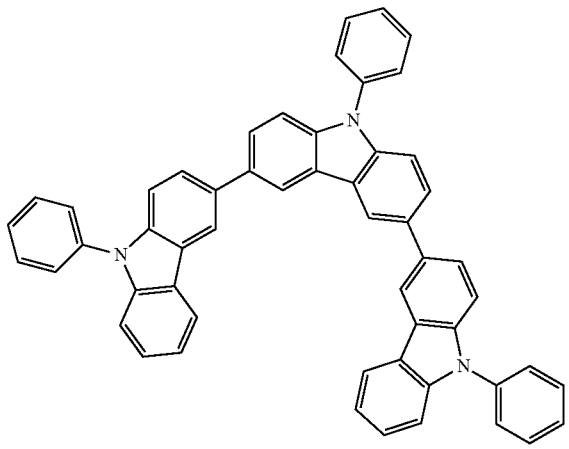

Electroluminescence (EL) characteristics were measured with a PR-650(Photoresearch) by applying a forward bias DC voltage to the OLEDs prepared in Examples 1 to 28 of the present invention and Comparative Examples 1 to 9. And, the T95 life span was measured using a life span measuring apparatus manufactured by Macscience Inc. at reference brightness of 5000 cd/m². The measurement results are shown in Table 4 below.

TABLE 4

| EAL com. | | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(1) | — | 5.9 | 14.0 | 5000.0 | 35.6 | 77.1 | 0.33 | 0.61 |
| comp. Ex(2) | comp. Com1 | 6.2 | 12.4 | 5000.0 | 40.2 | 111.6 | 0.33 | 0.61 |
| comp. Ex(3) | comp. Com2 | 6.1 | 11.9 | 5000.0 | 41.9 | 102.3 | 0.33 | 0.61 |
| comp. Ex(4) | comp. Com3 | 6.1 | 12.1 | 5000.0 | 41.3 | 111.9 | 0.33 | 0.61 |
| comp. Ex(5) | comp. Com4 | 6.3 | 10.6 | 5000.0 | 47.2 | 102.4 | 0.33 | 0.61 |
| comp. Ex(6) | comp. Com5 | 6.1 | 10.6 | 5000.0 | 47.2 | 107.6 | 0.33 | 0.62 |
| comp. Ex(7) | comp. Com6 | 6.0 | 11.1 | 5000.0 | 45.0 | 118.3 | 0.33 | 0.61 |
| comp. Ex(8) | comp. Com7 | 6.3 | 11.4 | 5000.0 | 43.9 | 110.9 | 0.33 | 0.61 |
| comp. Ex(9) | comp. Com8 | 6.2 | 10.2 | 5000.0 | 49.2 | 119.3 | 0.33 | 0.62 |
| Ex. (1) | 1-1 | 6.1 | 9.2 | 5000.0 | 54.5 | 123.9 | 0.33 | 0.62 |
| Ex. (2) | 1-8 | 5.9 | 9.4 | 5000.0 | 53.1 | 123.5 | 0.33 | 0.62 |
| Ex. (3) | 1-9 | 6.0 | 9.2 | 5000.0 | 54.5 | 132.9 | 0.33 | 0.61 |
| Ex. (4) | 1-12 | 6.0 | 9.4 | 5000.0 | 53.5 | 135.9 | 0.33 | 0.61 |
| Ex. (5) | 1-13 | 6.2 | 9.2 | 5000.0 | 54.1 | 125.1 | 0.33 | 0.62 |
| Ex. (6) | 2-1 | 6.1 | 9.0 | 5000.0 | 55.8 | 128.6 | 0.33 | 0.61 |
| Ex. (7) | 2-7 | 6.2 | 8.8 | 5000.0 | 56.9 | 140.8 | 0.33 | 0.62 |
| Ex. (8) | 2-10 | 6.1 | 8.8 | 5000.0 | 56.7 | 130.3 | 0.33 | 0.62 |
| Ex. (9) | 2-14 | 5.9 | 8.9 | 5000.0 | 56.4 | 140.8 | 0.33 | 0.62 |
| Ex. (10) | 2-23 | 6.0 | 8.9 | 5000.0 | 56.3 | 131.8 | 0.33 | 0.61 |
| Ex. (11) | 3-4 | 6.1 | 8.8 | 5000.0 | 56.7 | 146.7 | 0.33 | 0.62 |
| Ex. (12) | 3-8 | 6.1 | 8.9 | 5000.0 | 56.3 | 125.8 | 0.33 | 0.61 |
| Ex. (13) | 3-10 | 6.3 | 8.9 | 5000.0 | 56.4 | 124.2 | 0.33 | 0.62 |
| Ex. (14) | 3-13 | 6.0 | 9.0 | 5000.0 | 55.8 | 131.1 | 0.33 | 0.61 |
| Ex. (15) | 3-25 | 6.0 | 8.9 | 5000.0 | 56.1 | 144.2 | 0.33 | 0.61 |
| Ex. (16) | 4-1 | 5.9 | 7.9 | 5000.0 | 63.6 | 142.8 | 0.33 | 0.62 |
| Ex. (17) | 4-6 | 6.1 | 7.7 | 5000.0 | 65.0 | 147.5 | 0.33 | 0.61 |
| Ex. (18) | 4-11 | 6.2 | 7.8 | 5000.0 | 64.1 | 140.8 | 0.33 | 0.61 |
| Ex. (19) | 5-4 | 6.0 | 8.0 | 5000.0 | 62.3 | 148.7 | 0.33 | 0.62 |
| Ex. (20) | 5-12 | 6.2 | 8.0 | 5000.0 | 62.7 | 124.2 | 0.33 | 0.61 |
| Ex. (21) | 5-16 | 6.2 | 8.0 | 5000.0 | 62.6 | 124.6 | 0.33 | 0.61 |
| Ex. (22) | 6-1 | 6.3 | 8.1 | 5000.0 | 61.7 | 149.5 | 0.33 | 0.62 |
| Ex. (23) | 6-7 | 6.3 | 8.1 | 5000.0 | 61.8 | 148.1 | 0.33 | 0.61 |
| Ex. (24) | 6-12 | 6.1 | 8.1 | 5000.0 | 61.5 | 129.8 | 0.33 | 0.62 |
| Ex. (25) | 7-3 | 6.0 | 8.7 | 5000.0 | 57.4 | 135.1 | 0.33 | 0.62 |
| Ex. (26) | 7-5 | 6.1 | 8.6 | 5000.0 | 58.3 | 147.5 | 0.33 | 0.61 |
| Ex. (27) | 8-5 | 6.2 | 8.4 | 5000.0 | 59.3 | 128.9 | 0.33 | 0.61 |
| Ex. (28) | 8-8 | 5.9 | 8.8 | 5000.0 | 57.1 | 145.7 | 0.33 | 0.61 |

Example 29

Red OLED (an Emission-auxiliary Layer)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, NPB was vacuum-deposited with a thickness of 60 nm on the hole injection layer to form a hole transport layer.

Subsequently, the compound 1-2 of the present invention was vacuum-deposited on the hole transport layer to form a emission-auxiliary layer with a thickness of 20 nm.

A light emitting layer with a thickness of 30 nm was deposited on the emission-auxiliary layer by using the CBP as a host material and bis-(1-phenylisoquinolyl)iridium(III) acetylacetonate ("(piq)$_2$Ir(acac)") as a dopant material in a weight ratio of 95:5.

Next, BAlq was vacuum-deposited with a thickness of 10 nm on the light emitting layer to form a hole blocking layer, Alq$_3$ was vacuum-deposited with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Example 30 to Example 56

Red OLED (an Emission-auxiliary Layer)

The OLEDs were fabricated in the same manner as described in Example 29 except that any one of the inventive compounds described in Table 5 instead of the inventive compound 1-2 was used as an emission-auxiliary layer material.

Comparative Example 10

The OLED was fabricated in the same manner as described in Example 29 except that an emission-auxiliary layer was not formed.

Comparative Example 11 to Comparative Example 18

The OLEDs were fabricated in the same manner as described in Example 29 except that any one of Comparative compounds 1 to 8 above instead of the inventive compound 1-2 was used as an emission-auxiliary layer material.

Electroluminescence (EL) characteristics were measured with a PR-650(Photoresearch) by applying a forward bias DC voltage to the OLEDs prepared in Examples 29 to 59 of the present invention and Comparative Examples 10 to 18. And, the T95 life span was measured using a life span measuring apparatus manufactured by Macscience Inc. at reference brightness of 2500 cd/m². The measurement results are shown in Table 5 below.

material showed the highest luminescent efficiency and life span, wherein a carbazole group of the Compound 8 is substituted with a N-carbazole group at positions 1 and 3 of the carbazole group, and a carbazole group of the compound of the present invention is substituted with arylamine or a

TABLE 5

| | EAL com. | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex(10) | — | 6.2 | 32.9 | 2500.0 | 7.6 | 84.9 | 0.66 | 0.34 |
| comp. Ex(11) | comp. Com1 | 6.3 | 30.7 | 2500.0 | 8.2 | 105.1 | 0.65 | 0.34 |
| comp. Ex(12) | comp. Com2 | 6.3 | 30.4 | 2500.0 | 8.2 | 101.7 | 0.66 | 0.32 |
| comp. Ex(13) | comp. Com3 | 6.3 | 30.3 | 2500.0 | 8.3 | 116.0 | 0.67 | 0.34 |
| comp. Ex(14) | comp. Com4 | 6.3 | 30.7 | 2500.0 | 8.2 | 105.8 | 0.66 | 0.33 |
| comp. Ex(15) | comp. Com5 | 6.2 | 26.8 | 2500.0 | 9.3 | 116.7 | 0.66 | 0.33 |
| comp. Ex(16) | comp. Com6 | 6.3 | 26.8 | 2500.0 | 9.3 | 110.4 | 0.66 | 0.33 |
| comp. Ex(17) | comp. Com7 | 6.4 | 28.5 | 2500.0 | 8.8 | 115.7 | 0.66 | 0.32 |
| comp. Ex(18) | comp. Com8 | 6.3 | 25.3 | 2500.0 | 9.9 | 118.7 | 0.66 | 0.33 |
| Ex. (29) | 1-2 | 6.2 | 18.4 | 2500.0 | 13.6 | 123.9 | 0.67 | 0.33 |
| Ex. (30) | 1-10 | 6.2 | 18.9 | 2500.0 | 13.2 | 123.5 | 0.66 | 0.34 |
| Ex. (31) | 1-11 | 6.2 | 18.9 | 2500.0 | 13.2 | 132.9 | 0.67 | 0.34 |
| Ex. (32) | 1-14 | 6.3 | 18.1 | 2500.0 | 13.8 | 135.9 | 0.66 | 0.33 |
| Ex. (33) | 1-17 | 6.2 | 18.4 | 2500.0 | 13.6 | 125.1 | 0.66 | 0.32 |
| Ex. (34) | 2-2 | 6.4 | 16.4 | 2500.0 | 15.3 | 128.6 | 0.67 | 0.34 |
| Ex. (35) | 2-8 | 6.3 | 16.4 | 2500.0 | 15.2 | 140.8 | 0.65 | 0.33 |
| Ex. (36) | 2-11 | 6.3 | 16.5 | 2500.0 | 15.1 | 130.3 | 0.66 | 0.34 |
| Ex. (37) | 2-15 | 6.3 | 16.0 | 2500.0 | 15.6 | 140.8 | 0.67 | 0.33 |
| Ex. (38) | 2-24 | 6.3 | 16.6 | 2500.0 | 15.0 | 131.8 | 0.67 | 0.34 |
| Ex. (39) | 3-5 | 6.4 | 16.3 | 2500.0 | 15.4 | 146.7 | 0.67 | 0.33 |
| Ex. (40) | 3-9 | 6.3 | 16.0 | 2500.0 | 15.6 | 125.8 | 0.67 | 0.32 |
| Ex. (41) | 3-11 | 6.2 | 16.1 | 2500.0 | 15.5 | 124.2 | 0.66 | 0.33 |
| Ex. (42) | 3-14 | 6.3 | 16.3 | 2500.0 | 15.3 | 131.1 | 0.67 | 0.33 |
| Ex. (43) | 3-26 | 6.3 | 16.8 | 2500.0 | 14.9 | 144.2 | 0.66 | 0.34 |
| Ex. (44) | 4-2 | 6.4 | 12.2 | 2500.0 | 20.5 | 142.8 | 0.66 | 0.33 |
| Ex. (45) | 4-5 | 6.3 | 12.3 | 2500.0 | 20.3 | 147.5 | 0.66 | 0.33 |
| Ex. (46) | 4-10 | 6.3 | 12.1 | 2500.0 | 20.7 | 140.8 | 0.65 | 0.32 |
| Ex. (47) | 5-5 | 6.2 | 13.3 | 2500.0 | 18.8 | 148.7 | 0.65 | 0.34 |
| Ex. (48) | 5-13 | 6.3 | 13.2 | 2500.0 | 19.0 | 124.2 | 0.66 | 0.32 |
| Ex. (49) | 5-17 | 6.4 | 13.6 | 2500.0 | 18.3 | 124.6 | 0.66 | 0.33 |
| Ex. (50) | 6-3 | 6.4 | 13.3 | 2500.0 | 18.8 | 149.5 | 0.66 | 0.32 |
| Ex. (51) | 6-8 | 6.3 | 13.7 | 2500.0 | 18.2 | 148.1 | 0.66 | 0.34 |
| Ex. (52) | 6-15 | 6.2 | 13.7 | 2500.0 | 18.2 | 129.8 | 0.66 | 0.33 |
| Ex. (53) | 7-4 | 6.2 | 15.3 | 2500.0 | 16.3 | 135.1 | 0.65 | 0.32 |
| Ex. (54) | 7-6 | 6.3 | 14.2 | 2500.0 | 17.6 | 147.5 | 0.67 | 0.34 |
| Ex. (55) | 8-3 | 6.3 | 14.9 | 2500.0 | 16.8 | 128.9 | 0.65 | 0.33 |
| Ex. (56) | 8-10 | 6.2 | 14.3 | 2500.0 | 17.5 | 145.7 | 0.66 | 0.32 |

As can be seen from the results of the OLEDs measurements in Tables 4 and 5, it can be confirmed that the luminescent efficiency and life span of the OLEDs employing the inventive compound as an emission-auxiliary layer material were remarkably improved as compared with the OLEDs employing Comparative Compounds 1 to 8 as the hole transport layer material and not forming an emission-auxiliary layer.

It can be confirmed that the the OLEDs comprising an emission-auxiliary layer has a driving voltage slightly higher than that of the OLEDs (Comparative Example 1 and Comparative Example 10) not forming an emission-auxiliary layer, but the luminescent efficiency and life span are remarkably improved.

Further, it was confirmed that the OLEDs (Comparative Example 9 and Comparative Example 18) employing Compound 8 as an emission-auxiliary layer material showed better results than the OLEDs (Comparative Examples 2 to 8, and Comparative Examples 11 to 17) employing Comparative Compound 1 to Comparative Compound 7, and the OLEDs employing a compound according to one embodiment of the present invention as an emission-auxiliary layer carbazole group except for a N-carbazole group at positions 1 and 3 of the carbazole group.

It is judged that this is because a compound wherein two substituents are substituted in one benzene ring of the carbazole group, that is, a compound substituted with an amine group or a carbazole group at positions 1 and 3 of the carbazole group, has a higher T1 and a deeper HOMO level than Comparative Compounds 1 to 7, wherein both benzene rings of the carbazole group of Comparative Compounds 1 to 7 are substituted with an amine group or a carbazole group, as a result, he electron blocking ability and the charge balance in the light emitting layer of holes and electrons are increased to efficiently emit light in the light emitting layer not the interface of the hole transport layer, thereby maximizing the efficiency and lifetime.

In addition, from the fact that the OLEDs employing the compound of the present invention have a better results than Comparative Compounds 8, wherein the Comparative Compounds is substituted with N-carbazole groups at positions 1 and 3 of the carbazole group, it is suggested that the physical properties of the compound and the results of element evaluation may be significantly different depending on the the type of substituent group as well as the position of the substituent group in the carbazole group.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

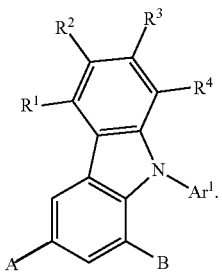

[Formula 1]

wherein
one of A and B is a compound of Formula 1-1 and the other is a compound of Formula 1-2 or Formula 1-3, with the proviso that the compound where $Ar^1$ to $Ar^3$ are phenyl and $L^1$ is m-phenylene when one of A and B is Formula 1-1 is excluded:

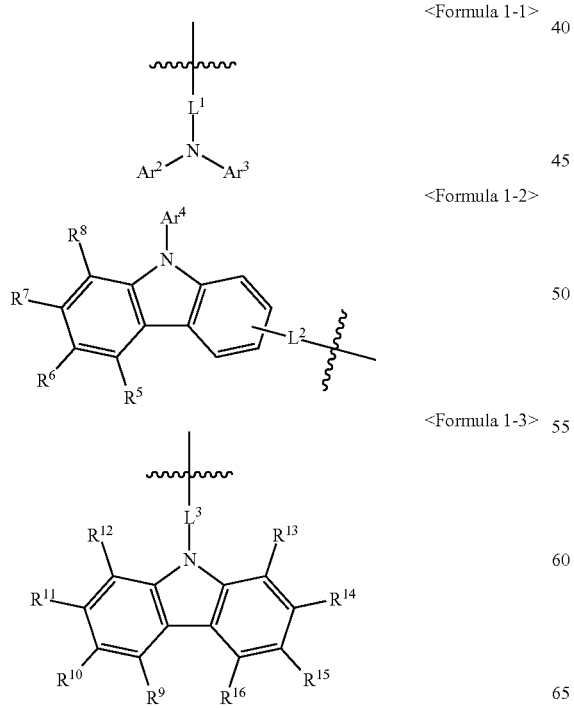

<Formula 1-1>

<Formula 1-2>

<Formula 1-3>

$Ar_1$ to $Ar^4$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; —L'—N($R^a$)($R^b$); and the combination thereof, $L^1$ to $L^3$ are each independently selected from the group consisting of a single bond; a $C_6$-$C_{60}$ arylene group; a fluorenylene group; a fused ring formed by a $C_6$-$C_{60}$ aromatic ring and a $C_3$-$C_{60}$ aliphatic ring; a $C_2$-$C_{60}$ heterocyclic group containing at least one heteroatom selected from the group consisting of O, N, S, Si, and P; and the combination thereof, $R^1$ to $R^{16}$ are each independently i) selected from the group consisting of hydrogen; deuterium; halogen; a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; —L'—N($R^a$)($R^b$); and the combination thereof, or ii) neighboring groups of $R^1$s to $R^{16}$s may be linked to each other to form a ring together with a benzene ring to which they are bonded, and wherein $R^1$s to $R^{16}$s not forming a ring are each the same as defined in the above i), L' is selected from the group consisting of a single bond; a $C_6$-$C_{60}$ arylene group; a fluorenylene group; a fused ring formed by a $C_6$-$C_{60}$ aromatic ring and a $C_3$-$C_{60}$ aliphatic ring; and a $C_2$-$C_{60}$ heterocyclic group containing at least one heteroatom selected from the group consisting of O, N, S, Si, and P, $R^a$ and $R^b$ are each independently selected from the group consisting of a $C_6$-$C_{60}$ aryl group; a fluorenyl group; a fused ring formed by a $C_6$-$C_{60}$ aromatic ring and a $C_3$-$C_{60}$ aliphatic ring; and a $C_2$-$C_{60}$ heterocyclic group containing at least one heteroatom selected from the group consisting of O, N, S, Si and P, and the above aryl group, fluorenyl group, heterocyclic group, fused ring, alkyl group, alkenyl group, alkynyl group, alkoxy group, aryloxy group, arylene group and fluorenylene group may be each substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

2. The compound of claim 1, wherein Formula 1 is represented by one of Formulas 3 to 5 and 8 below:

<Formula 3>
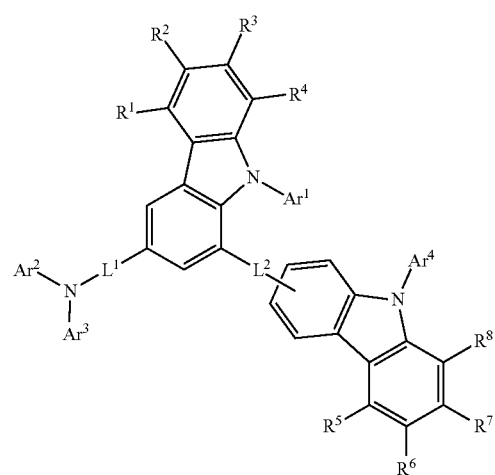
<Formula 4>
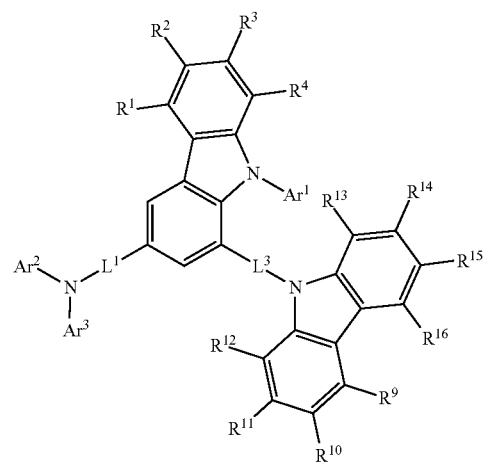
<Formula 5>
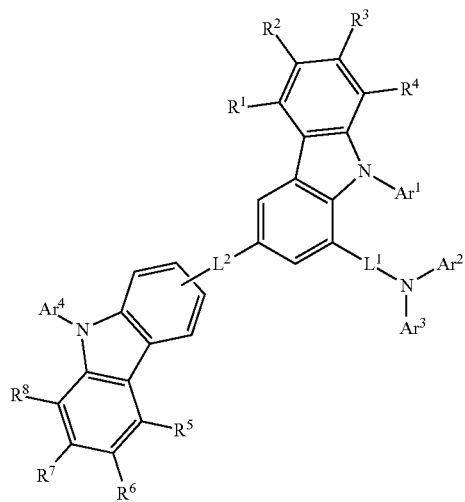
<Formula 8>
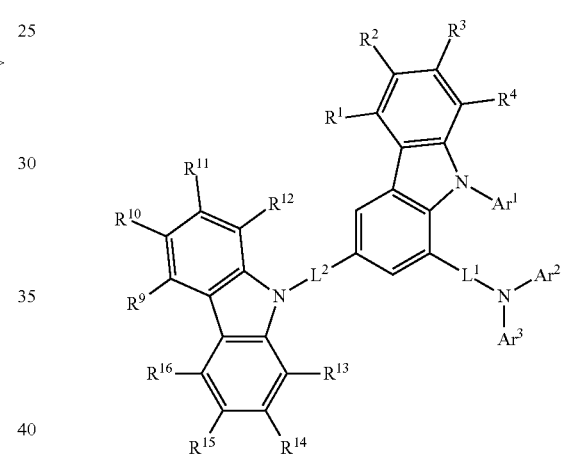
wherein Ar$^1$ to Ar$^4$, L$^1$ to L$^3$ and R$^1$ to R$^{16}$ are each the same as defined in claim 1.
3. The compound of claim 1, wherein Formula 1 is any one of the compounds below:
2-1
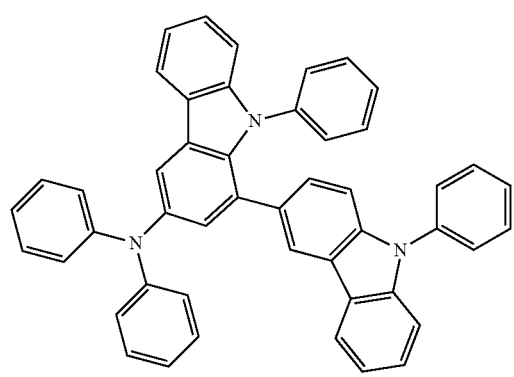
2-2
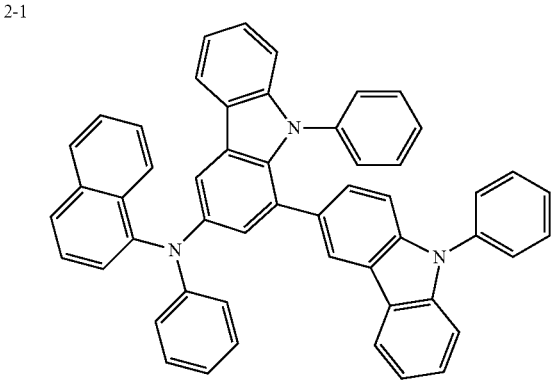

-continued
2-3
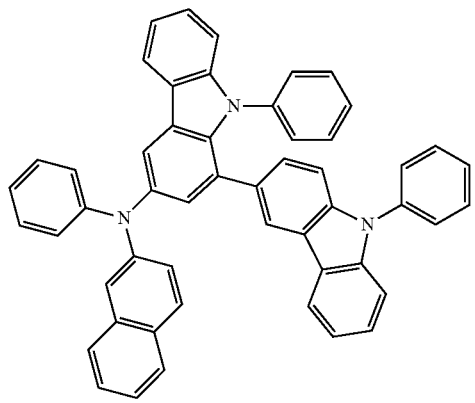
2-4
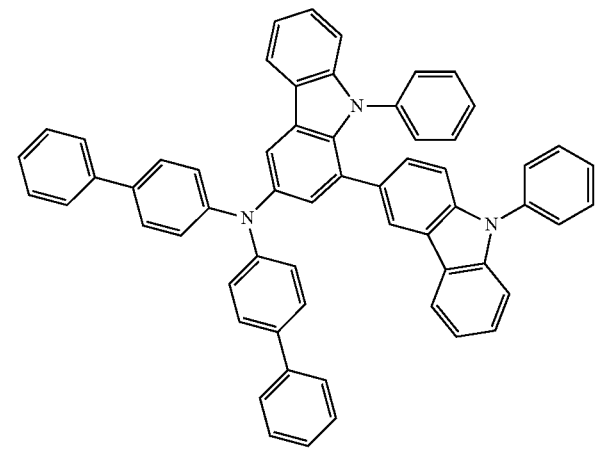
2-5
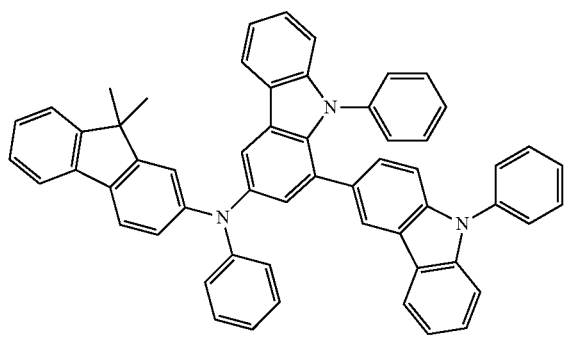
2-6
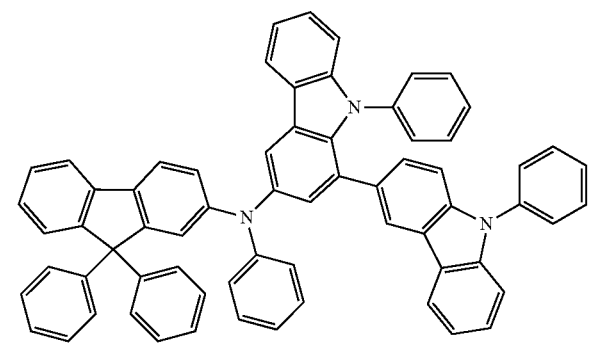
2-7
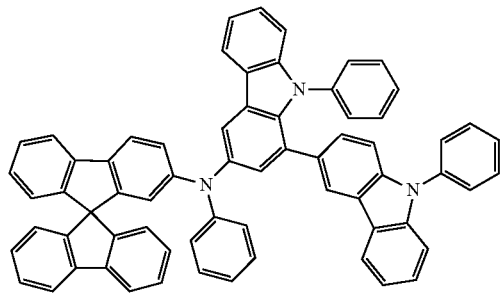
2-8
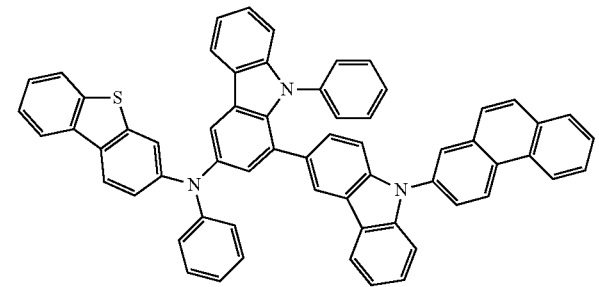
2-9
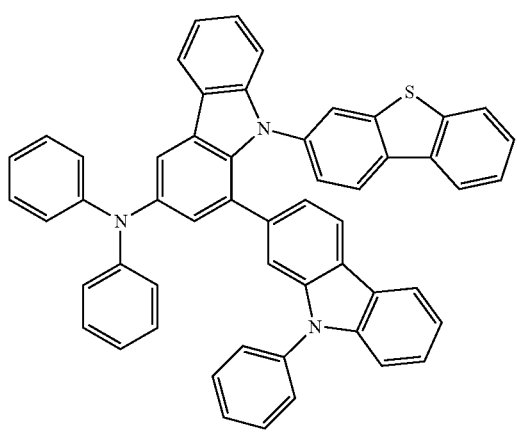
2-10
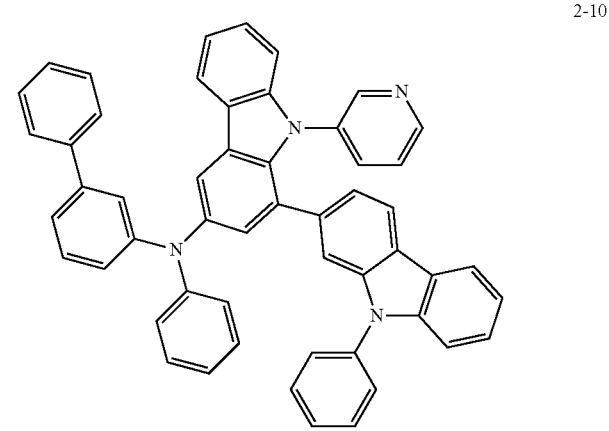

-continued
2-11
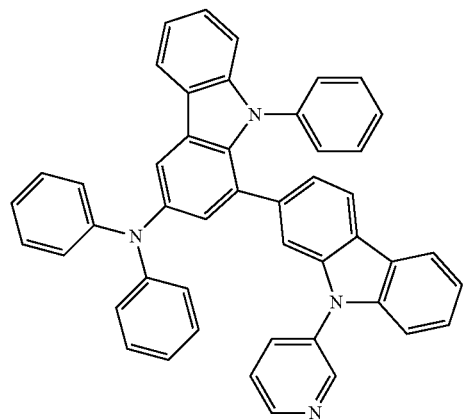
2-12
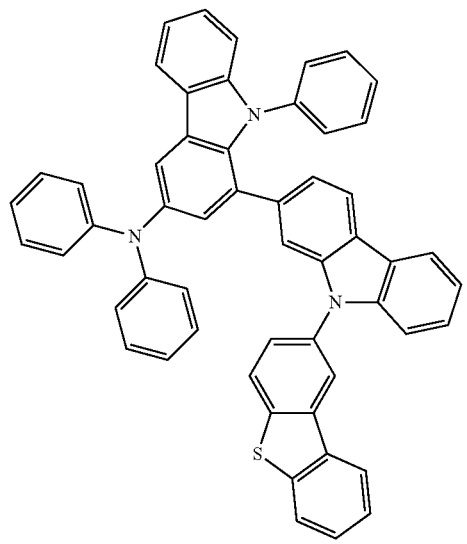
2-13
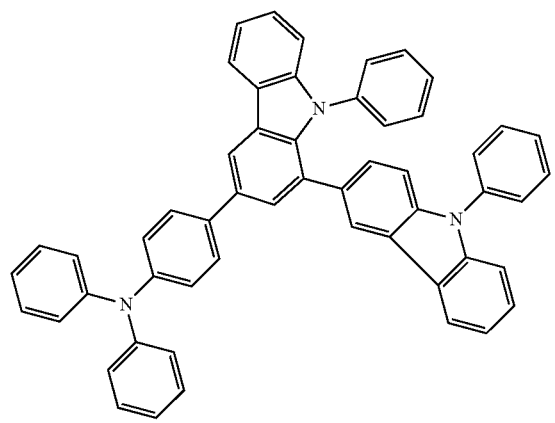
2-14
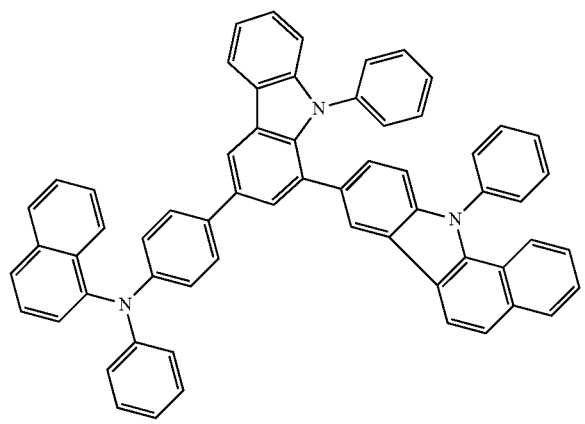
2-15
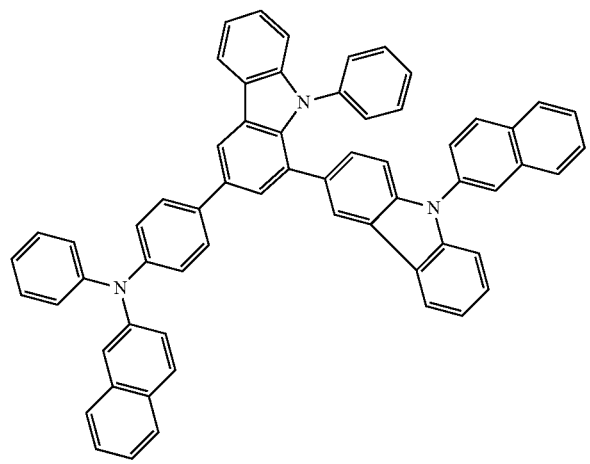

2-16
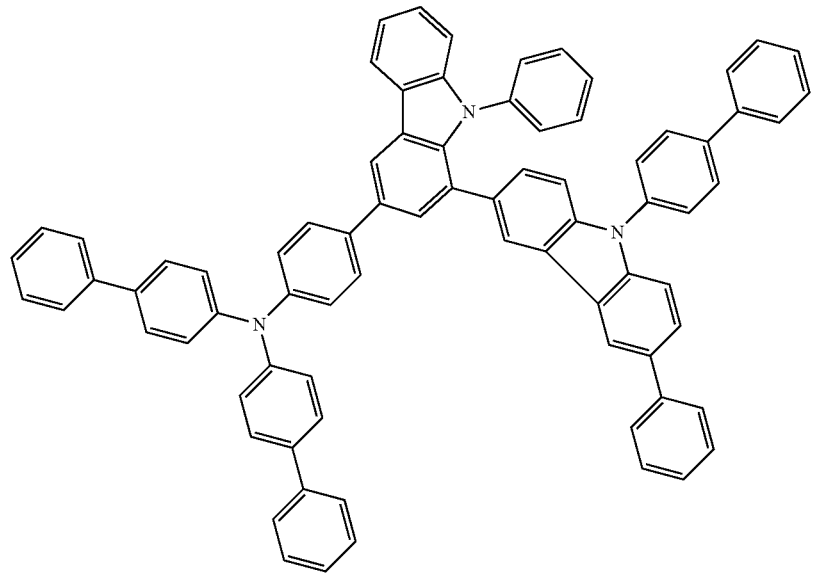
2-17 2-18
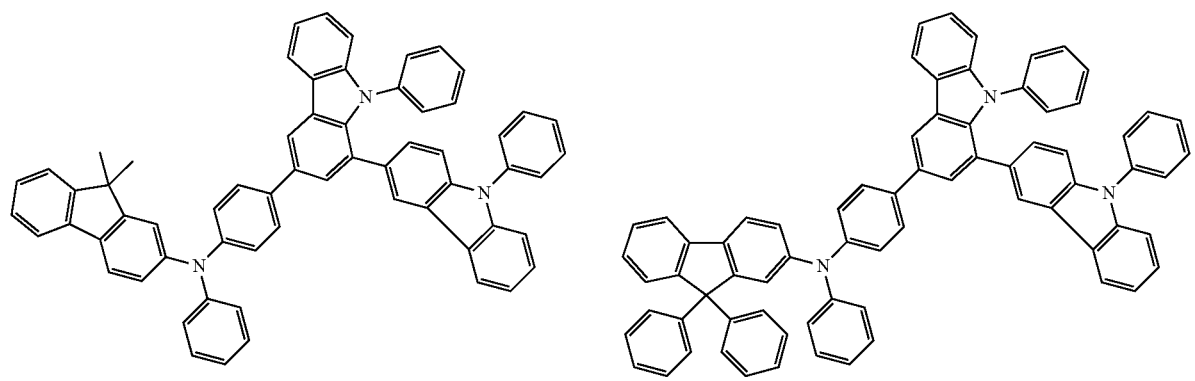
2-19 2-20
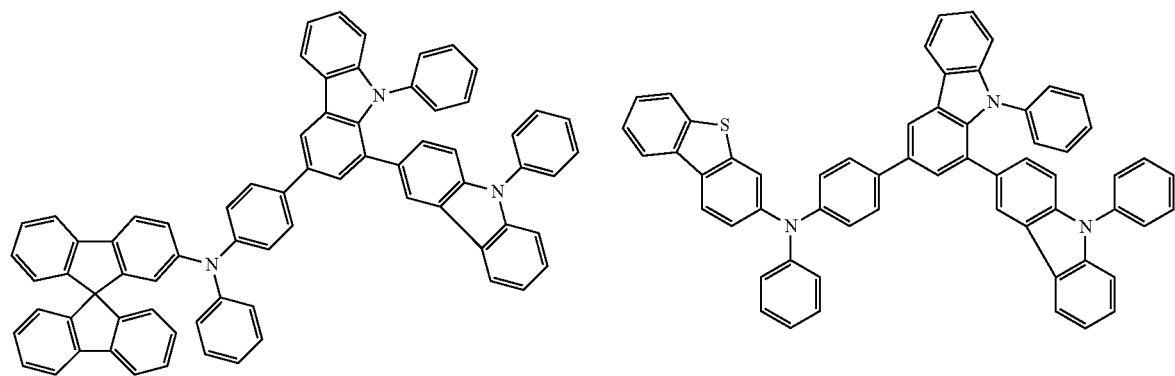

-continued
2-21
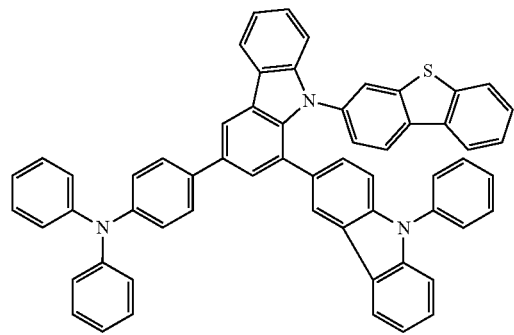
2-22
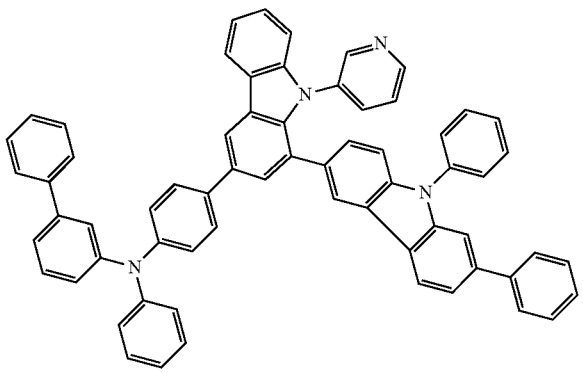
2-23
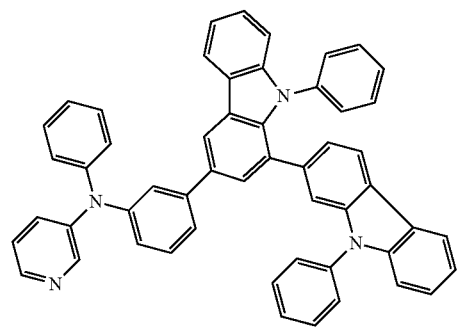
2-24
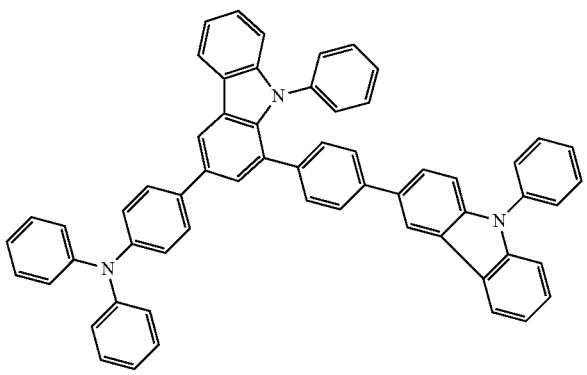
2-25
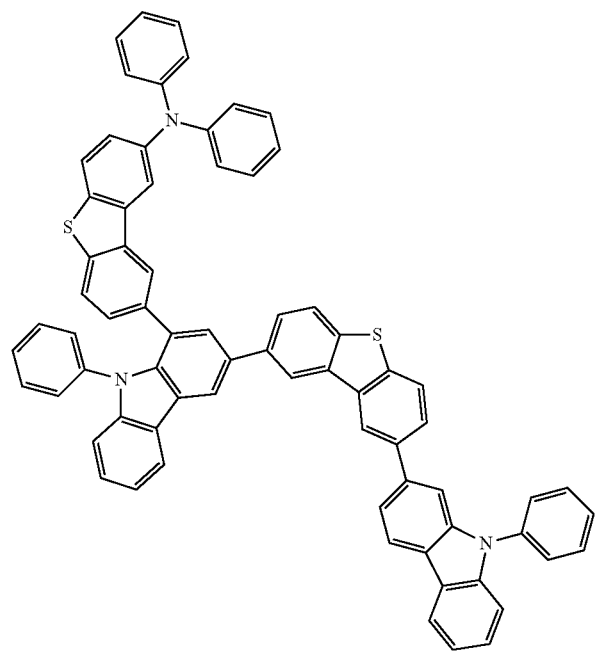
2-26
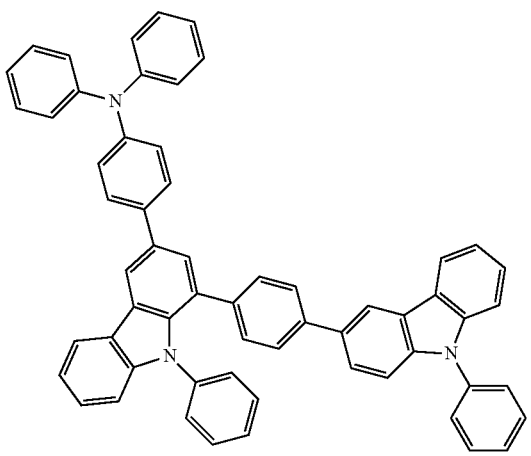

2-27
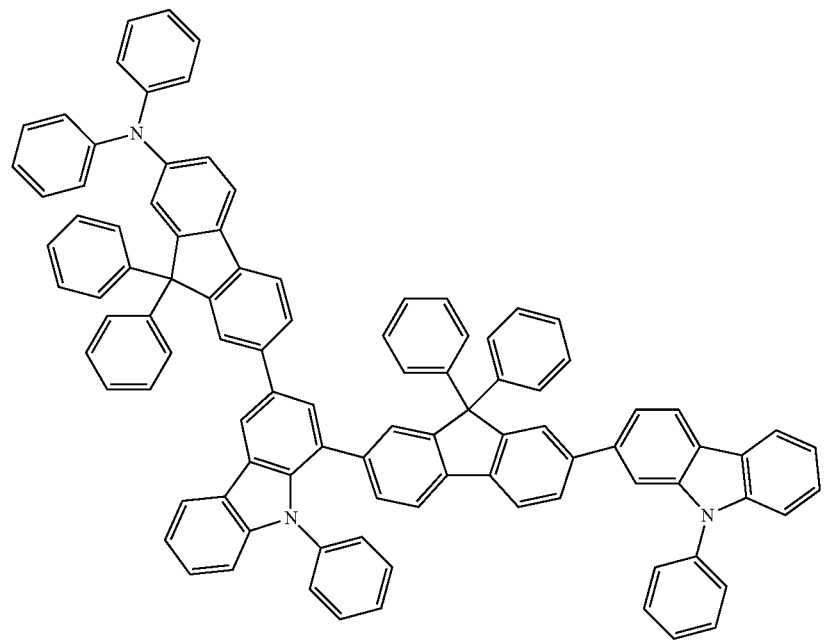
2-28
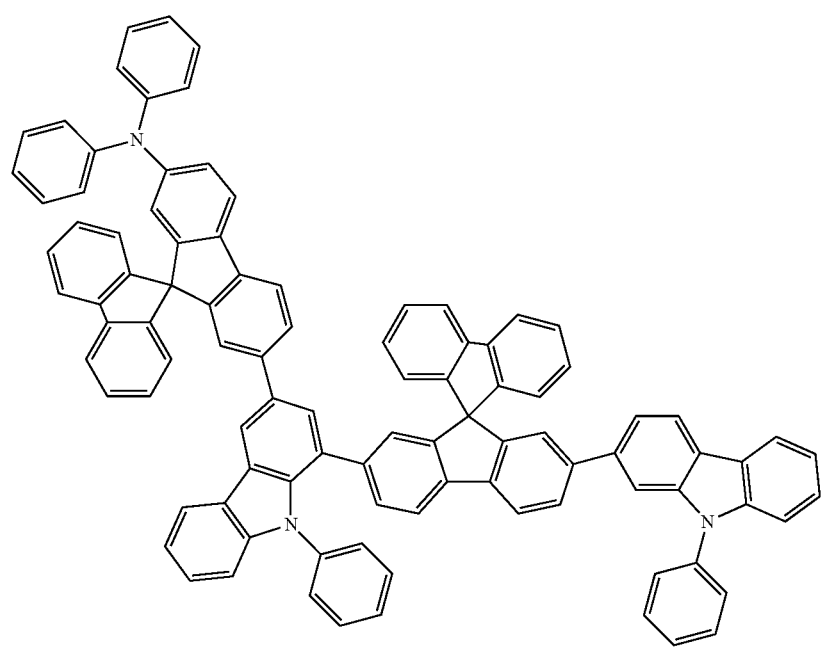
3-1
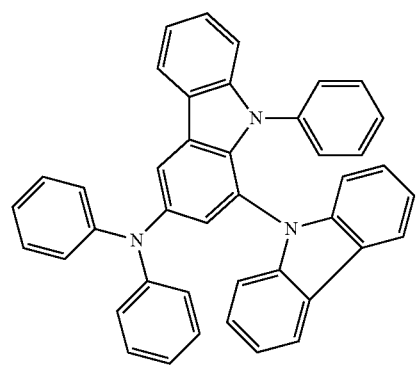
3-2
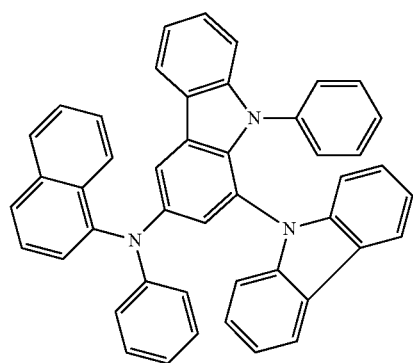

-continued
3-3
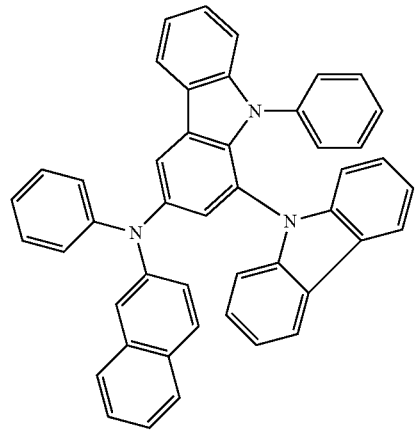
3-4
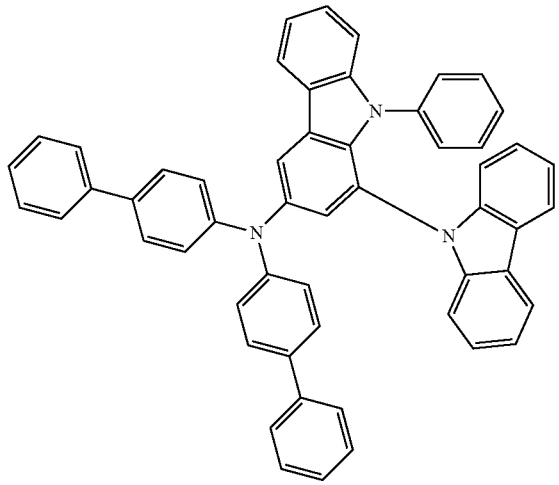
3-5
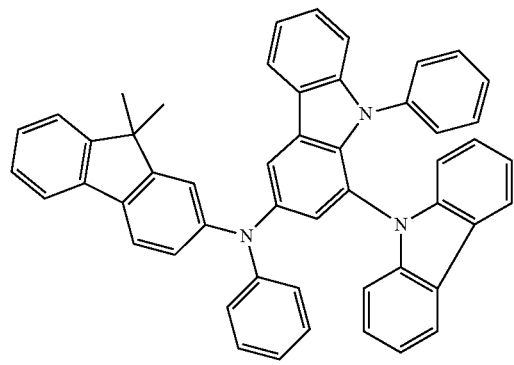
3-6
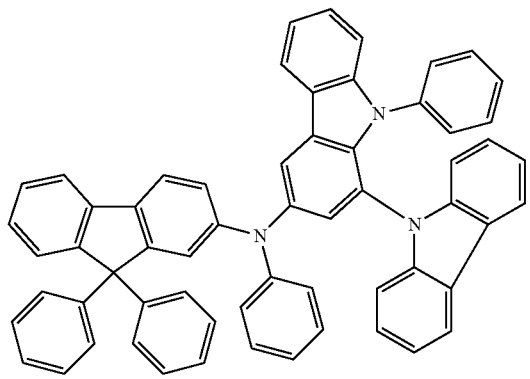
3-7
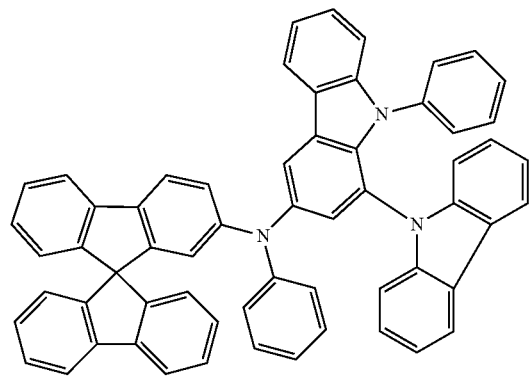
3-8
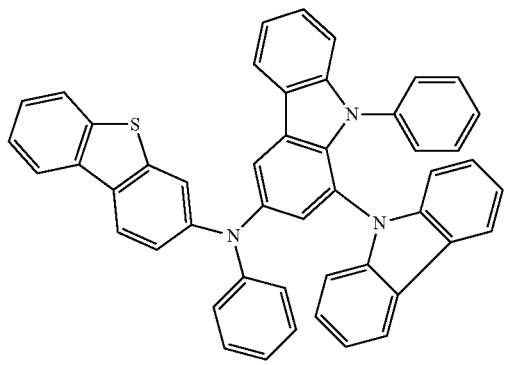

3-9
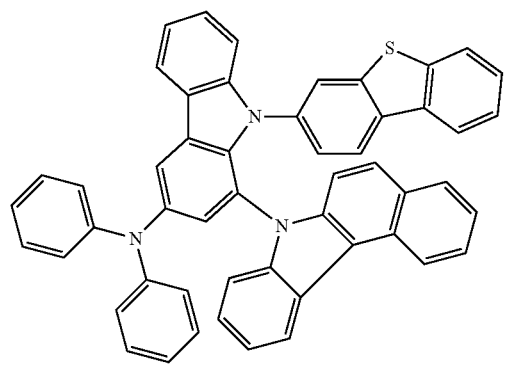
3-10
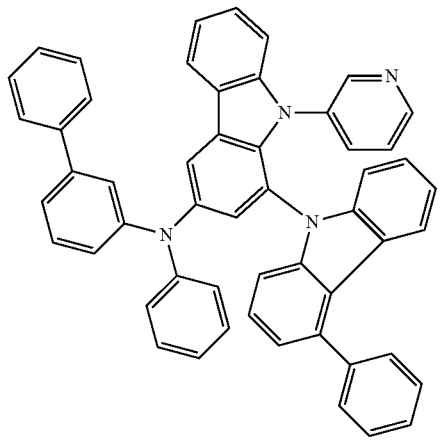
3-11
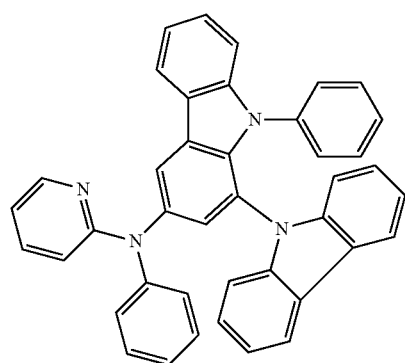
3-12
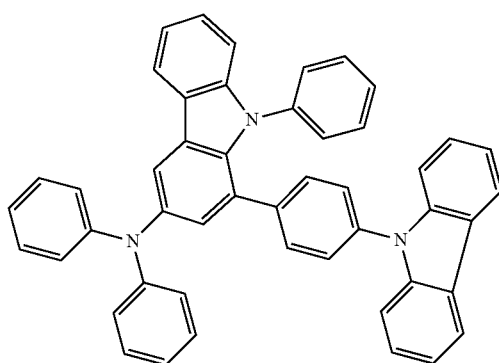
3-13
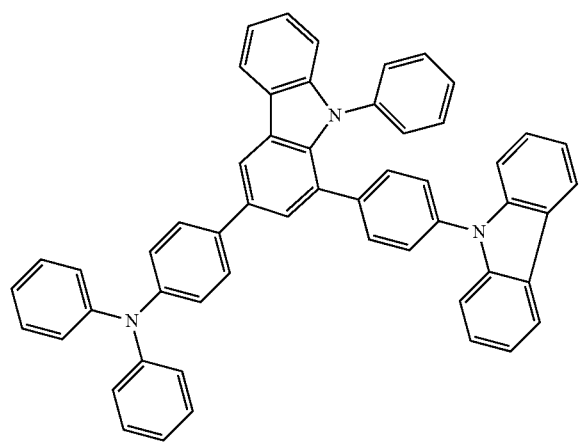
3-14
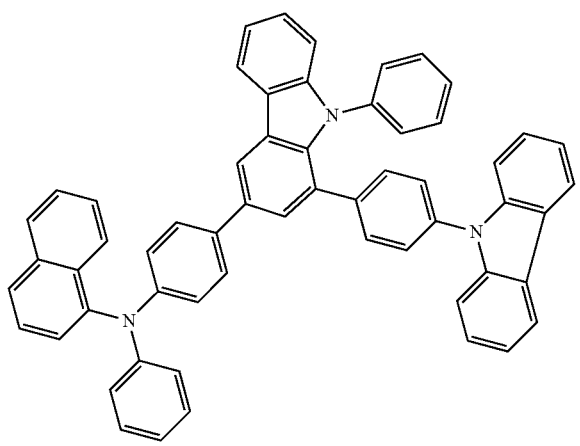

3-15
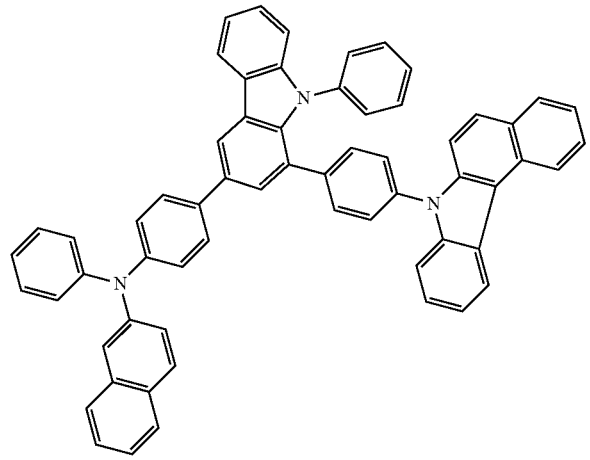
3-16
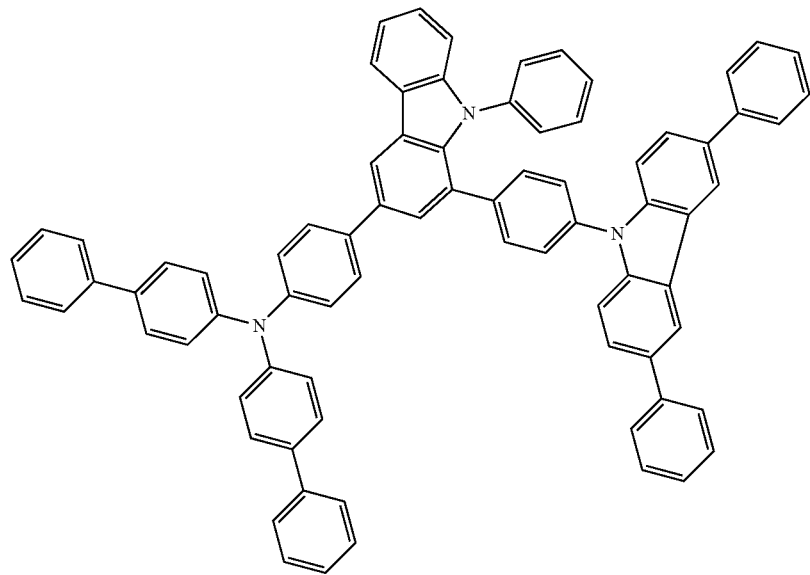
3-17
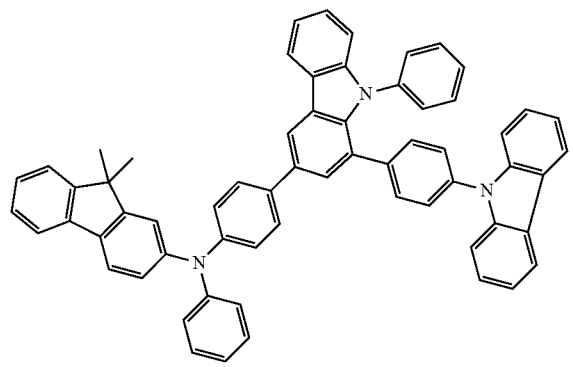
3-18
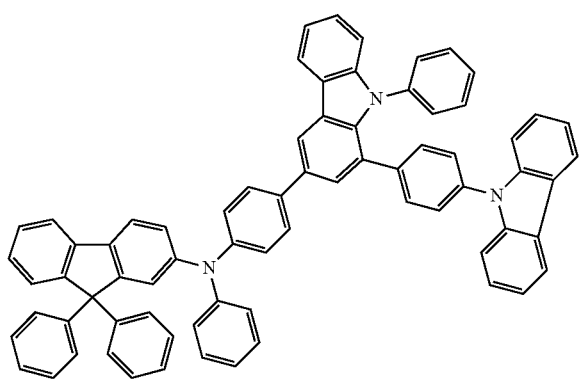

-continued
3-19
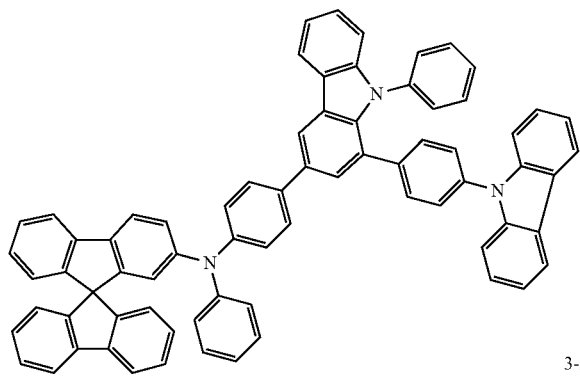
3-20
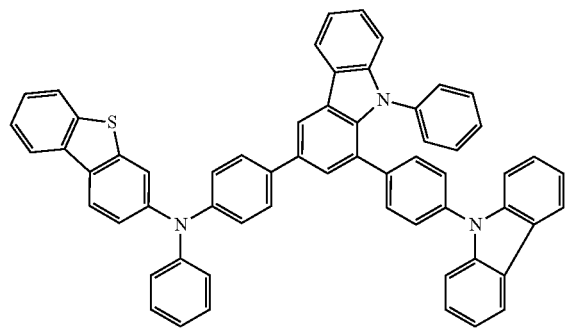
3-21
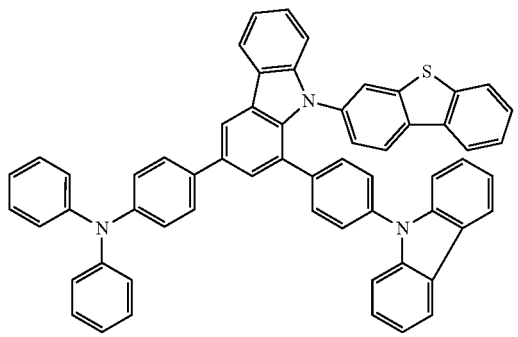
3-22
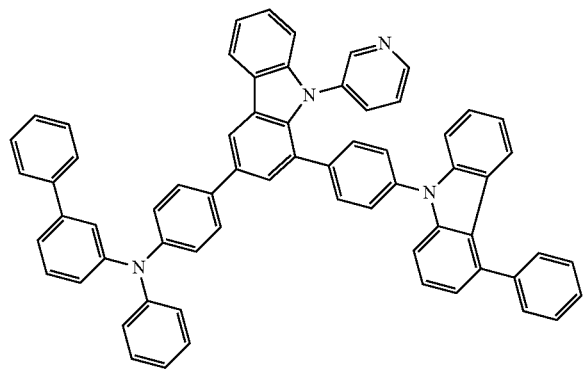
3-23
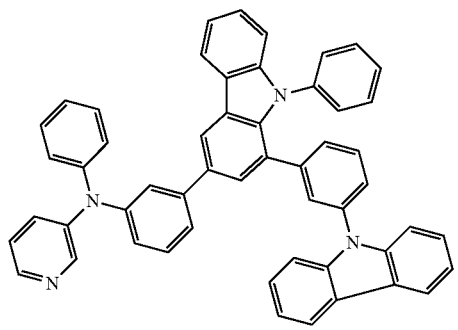
3-24
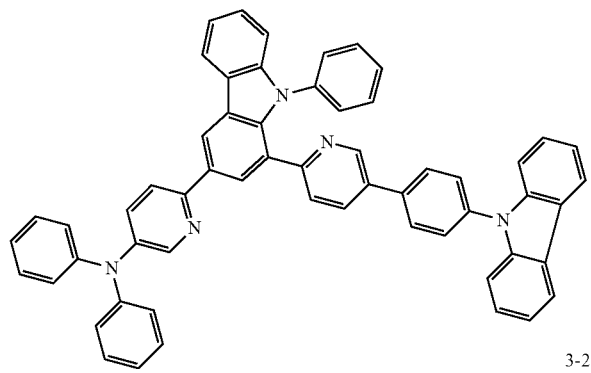
3-25
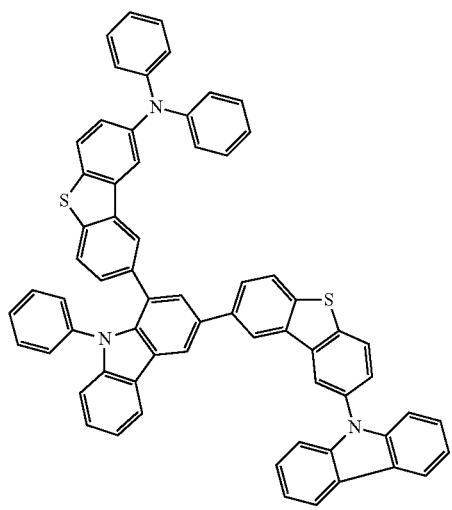
3-26
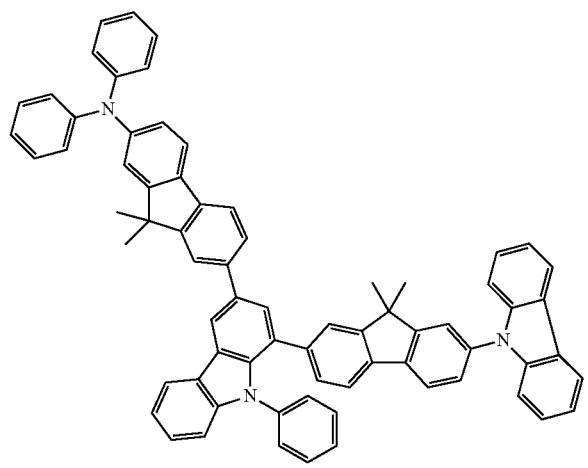

-continued
3-27
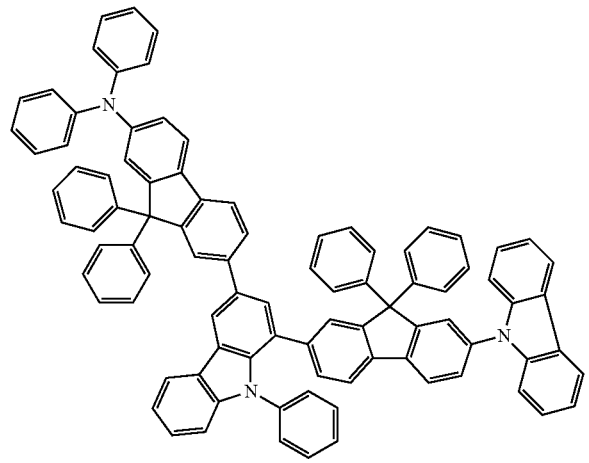
3-28
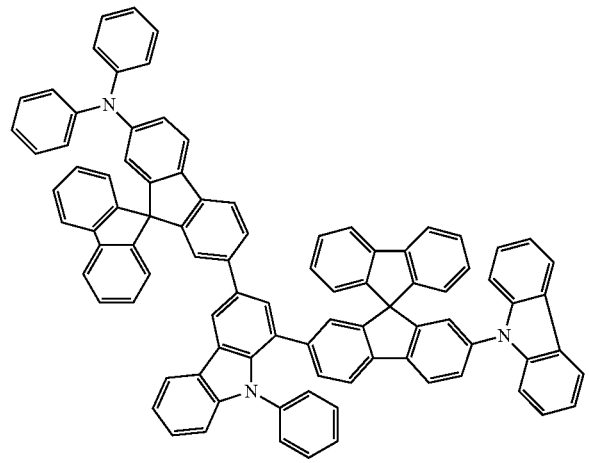
6-1
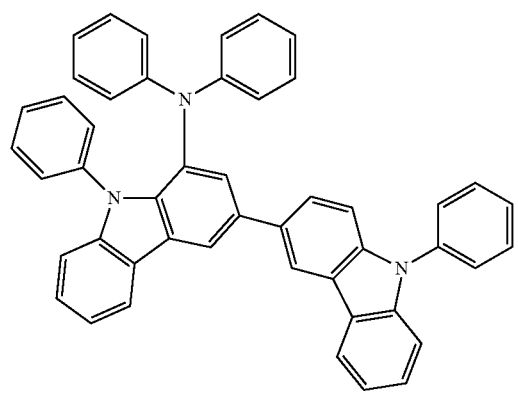
6-2
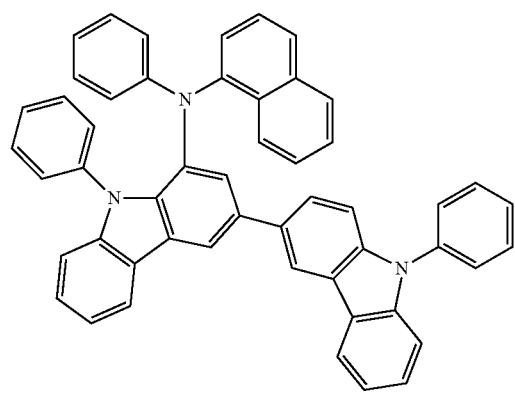
6-3
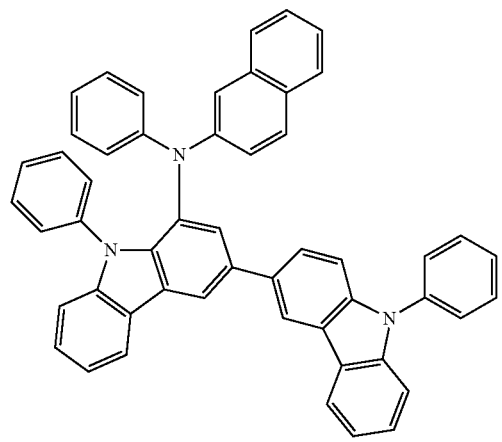
6-4
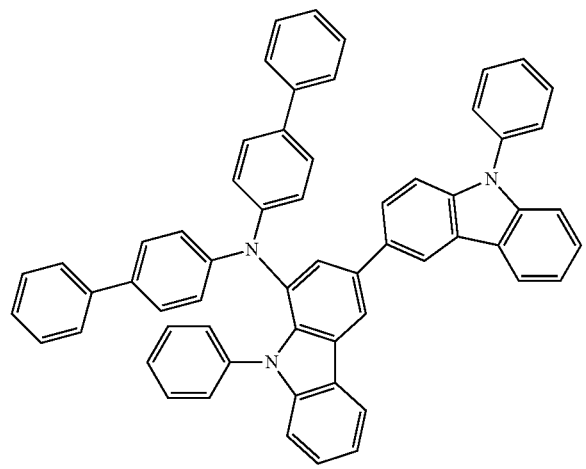

-continued
6-5
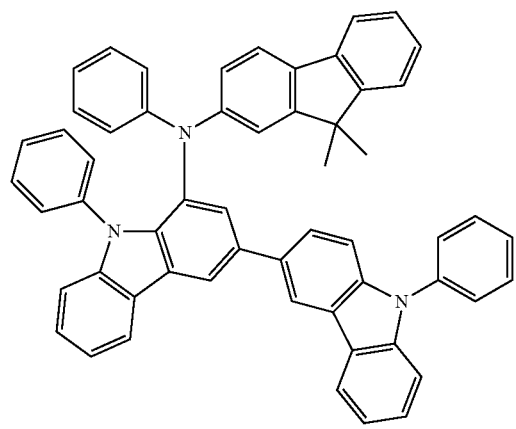
6-6
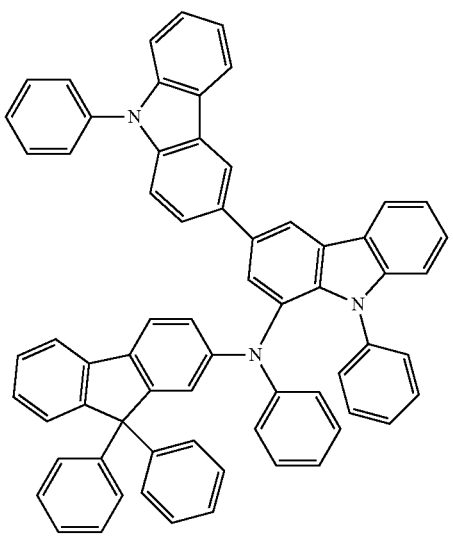
6-7
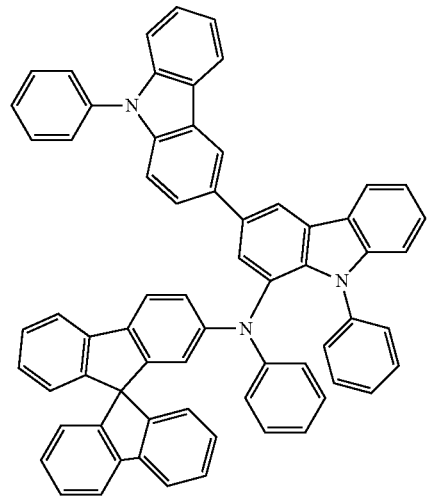
6-8
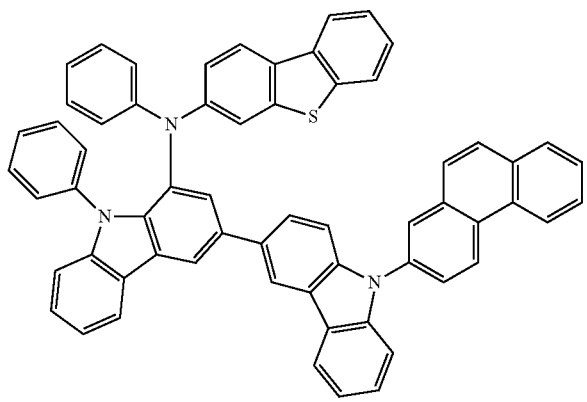
6-9
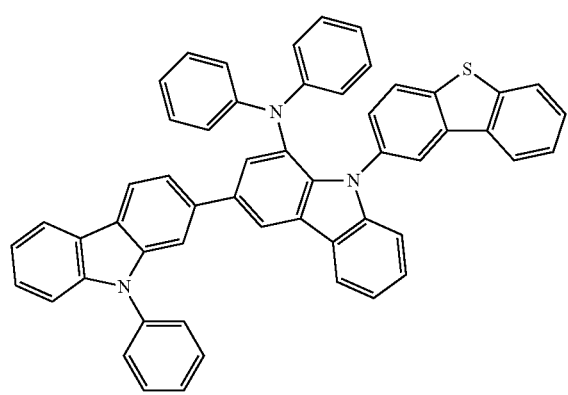
6-10
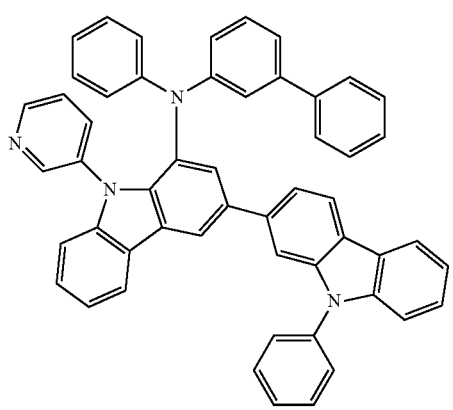

-continued
6-11
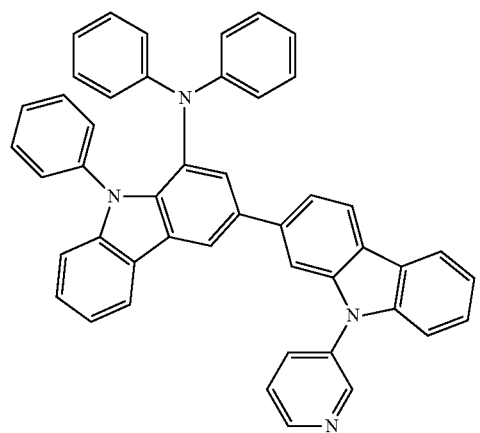
6-12
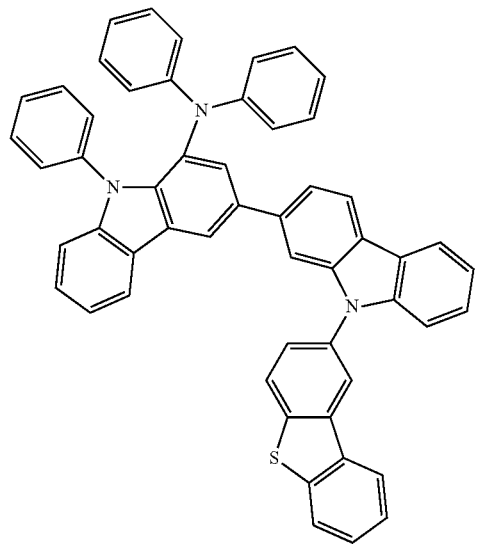
7-1
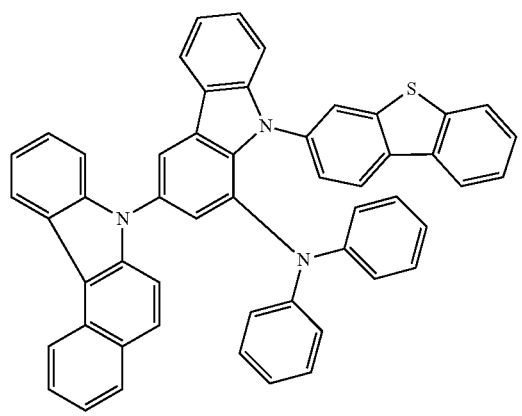
7-2
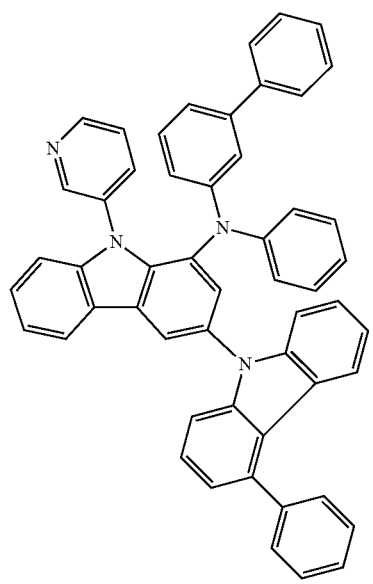
7-3
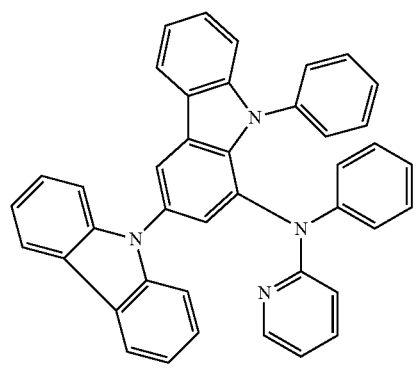
7-4
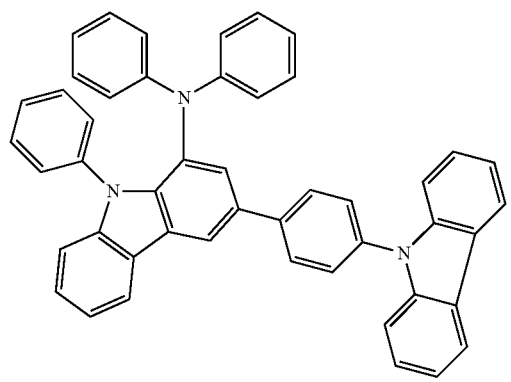

-continued 7-5
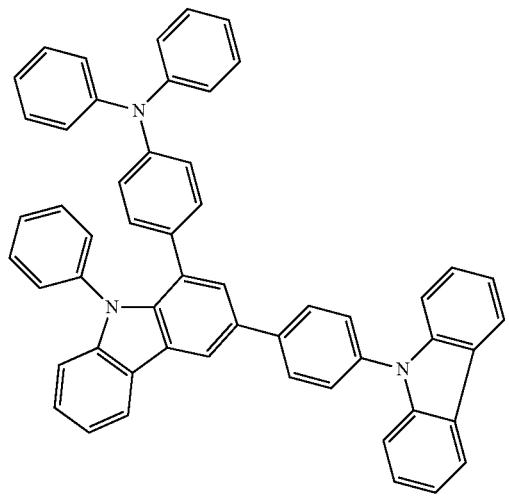

7-6
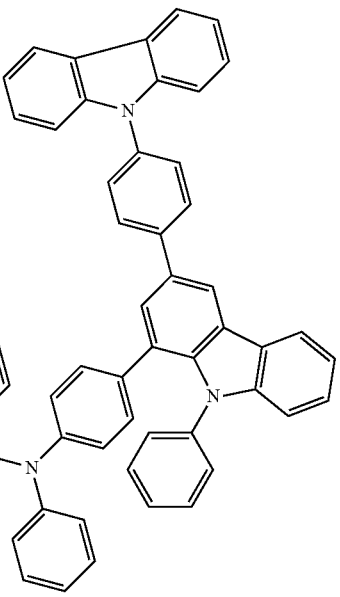

7-7
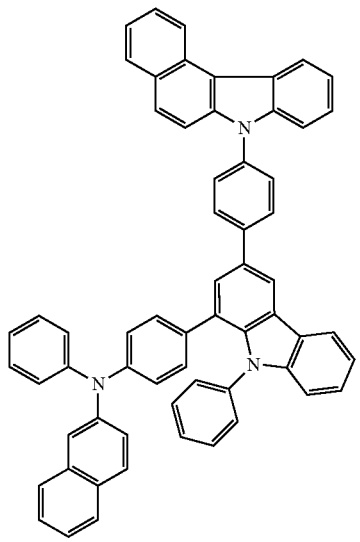

7-8
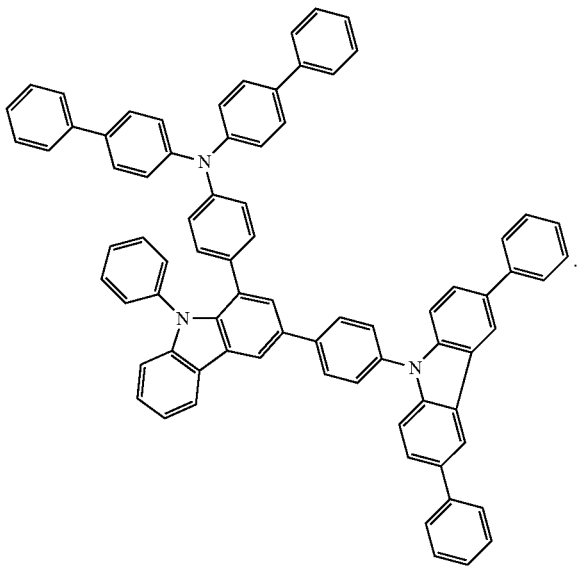

4. An organic electric element comprising a first electrode, a second electrode, and an organic material layer disposed between the first electrode and the second electrode, wherein the organic material layer comprises the compound of claim 1.

5. The organic electric element of claim 4, wherein at least one of a hole injection layer, a hole transport layer, an emission-auxiliary layer and an light emitting layer of the organic material layer comprises one kind or two or more kinds of compounds represented by Formula 1.

6. The organic electric element of claim 4, wherein the organic electric element further including at least one layer to improve luminous efficiency which is formed on at least one of the sides the first and second electrodes, which is opposite to the organic material layer.

7. The organic electric element of claim 4, wherein the organic material layer is formed by any one of the processes of spin coating, nozzle printing, inkjet printing, slot coating, dip coating and roll-to-roll.

8. An electronic device comprising:
a display device comprising the organic electric element of claim 1; and
a control unit for driving the display device.

9. The electronic device of claim 8, wherein the organic electric element comprises at least one of an organic light emitting diode, an organic solar cell, an organic photo conductor, an organic transistor, and an element for monochromatic or white illumination.

* * * * *